(12) United States Patent
Bialy et al.

(10) Patent No.: US 9,127,001 B2
(45) Date of Patent: Sep. 8, 2015

(54) SUBSTITUTED 4,5,6,7-TETRAHYDRO-1H-PYRAZOLO[4,3-C]PYRIDINES, THEIR USE AS MEDICAMENT, AND PHARMACEUTICAL PREPARATIONS COMPRISING THEM

(75) Inventors: Laurent Bialy, Kelkheim (DE); Katrin Lorenz, Kelkheim (DE); Klaus Wirth, Kriftel (DE); Klaus Steinmeyer, Frankfurt am Main (DE); Gerhard Hessler, Hofheim (DE); Josef Pernerstorfer, Hofheim (DE); Joachim Brendel, Bad Vilbel (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/342,744

(22) PCT Filed: Sep. 16, 2011

(86) PCT No.: PCT/EP2011/066061
§ 371 (c)(1),
(2), (4) Date: Jul. 17, 2014

(87) PCT Pub. No.: WO2013/037415
PCT Pub. Date: Mar. 21, 2013

(65) Prior Publication Data
US 2014/0330009 A1    Nov. 6, 2014

(51) Int. Cl.
*C07D 513/02* (2006.01)
*C07D 471/04* (2006.01)
*C07D 471/18* (2006.01)

(52) U.S. Cl.
CPC ............ *C07D 471/04* (2013.01); *C07D 471/18* (2013.01)

(58) Field of Classification Search
CPC .................................................... C07D 471/04
USPC ........................................................ 546/120
See application file for complete search history.

(56) References Cited

U.S. PATENT DOCUMENTS

| | | | |
|---|---|---|---|
| 4,500,525 A * | 2/1985 | Winters et al. ........... | 514/210.21 |
| 2008/0188477 A1 | 8/2008 | Brendel et al. | |
| 2008/0188520 A1 | 8/2008 | Brendel et al. | |
| 2013/0178475 A1 * | 7/2013 | Moore et al. .................. | 514/245 |

FOREIGN PATENT DOCUMENTS

| EP | 0086422 | 8/1983 |
|---|---|---|
| WO | 2005016965 A1 | 2/2005 |
| WO | 2006136304 A1 | 12/2006 |
| WO | 2007124849 A2 | 11/2007 |
| WO | 2011115804 A1 | 9/2011 |

OTHER PUBLICATIONS

The United States Department of Justice, "Former Research Chemist At Global Pharmaceutical Company Sentenced to 18 Months in Prison for Theft of Trade Secrets" The United States Attorney's Office, District of New Jersey, http://www.justice.gov/usao/nj/Press/files/Li,%20Yuan%20Sentencing%20News%20Release.html, pp. 1-2, May 7, 2012.
De Lousanoff, "Certified Copy in Extracts of No. 175 of the Roll of Deeds for 2011," CAS Search Results, pp. 1-19 Sep. 26, 2011.
Chemical Abstracts Registry No. 1279828-99-7, entered into STN on Apr. 14, 2011.
Chemical Abstracts Registry No. 1279034-76-2, entered into STN on Apr. 12, 2011.
Peukert S. et al., J. Med. Chem. (2003), vol. 46, p. 486-498.
Putzke C. et al., Cardiovasc. Res. (2007), vol. 75, p. 59-68.
Roden D.M., Am. J. Cardiol. (1993), vol. 72, p. 44B-49B.
Streit A.K. et al., J. Biol. Chem. (2011), vol. 286, p. 13977-13984.
Wakili R. et al., J. Clin. Invest. (2011), vol. 121, p. 2955-2968.
Aller M.I. et al., J. Neuroscience (2005), vol. 25, p. 11455-11467.
Barth A.S. et al., Pflugers—Arch. Eur. J. Physiol. (2005), vol. 450, p. 201-208.
Bayliss D.A. et al., Respiration Physiology (2001), vol. 129, p. 159-174.
Bayliss D.A. et al., Trends Pharmacological Sciences (2008), vol. 29, p. 566-575.
Berg A.P. et al., J. Neuroscience (2004), vol. 24, p. 6693-6702.
Bittner S. et al., Brain (2009), vol. 132, p. 2501-2516.
Brundel B.J.J.M. et al., J. Am. Coll. Cardiol. (2001), vol. 37, p. 926-932.
Buckler K.J. et al., J. Physiol. (2000), vol. 525.1, p. 135-142.
Coetzee W.J. et al., Ann. New York Acad. Sci. (1999), vol. 868, p. 233-285.
Colatsky T.J. et al., Drug Dev. Res. (1990), vol. 19, p. 129-149.
Cotten J.F. et al., Anesth. Analg. (2006), vol. 102, p. 779-785.
Dalisay D.S. et al., Angew. Chem. Int. Ed. (2009), vol. 48, p. 4367-4371.
Dobrev D. et al., Bas. Res. Cardiol. (2003), vol. 98, p. 137-148.
Donner B.C. et al., Bas. Res. Cardiol. (2011), vol. 106, p. 75-87.
Duprat F. et al., EMBO J. (1997), vol. 16, p. 5464-5471.
Ellinghaus P. et al., J. Thorac. Cardiovasc. Surg. (2005), vol. 129, p. 1383-1390.

(Continued)

*Primary Examiner* — Nizal Chandrakumar
(74) *Attorney, Agent, or Firm* — McDonnell Boehnen Hulbert & Berghoff

(57) ABSTRACT

The invention relates to substituted 4,5,6,7-tetrahydro-1H-pyrazolo[4,3-c]pyridines of formula (I), their use as medicament, and pharmaceutical preparations comprising them. The compounds of formula (I) act on the TASK-1 potassium channel. The compounds are particularly suitable for the treatment or prevention of atrial arrhythmias, for example atrial fibrillation (AF) or atrial flutter.

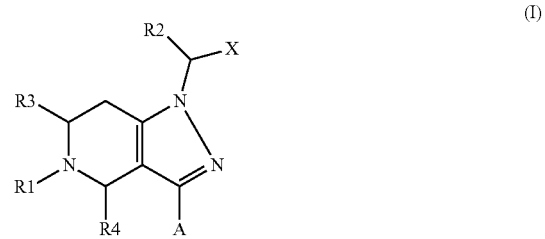

(I)

15 Claims, No Drawings

(56) References Cited

OTHER PUBLICATIONS

Knorr R. et al., Tetrahedron Lett. (1989), vol. 30, p. 1927-1930.pdf.
Kääb S. et al., J. Mol. Med. (2004), vol. 82, p. 308-316.
Knobloch K. et al., Naunyn Schmiedeberg's Arch. Pharmacol. (2002), vol. 366, p. 482-487.
Nozaki S., J. Peptide Res. (1999), vol. 54, p. 162-167.
Lauritzen I. et al., J. Biol. Chem. (2003), vol. 278, p. 32068-32076.
Maingret F. et al., EMBO J. 2001, vol. 20, p. 47-54.
Medhurst A.D. et al., Mol. Brain Res. (2001), vol. 86, p. 101-114.
Patel A.J. et al., Nature Neurosci. (1999), vol. 2, p. 422-426.
Patel A.J. et al., Pflugers Arch.—Eur. J. Physiol. (2004), vol. 448, p. 261-273.
Patel A.J. et al., Trends Neurosci. (2001), vol. 24, p. 339-346.
Winters G. et al., J. Med. Chem. (1985), vol. 28, p. 934-940.
Alterman M. et al., J. Org. Chem. (2000), vol. 65, p. 7984-7989.

* cited by examiner

SUBSTITUTED 4,5,6,7-TETRAHYDRO-1H-PYRAZOLO[4,3-C]PYRIDINES, THEIR USE AS MEDICAMENT, AND PHARMACEUTICAL PREPARATIONS COMPRISING THEM

This application is a national stage application under 35 U.S.C. §371 of International Application No. PCT/EP2011/066061, filed Sep. 16, 2011, the disclosure of which is explicitly incorporated by reference herein.

The invention relates to 4,5,6,7-tetrahydro-1H-pyrazolo[4,3-c]pyridine compounds of the formula I,

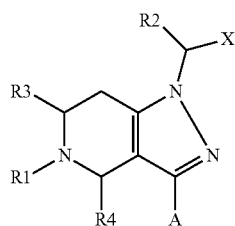

The compounds of formula I act on the TASK-1 (KCNK3) potassium channel. The compounds are suitable for the treatment of several pathologies and particularly suitable as anti-arrhythmic active ingredients, in particular for the treatment and prophylaxis of atrial arrhythmias, for example atrial fibrillation (AF) or atrial flutter.

Potassium channels are widespread membrane proteins which, owing to their influences on cell membrane potentials, play an important role in many physiological processes. Within the various classes of the potassium channels, a distinction is drawn on the basis of their molecular structure between three large groups which are characterized by the number of transmembrane domains (2, 4 or 6). The group of the potassium channels with four transmembrane segments is delimited from the two others in that their representatives each have two pore domains, which is why these channels are also referred to as $K_{2P}$ channels (Coetzee W. J. et al; Molecular diversity of K+ channels; Ann. New York Acad. Sci. 1999 (868), 233-285). In functional terms, $K_{2P}$ channels are characterized in that the "leak" or "background" currents flow through them, which play an important role for the resting membrane potential and hence the excitability of nerve or muscle cells.

A family which is of particular interest among the $K_{2P}$ channels is that of the TASK channels (tandem of P domains in a weak inwardly rectifying $K^+$ channel, [TWIK]-related acid-sensitive $K^+$ channels), which include TASK-1, TASK-3, and TASK-5 subtype (D. A. Bayliss, P. Barrett, Trends in Pharmacological Sciences, 2008, 29(11), 566-575). Other terms used in the literature for the underlying genes are KCNK3 or K2P3.1 (TASK-1), KCNK9 or K2P9.1 (TASK-3) and KCNK15 or K2P15.1 (TASK-5). The greatest homology within this family is possessed by the TASK-1 and TASK-3 channels with an amino acid identity of more than 50%. Dimerization of $K_{2P}$ channels forms functional potassium channels with a total of four pore units. The streams which flow through these channels are referred to in the literature as IKso stream. In addition to a homodimerization of, for example, two TASK-1 or two TASK-3 proteins, heterodimerization of TASK-1 and TASK-3 is also possible in this context (Berg A. P., Talley E. M., Manger J. P., Bayliss D. A.; Motoneurons express Heteromeric TWIK-related acid-sensitive K+(TASK) Channels containing TASK-1 (KCNK3) and TASK-3 (KCNK9) subunits; J. Neuroscience 2004 (24), 6693-6702).

The TASK channels are notable in particular for their very strong dependence upon the extracellular pH in the physiological range (pK ca. 6,5-7,5). The channels are inhibited at acidic pH and activated at alkaline pH. Owing to this pH dependence, the physiological function of a sensor which translates small changes in the extracellular pH to corresponding cellular signals is ascribed to the TASK channels (Duprat F., Lesage F., Fink M., Reyes R., Heurteaux C., Lazdunski M.; TASK, a human background K+ channel to sense external pH variations near physiological pH; EMBO J. 1997 (16), 5464-5471; Patel A. J., Honore E.; Properties and modulation of mammalian 2P domain K+ channels; Trends Neurosci. 2001 (24), 339-346).

TASK-1 knock-out mice show a mild phenotype and have been described and appear generally in good health and show normal breeding behaviour (Journal of Neuroscience (2005), 25(49), 11455-11467).

TASK-1 is expressed in the brain and also in spinal ganglia and some peripheral tissues, for example pancreas, placenta, uterus, lung, heart, kidney, small intestine and stomach. In addition, TASK-1 has been detected in the chemosensitive cells of the brainstem and of the carotid bodies, and also the motor neurons of the hypoglossal nerve (Medhurst A. D., Rennie G., Chapman C. G., Meadows H., Duckworth M. D., Kelsell R. E., Glober I. I., Pangalos M. N.; Distribution analysis of human two pore domain potassium channels in tissues of the central nervous system and periphery; Mol. Brain Res. 2001 (86), 101-114). Electrical currents which are caused by TASK-1 potassium channels have been detected in motor neurons of the hypoglossal nerve, a motor cranial nerve which possesses the most important function for the maintenance and patency of the upper respiratory pathways, and locus coeruleus. It has been found that TASK-1 channels are involved in respiratory regulation in respiratory neurons of the brainstem, in carotid bodies and in motor neurons of the hypoglossal nerve, and also in neuroepithelial cells of the lung. In the event of inadequate respiration (hypoxia, hindered breathing) and in the event of physical stress, either via a rise in the $CO_2$ concentration and the resulting acidosis or via acidic metabolites, there is a lowering of the pH and hence a blockage of the pH-dependent TASK-1 channels. This depolarizes the cells, which leads to the activation of the neurons involved in the respiratory regulation (Buckler K. J., Williams B. A., Honore E.; An oxygen-, acid- and anaesthetic-sensitive TASK-like background potassium channel in rat arterial chemoreceptor cells; J. Physiol. 2000 (525), 135-142; Bayliss D. A., Talley E. M., Sirois J. E., Lei Q.; TASK-1 is a highly modulated pH-sensitive 'leak' K+ channel expressed in brainstem respiratory neurons; Respiration Physiology 2001 (129), 159-174).

An increase in the activity of chemosensitive neurons in conjunction with an activation of the motor neurons of the hypoglossal nerve through blockage of the TASK-1 channel can stimulate respiration and simultaneously stabilize the upper airways to protect them from collapse and occlusion. Moreover, snoring can be inhibited by stabilizing the upper airway via an increase in pharyngeal muscle activity. The blockage of the TASK-1 ion channels is therefore useful in the treatment of respiratory disorders, for example of sleep apnea (Brendel, J.; Goegelein, H.; Wirth, K.; Kamm, W., WO 2007/124849).

In cultivated granulosa cells of the cerebellum, it has been shown that genetic inactivation of TASK channels brings about neuroprotective action (Lauritzen I., Zanzouri M., Honoré E., Duprat F., Ehrengruber M. U., Lazdunski M., Patel A. J.; K$^+$-dependent cerebellar granule neuron apoptosis—Role of Task leak K$^+$ channels; J. Biol. Chem. 2003 (278), 32068-32076). It has also been shown that TASK-1 channels are responsible for programmed cell death (apoptosis) in granulosa cells, and that the cell death can be prevented by blocking the TASK-3. Thus, the development of specific inhibitors of the TASK-⅓ channels can be useful for the treatment of neurodegenerative disorders (Patel A. J., Lazdunski M., The 2P-domain K$^+$ channels: role in apoptosis and tumorigenesis, Pflugers Arch. 2004 (448), 261-273).

It has been stated that TASK-1 is relevant for setting the resting membrane potential and balancing neuronal excitability that is expressed on T cells and neurons, and is a key modulator of T cell immunity and neurodegeneration in autoimmune central nervous system inflammation. After induction of experimental autoimmune encephalomyelitis, an experimental model mimicking multiple sclerosis, TASK1 (−/−) mice showed a significantly reduced clinical severity and markedly reduced axonal degeneration compared with wild-type controls. T cells from TASK1(−/−) mice displayed impaired T cell proliferation and cytokine production, while the immune repertoire is otherwise normal. In addition to these effects on systemic T cell responses, TASK1 exhibits an independent neuroprotective effect which was demonstrated using both a model of acutely prepared brain slices cocultured with activated T cells as well as in vitro cultivation experiments with isolated optic nerves. Preventive blockade of TASK1 significantly ameliorated experimental autoimmune encephalomyelitis after immunization and significantly reduced disease severity and was capable of lowering progressive loss of brain parenchymal volume as assessed by magnetic resonance imaging. Thus TASK-1 blockers are potent compounds useful for the therapy of inflammatory and degenerative central nervous system disorders (Bittner Stefan; Meuth Sven G; Gobel Kerstin; Melzer Nico; Herrmann Alexander M; Simon Ole J; Weishaupt Andreas; Budde Thomas; Bayliss Douglas A; Bendszus Martin; Wiendl Heinz, Brain: a journal of neurology (2009), 132(Pt 9), 2501-16).

TASK-1, a member of two-pore-domain (K2P) potassium channel family, has emerged as a target for the pharmacological treatment of atrial fibrillation recently. Two-pore-domain (K2P) potassium channels mediate background potassium currents, stabilizing resting membrane potential and expediting action potential repolarization. In the heart, TASK-1 channels have been shown to play a role in cardiac repolarization, (Basic Res Cardiol. 2011 January; 106(1):75-87, Putzke C, Wemhöner K, Sachse F B, Rinné S, Schlichthörl G, Li X T, Jaé L, Eckhardt I, Wischmeyer E, Wulf H, Preisig-Müller R, Daut J, Decher N (2007), Cardiovascular Research, 75: 59-68).

Atrial fibrillation (AF) and atrial flutter are extremely common cardiac rhythm disorder that causes substantial morbidity and contributes to mortality (Journal of Clinical Invest. 2011; 121 (8):2955-2968). Presently available therapeutic approaches have major limitations, including limited efficacy and potentially serious side effects such as malignant ventricular arrhythmia induction or negative inotropic effects. The occurrence of AF increases with age and frequently leads to fatal sequelae such as stroke. The class I and III antiarrhythmics in use at present reduce the rate of recurrence of AF but are used to only a limited extent because of their potential proarrhythmic side effects and limited efficacy. The growing incidence of AF emphasizes the importance of identifying appropriate treatments, particularly drugs, that are safe, effective, and associated with improved clinical outcomes.

It has been shown that in atrial fibrillation and flutter re-entrant mechanism play an important role in the induction and maintenance of the arrhythmia. Such reentries or re-entrant waves occur when the cardiac tissue has a low conduction velocity and, at the same time, short refractory periods. Increasing the myocardial refractory period by prolonging the action potential is an acknowledged mechanism for terminating arrhythmias or for preventing them to develop (T. J. Colatsky et al., Drug Dev. Res. 19, 1990, 129-140; "Potassium channels as targets for antiarrhythmic drug action"). The length of the action potential is essentially determined by the extent of repolarizing K$^+$ currents which flow out of the cells through various K$^+$ channels. TASK-1 constitutes one of those repolarizing potassium currents. Its inhibition prolong the action potential and thereby refractoriness.

Most of the known class III antiarrhythmics (e.g. dofetilide, E4031 and d-sotalol) block predominantly or exclusively the rapidly activating potassium channel $IK_r$, which can be detected both in cells of the human ventricle and in the atrium. It has emerged that these compounds have an increased proarrhythmic risk at heart rates which are low or normal, and arrhythmias referred to as torsades de pointes have been observed in particular (D. M. Roden, Am. J. Cardiol. 72, 1993, 44B-49B; "Current status of class III antiarrhythmic drug therapy"). Apart from this proarrhythmic risk, the therapeutic efficacy of the $I_{Kr}$ blockers has been found to decline under the conditions of tachycardia (electrical tachycardic atrial remodelling).

TASK-1 expression in the human heart has been shown to be restricted to the atria with no or very little expression in the ventricles. A further advantage is that TASK-1 expression is not decreased but even slightly increased in atrial fibrillation patients compared with sinus rhythm patients, by contrast a decreased expression of other atrial K$^+$ channels has been reported in atrial fibrillation patients compared with sinus rhythm patients: see for example Basic. Res. Cardiol. 2003, 98, 137-148, JACC Vol. 37, No. 3, 2001). Thus, TASK-1 is still expressed in the target patient population (Journal of Molecular Medicine 2004, 308-316; European Journal of Physiology 2005, 450, 201-208, WO 2005/016965; Journal of Thoracic and Cardiovascular Surgery 2005).

In spite of the great physiological significance of the TASK channels, only very few pharmacological modulators of these channels are known to date in the literature.

It has been stated that an activation of the TASK-1 channel can be achieved by therapeutic concentrations of the inhalative anesthetics halothane and isoflurane (Patel A. J., Honoré E., Lesage F., Fink M., Romey G., Lazdunski M.; Inhalational anesthetics activate two-pore-domain background K+ channels; Nature Neurosci. 1999 (2), 422-426). Furthermore, some Kv1.5 blockers which also inhibit the TASK-channel are described in the state of the art (Brendel, J.; Goegelein, H.; Wirth, K.; Kamm, W., WO 2007/124849, Brendel, J.; Englert, H. C.; Wirth, K.; Wagner, M.; Ruxer, J.-M.; Pilorge, F., WO 2006/136304). A1899, a previously described Kv1.5 blocker (Peukert, S., Brendel, J., Pirard, B., Brueggemann, A., Below, P., Kleemann, H.-W., Hemmerle, H., Schmidt, W.; Identification, Synthesis, and Activity of Novel Blockers of the Voltage-Gated Potassium Channel Kv1.5; Journal of Medicinal Chemistry (2003), 46(4), 486-498) has been stated to be a TASK-1 blocker (Streit, A. K.; Netter, M. F., Kempf, F., Walecki, M., Rinne, S., Bollepalli, M. K.; Preisig-Mueller, R.; Renigunta, V.; Daut, J.; Baukrowitz, T.; Sansom, M. S. P.; Stansfeld, P. J.; Decher, N. A Specific Two-pore Domain Potassium Channel Blocker Defines the Structure of the TASK-1 Open Pore; Journal of Biological Chemistry (2011), 286(16), 13977-13984). Also arachidonamide anandamide (an endogenous ligand of the cannabinoid receptor) and its methanandamide homolog have been described as TASK-1 blockers (Maingret F., Patel A. J., Lazdunski M., Honoré E.; The endocannabinoid anandamide is a direct and selective blocker of the background K+ channel TASK-1; EMBO J. 2001 (20), 47-54). Doxapram, which is used for the treatment of respiratory disorders has been stated to be a TASK-1 blocker (Cotten J. F., Keshavaprasad B., Laster M. J., Eger E. I., Yost C. S.; The Ventilatory Stimulant Doxapram Inhibits TASK Tandem Pore ($K_{2P}$) Potassium Channel Function but Does Not Affect Minimum Alveolar Anesthetic Concentration; Anesth. Analg. 2006 (102) 779-785).

EP 0 086 422 A2 describes some N-acetylated tetrahydro-1H-pyrazolo[4,3-c]pyridine compounds. However no biological activity has been described for these compounds therein.

Thus, a goal of the present invention is to provide efficient TASK-1 inhibitors suitable for the treatment and prevention of TASK-1 related conditions. The present invention relates to TASK-1 blockers of the formula I

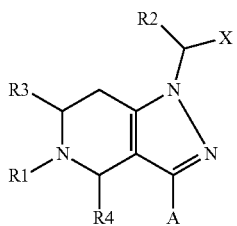

wherein
A=($C_6$-$C_{10}$)-aryl or a five- or six-membered heteroaryl, comprising 1-3 heteroatoms selected from the group N, O and S,
  wherein aryl and heteroaryl are optionally substituted with 1-3 rests selected independently from F, Cl, Br, CN, ($C_1$-$C_6$)-alkyl-, ($C_1$-$C_6$)-alkyl-O— and ($C_1$-$C_6$)-alkyl-S—,
    wherein one or more hydrogen atoms of the alkyl moieties may be replaced by fluorine;
X=($C_6$-$C_{10}$)-aryl or a five- or six-membered heteroaryl, comprising 1-3 heteroatoms selected from the group N, O and S,
  wherein aryl and heteroaryl are optionally substituted with 1-3 rests selected independently from F, Cl, Br, CN, ($C_1$-$C_6$)-alkyl-, ($C_1$-$C_6$)-alkyl-O—, ($C_1$-$C_6$)-alkyl-S—, ($C_1$-$C_6$)-alkyl-O—C(O)— and ($C_1$-$C_6$)-alkyl-$SO_2$—,
    wherein one or more hydrogen atoms of the alkyl moieties may be replaced by fluorine;
R1=R5-C(=O)— or ($C_1$-$C_6$)-alkyl-$SO_2$—;
R2=H, ($C_1$-$C_6$)-alkyl-, ($C_3$-$C_6$)-cycloalkyl-;
R3=H, ($C_1$-$C_4$)-alkyl-;
R4=H, ($C_1$-$C_4$)-alkyl-;
or wherein R3 and R4 together form a ($C_2$-$C_3$)-alkylene bridge;
R5=H, ($C_1$-$C_6$)-alkyl-, ($C_3$-$C_6$)-cycloalkyl-, ($C_1$-$C_6$)-alkyl-O—, ($C_1$-$C_6$)-alkyl-S—, ($C_1$-$C_6$)-alkyl-O—($C_1$-$C_6$)-alkyl-, HO—($C_1$-$C_6$)-alkyl-, ($C_3$-$C_6$)-cycloalkyl-($C_1$-$C_6$)-alkyl-, ($C_6$-$C_{10}$)-aryl-, ($C_6$-$C_{10}$)-aryl-($C_1$-$C_6$)-alkyl-, R7R6N—, heteroaryl, heteroaryl-($C_1$-$C_6$)-alkyl-, aliphatic heterocycle,
  wherein one or more hydrogen atoms of the alkyl moieties may be replaced by fluorine, and
  wherein the aliphatic heterocycle is selected from the group of morpholinyl, piperidinyl, pyrrolidinyl and 4 to 7 membered aliphatic heterocycles comprising an oxygen atom, and
  wherein the aliphatic heterocycle may be optionally substituted with 1 to 3 substituents independently selected from the group of F, OH, ($C_1$-$C_6$)-alkyl-O— and ($C_1$-$C_6$)-alkyl-, and
  wherein the heteroaryl residues are five- or six-membered ring systems, comprising 1-3 heteroatoms selected from the group N, O and S, and
  wherein aryl and heteroaryl are optionally substituted with 1-3 rests selected independently from F, Cl, Br, $CF_3$, ($C_1$-$C_6$)-alkyl-, ($C_1$-$C_6$)-alkyl-O—, CN, ($C_1$-$C_2$)-alkyl-$SO_2$—;
R6=H, ($C_1$-$C_6$)-alkyl-, ($C_3$-$C_6$)-cycloalkyl-,
  wherein one hydrogen atom of the alkyl group may be replaced by an OH or ($C_1$-$C_6$)-alkyl-O— residue, and
  wherein one or more hydrogen atoms of the alkyl group may be replaced by fluorine;
R7=H, ($C_1$-$C_6$)-alkyl-;
  wherein one or more hydrogen atoms of the alkyl group may be replaced by fluorine,
and/or of a stereoisomeric form of the compound of the formula I and/or mixtures of these forms, and/or their pharmaceutically acceptable salts, and
with the proviso if R5 is methyl and R2, R3 and R4 are equal to H and A is equal to 4-fluoro-phenyl, the residue X is not phenyl, 4-fluoro-phenyl, 4-chloro-phenyl, 4-methyl-phenyl, 4-methoxy-phenyl, 4-acetoxyphenyl, 2-chloro-phenyl, 3,4-dichlorophenyl, and
with the proviso if R5 is methyl and R2, R3 and R4 are equal to H and X is a phenyl residue, the residue A is not phenyl, 4-fluoro-phenyl, 4-chloro-phenyl, 4-methyl-phenyl, 4-ethyloxy-phenyl, 3-trifluoromethyl-phenyl, 2-thiophenyl or 4-methylthiophenyl, and
with the proviso if R5 is methyl and R2 is methyl and R3 and R4 are equal to H and A is equal to 4-fluoro-phenyl, the residue X is not phenyl.

A preferred embodiment of the present invention relates to compounds, wherein
A=phenyl or a five- or six-membered heteroaryl selected from the group consisting of pyridine-2-yl, pyridine-3-yl, pyridine-4-yl, thiophen-2-yl or thiophen-3-yl,
  wherein phenyl and heteroaryl are optionally substituted with 1-3 rests selected independently from F, Cl, Br, CN, ($C_1$-$C_6$)-alkyl-, ($C_1$-$C_6$)-alkyl-O— and ($C_1$-$C_6$)-alkyl-S—,
    wherein one or more hydrogen atoms of the alkyl moieties may be replaced by fluorine;
X=a five- or six-membered heteroaryl, comprising 1-3 heteroatoms selected from the group N, O and S,
  wherein the heteroaryl group is optionally substituted with 1-3 residues selected independently from F, Cl, Br, CN, ($C_1$-$C_6$)-alkyl-, ($C_1$-$C_6$)-alkyl-O— and ($C_1$-$C_6$)-alkyl-S—, ($C_1$-$C_6$)-alkyl-O—C(O)— and ($C_1$-$C_6$)-alkyl-$SO_2$—,
    wherein one or more hydrogen atoms of the alkyl moieties may be replaced by fluorine;
R1=R5-C(=O)— or ($C_1$-$C_6$)-alkyl-$SO_2$—;
R2=H, ($C_1$-$C_4$)-alkyl-, ($C_3$-$C_6$)-cycloalkyl-;
R3=H, ($C_1$-$C_2$)-alkyl-;
R4=H, ($C_1$-$C_2$)-alkyl-;
or wherein R3 and R4 together form a ($C_2$-$C_3$)-alkylene bridge;
R5=H, ($C_1$-$C_6$)-alkyl-, ($C_3$-$C_6$)-cycloalkyl-, ($C_1$-$C_6$)-alkyl-O—, ($C_1$-$C_6$)-alkyl-S—, ($C_1$-$C_6$)-alkyl-O—($C_1$-$C_6$)- alkyl-, HO—($C_1$-$C_6$)-alkyl-, ($C_3$-$C_6$)-cycloalkyl-($C_1$-$C_6$)-alkyl-, ($C_6$-$C_{10}$)-aryl-, ($C_6$-$C_{10}$)-aryl-($C_1$-$C_6$)-alkyl-, R7R6N—, heteroaryl, heteroaryl-($C_1$-$C_6$)-alkyl-, aliphatic heterocycle,
  wherein one or more hydrogen atoms of the alkyl moieties may be replaced by fluorine, and
  wherein the aliphatic heterocycle is selected from the group of morpholinyl, piperidinyl, pyrrolidinyl and 4 to 7 membered aliphatic heterocycles comprising an oxygen atom, and
  wherein the aliphatic heterocycle may be optionally substituted with 1 to 3 substituents independently selected from the group of F, OH, ($C_1$-$C_6$)-alkyl-O— and ($C_1$-$C_6$)-alkyl-, and
  wherein the heteroaryl residues are five- or six-membered ring systems, comprising 1-3 heteroatoms selected from the group N, O and S, and
  wherein aryl and heteroaryl are optionally substituted with 1-3 rests selected independently from F, Cl, Br, $CF_3$, ($C_1$-$C_6$)-alkyl-, ($C_1$-$C_6$)-alkyl-O—, CN, ($C_1$-$C_2$)-alkyl-$SO_2$—;
R6=H, ($C_1$-$C_6$)-alkyl-, ($C_3$-$C_6$)-cycloalkyl-,
  wherein one hydrogen atom of the alkyl group may be replaced by an OH— or ($C_1$-$C_6$)-alkyl-O— residue, and
  wherein one or more hydrogen atoms of the alkyl group may be replaced by fluorine;
R7=H, ($C_1$-$C_6$)-alkyl-;
  wherein one or more hydrogen atoms of the alkyl group may be replaced by fluorine,
and/or of a stereoisomeric form of the compound of the formula I and/or mixtures of these forms, and/or their pharmaceutically acceptable salts.

Preferred compounds are, wherein
A=phenyl,
  wherein the phenyl residue is optionally substituted with 1-3 rests selected independently from F, Cl, Br, CN, ($C_1$-$C_4$)-alkyl-, ($C_1$-$C_4$)-alkyl-O— and ($C_1$-$C_4$)-alkyl-S—,
    wherein one or more hydrogen atoms of the alkyl moieties may be replaced by fluorine;
X=a five- or six-membered heteroaryl, selected from the group consisting of pyridine-2-yl, pyridine-3-yl, pyridine-4-yl, thiophen-2-yl, thiophen-3-yl, thiazol-2-yl, thiazol-4-yl, thiazol-5-yl,
  wherein the heteroaryl group is optionally substituted with 1-3 residues selected independently from F, Cl, Br, CN, ($C_1$-$C_6$)-alkyl-, ($C_1$-$C_6$)-alkyl-O— and ($C_1$-$C_6$)-alkyl-S—, ($C_1$-$C_6$)-alkyl-O—C(O)— and ($C_1$-$C_6$)-alkyl-$SO_2$—,
    wherein one or more hydrogen atoms of the alkyl moieties may be replaced by fluorine;
R1=R5-C(=O)— or ($C_1$-$C_2$)-alkyl-$SO_2$—;
R2=H, ($C_1$-$C_2$)-alkyl-, cyclopropyl-;
R3=H, methyl-;
R4=H, methyl-;
or wherein R3 and R4 together form an ethylene bridge; and wherein
R5=H, ($C_1$-$C_4$)-alkyl-, ($C_3$-$C_6$)-cycloalkyl-, ($C_1$-$C_2$)-alkyl-O—, ($C_1$-$C_2$)-alkyl-S—, ($C_1$-$C_4$)-alkyl-O-methyl-, HO—($C_1$-$C_2$)-alkyl-, ($C_3$-$C_6$)-cycloalkyl-($C_1$-$C_2$)-alkyl-, phenyl, phenyl-($C_1$-$C_2$)-alkyl-, R7R6N—, heteroaryl, heteroaryl-($C_1$-$C_4$)-alkyl-, aliphatic heterocycle,
  wherein one or more hydrogen atoms of the alkyl moieties may be replaced by fluorine, and
  wherein the aliphatic heterocycle is selected from the group of morpholinyl, piperidinyl, pyrrolidinyl, oxetanyl, tetrahydrofuranyl, and tetrahydropyranyl, and
  wherein the aliphatic heterocycle may be optionally substituted with 1 or 2 substituents independently selected from the group of F, OH, ($C_1$-$C_2$)-alkyl-O— and ($C_1$-$C_4$)-alkyl-, and
  wherein the phenyl residue is optionally substituted with 1-3 rests selected independently from F, Cl, Br, $CF_3$, ($C_1$-$C_4$)-alkyl-, ($C_1$-$C_4$)-alkyl-O—, CN, ($C_1$-$C_2$)-alkyl-$SO_2$—
  wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and pyrazin-3-yl, and
  wherein the heteroaryl residues are optionally substituted with 1 or 2 rests selected independently from F, Cl, Br, $CF_3$, ($C_1$-$C_4$)-alkyl-, ($C_1$-$C_4$)-alkyl-O—, CN, ($C_1$-$C_2$)-alkyl-$SO_2$—;
R6=H, ($C_1$-$C_4$)-alkyl-, cyclopropyl,
  wherein one hydrogen atom of the alkyl group may be replaced by an OH, methoxy or ethoxy residue; and
R7=H, methyl-, ethyl;
and/or of a stereoisomeric form of the compound of the formula I and/or mixtures of these forms, and/or their pharmaceutically acceptable salts.

Particularly preferred compounds are, wherein
A=phenyl,
  wherein the phenyl residue is optionally substituted with 1 or 2 rests selected independently from F, Cl, Br, CN, ($C_1$-$C_4$)-alkyl-, $CF_3$, $CF_2H$, $CFH_2$, methoxy, ethoxy, $OCF_3$, and ($C_1$-$C_2$)-alkyl-S—;
X=a five- or six-membered heteroaryl, selected from the group consisting of pyridine-2-yl, pyridine-3-yl, pyridine-4-yl, thiophen-2-yl, thiophen-3-yl, thiazol-2-yl, thiazol-4-yl, thiazol-5-yl,
  wherein these residues are optionally substituted with 1 or 2 residues selected independently from F, Cl, Br, CN, ($C_1$-$C_4$)-alkyl-, $CF_3$, $CF_2H$, $CFH_2$, methoxy, ethoxy, $OCF_3$, ($C_1$-$C_2$)-alkyl-S—, ($C_1$-$C_2$)-alkyl-O—C(O)— and methyl-$SO_2$—;
R1=R5-C(=O)— or ($C_1$-$C_2$)-alkyl-$SO_2$—;
R2=H, methyl, ethyl, cyclopropyl;
R3 and R4=H, and
R5=methyl, ethyl, n-propyl, isopropyl, n-butyl, isobutyl, tert.-butyl, cyclopropyl or cyclobutyl;
and/or of a stereoisomeric form of the compound of the formula I and/or mixtures of these forms, and/or their pharmaceutically acceptable salts.

A further preferred embodiment of the present invention relates to compounds, wherein
A=a five- or six-membered heteroaryl, comprising 1-3 heteroatoms selected from the group N, O and S,
  wherein the heteroaryl is substituted with 1-3 residues selected independently from F, Cl, Br, CN, ($C_1$-$C_6$)-alkyl-, ($C_1$-$C_6$)-alkyl-O— and ($C_1$-$C_6$)-alkyl-S—,
    wherein one or more hydrogen atoms of the alkyl moieties may be replaced by fluorine;
X=phenyl, thiophen-2-yl or thiophen-3-yl,
  wherein these residues are optionally substituted with 1-3 rests selected independently from F, Cl, Br, CN, ($C_1$-$C_6$)-alkyl-, ($C_1$-$C_6$)-alkyl-O— and ($C_1$-$C_6$)-alkyl-S—, ($C_1$-$C_6$)-alkyl-O—C(O)— and ($C_1$-$C_6$)-alkyl-$SO_2$—,
    wherein one or more hydrogen atoms of the alkyl moieties may be replaced by fluorine;
R1=R5-C(=O)— or ($C_1$-$C_6$)-alkyl-$SO_2$—;

R2=H, $(C_1$-$C_6)$-alkyl-, $(C_3$-$C_6)$-cycloalkyl-;
R3=H, $(C_1$-$C_4)$-alkyl-;
R4=H, $(C_1$-$C_4)$-alkyl-;
or wherein R3 and R4 together form a $(C_2$-$C_3)$-alkylene bridge;
R5=H, $(C_1$-$C_6)$-alkyl-, $(C_3$-$C_6)$-cycloalkyl-, $(C_1$-$C_6)$-alkyl-O—, $(C_1$-$C_6)$-alkyl-S—, $(C_1$-$C_6)$-alkyl-O—$(C_1$-$C_6)$-alkyl-, HO—$(C_1$-$C_6)$-alkyl-, $(C_3$-$C_6)$-cycloalkyl-$(C_1$-$C_6)$-alkyl-, $(C_6$-$C_{10})$-aryl-, $(C_6$-$C_{10})$-aryl-$(C_1$-$C_6)$-alkyl-, R7R6N—, heteroaryl, heteroaryl-$(C_1$-$C_6)$-alkyl-, aliphatic heterocycle,
  wherein one or more hydrogen atoms of the alkyl moieties may be replaced by fluorine, and
  wherein the aliphatic heterocycle is selected from the group of morpholinyl, piperidinyl, pyrrolidinyl and 4 to 7 membered aliphatic heterocycles comprising an oxygen atom, and
  wherein the aliphatic heterocycle may be optionally substituted with 1 to 3 substituents selected from the group of F, OH, $(C_1$-$C_6)$-alkyl-O— and $(C_1$-$C_6)$-alkyl-, and
  wherein the heteroaryl residues are five- or six-membered ring systems, comprising 1-3 heteroatoms selected from the group N, O and S, and
  wherein aryl and heteroaryl are optionally substituted with 1-3 rests selected independently from F, Cl, Br, $CF_3$, $(C_1$-$C_6)$-alkyl-, $(C_1$-$C_6)$-alkyl-O—, CN, $(C_1$-$C_2)$-alkyl-$SO_2$—;
R6=H, $(C_1$-$C_6)$-alkyl-, $(C_3$-$C_6)$-cycloalkyl-,
  wherein one hydrogen atom of the alkyl group may be replaced by an OH— or $(C_1$-$C_6)$-alkyl-O— residue, and
  wherein one or more hydrogen atoms of the alkyl group may be replaced by fluorine;
R7=H, $(C_1$-$C_6)$-alkyl-;
  wherein one or more hydrogen atoms of the alkyl group may be replaced by fluorine,
and/or of a stereoisomeric form of the compound of the formula I and/or mixtures of these forms, and/or their pharmaceutically acceptable salts,
with the proviso that A is not 4-methylthiophenyl if in compounds of formula I R5 is methyl and R2, R3 and R4 are hydrogen and X is phenyl.

Preferred compounds are, wherein
A=2-pyridyl, 3-pyridyl or 4-pyridyl,
  wherein the pyridyl residues are substituted with 1 or 2 residues selected independently from F, Cl, Br, CN, $(C_1$-$C_4)$-alkyl-, $CF_3$, $CF_2H$, $CFH_2$, methoxy, ethoxy, $OCF_3$, and $(C_1$-$C_2)$-alkyl-S—;
X=phenyl, thiophen-2-yl or thiophen-3-yl,
  wherein these residues are substituted with 1 or 2 residues selected independently from F, Cl, Br, CN, $(C_1$-$C_4)$-alkyl-, $CF_3$, $CF_2H$, $CFH_2$, methoxy, ethoxy, $OCF_3$, $(C_1$-$C_2)$-alkyl-S—, $(C_1$-$C_2)$-alkyl-O—C(O)— and methyl-$SO_2$—;
R1=R5-C(=O)— or $(C_1$-$C_2)$-alkyl-$SO_2$—;
R2=H, methyl, ethyl, cyclopropyl;
R3 and R4=H; and
R5=H, methyl, ethyl, n-propyl, isopropyl, n-butyl, isobutyl or tert.-butyl or wherein
R5=cyclopropyl, cyclobutyl, cyclopentyl or $(C_3$-$C_6)$-cycloalkyl-$(C_1$-$C_2)$-alkyl-;
or wherein
R5=$(C_1$-$C_2)$-alkyl-O—, $(C_1$-$C_2)$-alkyl-S—, or $OCF_3$,
or wherein
R5=$(C_1$-$C_4)$-alkyl-O-methyl-, HO—$(C_1$-$C_2)$-alkyl-,
or wherein
R5=phenyl or phenylmethyl-,
  wherein the phenyl residues are optionally substituted with 1-3 rests selected independently from F, Cl, Br, $CF_3$, $(C_1$-$C_2)$-alkyl-, $(C_1$-$C_2)$-alkyl-O—, CN, methyl-$SO_2$—;
or wherein,
R5=R7R6N—, wherein
R6=H, $(C_1$-$C_4)$-alkyl-, cyclopropyl,
  wherein one hydrogen atom of the alkyl group may be replaced by an OH, methoxy or ethoxy residue; and
R7=H, methyl-, ethyl;
or wherein
R5=heteroaryl, heteroaryl-$(C_1$-$C_6)$-alkyl-,
  wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and payrazin-3-yl, and
  wherein the heteroaryl residues are optionally substituted with 1 or 2 rests selected independently from F, Cl, Br, $CF_3$, $(C_1$-$C_4)$-alkyl-, $(C_1$-$C_4)$-alkyl-O—, CN, $(C_1$-$C_2)$-alkyl-$SO_2$—;
or wherein
R5=an aliphatic heterocycle,
  wherein the aliphatic heterocycle is selected from the group of morpholinyl, piperidinyl, pyrrolidinyl, oxetanyl and tetrahydrofuranyl, tetrahydropyranyl, and
  wherein the aliphatic heterocycle may be optionally substituted with 1 or 2 substituents independently selected from the group of F, OH, $(C_1$-$C_2)$-alkyl-O— and $(C_1$-$C_4)$-alkyl-;
and/or of a stereoisomeric form of the compound of the formula I and/or mixtures of these forms, and/or their pharmaceutically acceptable salts.

A further preferred embodiment of the present invention relates to compounds, wherein
A is equal to phenyl,
  wherein the phenyl residue is optionally substituted with 1-3 residues selected independently from F, Cl, Br, CN, $(C_1$-$C_4)$-alkyl-, $(C_1$-$C_4)$-alkyl-O— and $(C_1$-$C_4)$-alkyl-S—,
    wherein one or more hydrogen atoms of the alkyl moieties may be replaced by fluorine, and
X is equal to phenyl,
  wherein the phenyl group is optionally substituted with 1, 2 or 3 residues selected independently from F, Cl, Br, CN, $(C_1$-$C_4)$-alkyl-, $(C_1$-$C_4)$-alkyl-O—, $(C_1$-$C_4)$-alkyl-S—, $(C_1$-$C_4)$-alkyl-O—C(O)— and $(C_1$-$C_4)$-alkyl-$SO_2$—,
    wherein one or more hydrogen atoms of the alkyl moieties may be replaced by fluorine, and
R1=R5-C(=O)— or $(C_1$-$C_6)$-alkyl-$SO_2$—;
R2=H, $(C_1$-$C_6)$-alkyl-, $(C_3$-$C_6)$-cycloalkyl-;
R3=H, $(C_1$-$C_4)$-alkyl-;
R4=H, $(C_1$-$C_4)$-alkyl-;
or wherein R3 and R4 together form a $(C_2$-$C_3)$-alkylene bridge;
R5=H, $(C_1$-$C_6)$-alkyl-, $(C_3$-$C_6)$-cycloalkyl-, $(C_1$-$C_6)$-alkyl-O—, $(C_1$-$C_6)$-alkyl-S—, $(C_1$-$C_6)$-alkyl-O—$(C_1$-$C_6)$-alkyl-, HO—$(C_1$-$C_6)$-alkyl-, $(C_3$-$C_6)$-cycloalkyl-$(C_1$-$C_6)$-alkyl-, $(C_6$-$C_{10})$-aryl-, $(C_6$-$C_{10})$-aryl-$(C_1$-$C_6)$-alkyl-, R7R6N—, heteroaryl, heteroaryl-$(C_1$-$C_6)$-alkyl-, aliphatic heterocycle,
  wherein one or more hydrogen atoms of the alkyl moieties may be replaced by fluorine, and wherein the aliphatic heterocycle is selected from the group of morpholinyl, piperidinyl, pyrrolidinyl and 4 to 7 membered aliphatic heterocycles comprising an oxygen atom, and wherein the aliphatic heterocycle may be optionally substituted with 1 to 3 substituents selected from the group of F, OH, $(C_1-C_6)$-alkyl-O— and $(C_1-C_6)$-alkyl-, and wherein the heteroaryl residues are five- or six-membered ring systems, comprising 1-3 heteroatoms selected from the group N, O and S, and wherein aryl and heteroaryl are optionally substituted with 1-3 rests selected independently from F, Cl, Br, $CF_3$, $(C_1-C_6)$-alkyl-, $(C_1-C_6)$-alkyl-O—, CN, $(C_1-C_2)$-alkyl-$SO_2$—;

R6=H, $(C_1-C_6)$-alkyl-, $(C_3-C_6)$-cycloalkyl-,
wherein one hydrogen atom of the alkyl group may be replaced by an OH— or $(C_1-C_6)$-alkyl-O— residue, and
wherein one or more hydrogen atoms of the alkyl group may be replaced by fluorine;

R7=H, $(C_1-C_6)$-alkyl-;
wherein one or more hydrogen atoms of the alkyl group may be replaced by fluorine, with the proviso if R5 is methyl and R2, R3 and R4 are equal to H and A is equal to 4-fluoro-phenyl, the residue X is not phenyl, 4-fluoro-phenyl, 4-chloro-phenyl, 4-methyl-phenyl, 4-methoxy-phenyl, 4-acetoxyphenyl, 2-chloro-phenyl, 3,4-dichlorophenyl, and with the proviso if R5 is methyl and R2, R3 and R4 are equal to H and X is a phenyl residue, the residue A is not phenyl, 4-fluoro-phenyl, 4-chloro-phenyl, 4-methyl-phenyl, 4-ethyloxy-phenyl or 3-trifluoromethyl-phenyl, and with the proviso if R5 is methyl and R2 is methyl and R3 and R4 are equal to H and A is equal to 4-fluoro-phenyl, the residue X is not phenyl.

Preferred compounds are, wherein

A=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—, R1=R5-C(=O)— or methyl-$SO_2$—;
R2=H, $(C_1-C_2)$-alkyl-, cyclopropyl-;
R3=H, methyl-;
R4=H, methyl-;
or wherein R3 and R4 together form an ethylene bridge; and wherein R5 is equal to a heteroaryl or heteroaryl-$(C_1-C_6)$-alkyl-,
wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and payrazin-3-yl, and
wherein these residues are optionally substituted with 1 or 2 residues selected independently from F, Cl, Br, $CF_3$, methyl, ethyl, methoxy, ethoxy, CN, methyl-$SO_2$—, or wherein
R5 is equal to H;

or wherein
R5 is equal to cyclopropyl, cyclobutyl, cyclopentyl, cyclohexyl or $(C_3-C_6)$-cycloalkyl-$(C_1-C_2)$-alkyl-, or wherein
R5 is equal to $(C_1-C_2)$-alkyl-O—, $(C_1-C_2)$-alkyl-S—, or wherein
R5 is equal to $(C_1-C_4)$-alkyl-O-methyl-, HO—$(C_1-C_2)$-alkyl-, or wherein
R5 is equal to phenyl- or phenylmethyl-,
wherein the phenyl residues are optionally substituted with 1-3 residues selected independently from F, Cl, Br, $CF_3$, $(C_1-C_2)$-alkyl-, $(C_1-C_2)$-alkyl-O—, CN, methyl-$SO_2$—, and
wherein one or more hydrogen atoms of the alkyl moieties may be replaced by fluorine;

or wherein
R5 is equal to R7R6N—, wherein
R6=H, $(C_1-C_4)$-alkyl-, cyclopropyl-, wherein one hydrogen atom of the alkyl group may be replaced by a hydroxy, methoxy or ethoxy residue and
R7=H, methyl-, ethylor wherein
R5 is equal to an aliphatic heterocycle,
wherein the aliphatic heterocycle is selected from the group of oxetanyl, tetrahydrofuranyl, tetrahydropyranyl, morpholinyl, piperidinyl, pyrrolidinyl, and
wherein the aliphatic heterocycle may be optionally substituted with 1 or 2 substituents selected from the group of F, OH, $(C_1-C_2)$-alkyl-O— and $(C_1-C_4)$-alkyl-, and
wherein one or more hydrogen atoms of the alkyl groups may be replaced by fluorine;

and/or of a stereoisomeric form of the compound of the formula I and/or mixtures of these forms, and/or their pharmaceutically acceptable salts.

Particularly preferred compounds are, wherein

A=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—, R1=R5-C(=O)—;
R2=H, $(C_1-C_2)$-alkyl-, cyclopropyl-;
R3=H, methyl-;
R4=H, methyl-;
or wherein R3 and R4 together form an ethylene bridge;
and wherein
R5 is equal to $(C_2-C_4)$-alkyl, and/or of a stereoisomeric form of the compound of the formula I and/or mixtures of these forms, and/or their pharmaceutically acceptable salts.

A further embodiment of the present invention are compounds of formula I, wherein A=$(C_6-C_{10})$-aryl or a five- or six-membered heteroaryl, comprising 1-3 heteroatoms selected from the group N, O and S,
wherein aryl and heteroaryl are optionally substituted with 1-3 rests selected independently from F, Cl, Br, CN, $(C_1-C_6)$-alkyl-, $(C_1-C_6)$-alkyl-O— and $(C_1-C_6)$-alkyl-S—,
wherein one or more hydrogen atoms of the alkyl moieties may be replaced by fluorine;

X=$(C_6-C_{10})$-aryl or a five- or six-membered heteroaryl, comprising 1-3 heteroatoms selected from the group N, O and S,
  wherein aryl and heteroaryl are optionally substituted with 1-3 rests selected independently from F, Cl, Br, CN, $(C_1-C_6)$-alkyl-, $(C_1-C_6)$-alkyl-O— and $(C_1-C_6)$-alkyl-S—, $(C_1-C_6)$-alkyl-O—C(O)— and $(C_1-C_6)$-alkyl-SO$_2$—,
    wherein one or more hydrogen atoms of the alkyl moieties may be replaced by fluorine;
R1=R5-C(=O)— or $(C_1-C_6)$-alkyl-SO$_2$—;
R2=H, $(C_1-C_6)$-alkyl-, $(C_3-C_6)$-cycloalkyl-;
R3=H, $(C_1-C_4)$-alkyl-;
R4=H, $(C_1-C_4)$-alkyl-;
or R3, R4 together form a $(C_2-C_3)$-alkylene bridge;
and wherein
R5 is equal to a heteroaryl or heteroaryl-$(C_1-C_6)$-alkyl-,
  wherein the heteroaryl residues are five- or six-membered ring systems, comprising 1-3 heteroatoms selected from the group N, O and S, and
    wherein the heteroaryl residues are optionally substituted with 1-3 residues selected independently from F, Cl, Br, CF$_3$, $(C_1-C_6)$-alkyl-, $(C_1-C_6)$-alkyl-O—, CN, $(C_1-C_2)$-alkyl-SO$_2$—,
      wherein one or more hydrogen atoms of the alkyl moieties may be replaced by fluorine,
    with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl,
  or wherein R5 is methyl,
    with the proviso if in compounds of formula I R2, R3 and R4 are hydrogen and X is a 2,4-difluorophenyl residue A is not pyridine-3-yl, 2-fluoro-phenyl, 3-fluoro-phenyl, 4-fluoro-phenyl, 3-cyano-phenyl, 3-methoxy-phenyl, 3-trifluormethoxy-phenyl, 2-fluoro-5-methoxy-phenyl, and
    with the proviso if in compounds of formula I R2, R3 and R4 are hydrogen and X is a 3-cyanophenyl residue A is not a 4-fluorophenyl residue, and
    with the proviso if in compounds of formula I R3 is methyl, R2 and R4 are hydrogen and X is a 2,4-difluoro-phenyl residue A is not a 4-fluoro-phenyl, and
    with the proviso if in compounds of formula I R2, R3 and R4 are hydrogen and X is phenyl A is not phenyl, 3-trifluoromethyl-phenyl, 4-fluoro-phenyl, 4-chloro-phenyl, 4-methyl-phenyl, 4-ethyloxy-phenyl, 4-methyl-thiophenyl, 2-thiophenyl, and
    with the proviso if in compounds of formula I R2, R3 and R4 are hydrogen and A is 4-fluoro-phenyl X is not phenyl, 2-chloro-phenyl, 3,4-dichloro-phenyl, 4-chloro-phenyl, 4-fluoro-phenyl, 4-methyl-phenyl, 4-methoxy-phenyl, 4-ethyloxy-phenyl, or 4-acetoxyphenyl, and
    with the proviso if R5 is methyl and R2 is methyl and R3 and R4 are equal to H and A is equal to 4-fluoro-phenyl, the residue X is not phenyl, and
  or wherein
R5 is equal to H, $(C_2-C_6)$-alkyl, CF$_3$, CF$_2$H, CFH$_2$,
    wherein one or more hydrogen atoms of the alkyl residue may be replaced by fluorine;
  or wherein
R5 is equal to $(C_3-C_6)$-cycloalkyl or $(C_3-C_6)$-cycloalkyl-$(C_1-C_4)$-alkyl-, with the proviso if in compounds of formula I A is a 3-cyanophenyl residue and X a 2,4-difluorophenyl residue R5 is not cyclopropyl,
  or wherein
R5 is equal to $(C_1-C_4)$-alkyl-O— or $(C_1-C_4)$-alkyl-S—,
    wherein one or more hydrogen atoms of the alkyl moieties may be replaced by fluorine;
  or wherein
R5 is equal to $(C_1-C_4)$-alkyl-O—$(C_1-C_2)$-alkyl-, HO—$(C_1-C_4)$-alkyl-,
  or wherein
R5 is equal to phenyl-, phenyl-$(C_1-C_4)$-alkyl-,
    wherein the phenyl residues are optionally substituted with 1-3 residues selected independently from F, Cl, Br, CF$_3$, $(C_1-C_6)$-alkyl-, $(C_1-C_6)$-alkyl-O—, CN, $(C_1-C_2)$-alkyl-SO$_2$—, and
      wherein one or more hydrogen atoms of the alkyl moieties may be replaced by fluorine,
    with the proviso if in compounds of formula I A is a 3-cyanophenyl residue and X a 2,4-difluorophenyl residue R5 is not 3-methylsulfonyl-phenyl, 4-methylsulfonyl-phenyl;
  or wherein
R5 is equal to R7R6N—, wherein
  R6=H, $(C_1-C_4)$-alkyl-, cyclopropyl-, wherein one hydrogen atom of the alkyl group may be replaced by an OH, methoxy or ethoxy residue and
  R7=H, $(C_1-C_2)$-alkyl-,
  or wherein
R5 is equal to an aliphatic heterocycle,
    wherein the aliphatic heterocycle is selected from the group of oxetanyl, tetrahydrofuranyl, tetrahydropyranyl, morpholinyl, piperidinyl, pyrrolidinyl, and
    wherein the aliphatic heterocycle may be optionally substituted with 1 or 2 substituents selected from the group of F, OH, $(C_1-C_4)$-alkyl-O— and $(C_1-C_4)$-alkyl-, and
    wherein one or more hydrogen atoms of the alkyl groups may be replaced by fluorine,
    with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl.
Preferred compounds are, wherein
A=phenyl, pyridine-2-yl, pyridine-3-yl, pyridine-4-yl, thiophen-2-yl or thiophen-3-yl,
  wherein these residues are optionally substituted with 1 or 2 residues selected independently from F, Cl, Br, CN, $(C_1-C_4)$-alkyl-, CF$_3$, CF$_2$H, CFH$_2$, methoxy, ethoxy, OCF$_3$ and $(C_1-C_2)$-alkyl-S—;
X=phenyl,
  wherein the phenyl residue is substituted with 1 or 2 residues selected independently from F, Cl, Br, CN, $(C_1-C_4)$-alkyl-, CF$_3$, CF$_2$H, CFH$_2$, methoxy, ethoxy, OCF$_3$, $(C_1-C_2)$-alkyl-S—, $(C_1-C_2)$-alkyl-O—C(O)— and methyl-SO$_2$—,
  or
  pyridine-2-yl, pyridine-3-yl, pyridine-4-yl, thiophen-2-yl, thiophen-3-yl, thiazol-2-yl, thiazol-4-yl, thiazol-5-yl,
    wherein these residues are optionally substituted with 1 or 2 residues selected independently from F, Cl, Br, CN, $(C_1-C_4)$-alkyl-, CF$_3$, CF$_2$H, CFH$_2$, methoxy, ethoxy, OCF$_3$, $(C_1-C_2)$-alkyl-S—, $(C_1-C_2)$-alkyl-O—C(O)— and methyl-SO$_2$—;
R1=R5-C(=O)— or $(C_1-C_2)$-alkyl-SO$_2$—;
R2=H, $(C_1-C_2)$-alkyl-, cyclopropyl-;
R3=H, $(C_1-C_2)$-alkyl-;
R4=H, $(C_1-C_2)$-alkyl-;
or wherein R3 and R4 together form an ethylene bridge;
and wherein
R5 is equal to a heteroaryl or heteroaryl-$(C_1-C_6)$-alkyl-,
  wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and payrazin-3-yl, and wherein these residues are optionally substituted with 1 or 2 residues selected independently from F, Cl, Br, $CF_3$, methyl, ethyl, methoxy, ethoxy, CN, methyl-$SO_2$—, with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl, or wherein R5 is methyl, with the proviso if in compounds of formula I R2, R3 and R4 are hydrogen and X is a 2,4-difluorophenyl residue A is not pyridine-3-yl, 2-fluoro-phenyl, 3-fluoro-phenyl, 4-fluorophenyl, 3-cyano-phenyl, 3-methoxy-phenyl, 3-trifluormethoxy-phenyl, 2-fluoro-5-methoxy-phenyl, and with the proviso if in compounds of formula I R2, R3 and R4 are hydrogen and X is a 3-cyanophenyl residue A is not a 4-fluorophenyl residue, and with the proviso if in compounds of formula I R3 is methyl, R2 and R4 are hydrogen and X is a 2,4-difluoro-phenyl residue A is not a 4-fluoro-phenyl, and with the proviso if in compounds of formula I R2, R3 and R4 are hydrogen and X is phenyl A is not phenyl, 3-trifluoromethyl-phenyl, 4-fluoro-phenyl, 4-chloro-phenyl, 4-methyl-phenyl, 4-ethoxy-phenyl, 2-thiophenyl, 4-methylthiophenyl, and with the proviso if in compounds of formula I R2, R3 and R4 are hydrogen and A is 4-fluoro-phenyl X is not 2-chloro-phenyl, 3,4-dichloro-phenyl, 4-chloro-phenyl, 4-fluoro-phenyl, 4-methyl-phenyl, 4-methoxy-phenyl, 4-acetoxyphenyl or 4-ethoxy-phenyl, and or wherein R5 is equal to H, $(C_2-C_4)$-alkyl, $CF_3$;

or wherein

R5 is equal to cyclopropyl, cyclobutyl, cyclopentyl, cyclohexyl or $(C_3-C_6)$-cycloalkyl-$(C_1-C_2)$-alkyl-, with the proviso if in compounds of formula I A is a 3-cyanophenyl residue and X a 2,4-difluorophenyl residue R5 is not cyclopropyl, or wherein R5 is equal to $(C_1-C_2)$-alkyl-O— or $(C_1-C_2)$-alkyl-S—, wherein one or more hydrogen atoms of the alkyl moieties may be replaced by fluorine;

or wherein

R5 is equal to $(C_1-C_4)$-alkyl-O-methyl-, HO—$(C_1-C_2)$-alkyl-, wherein one or more hydrogen atoms of the alkyl moieties may be replaced by fluorine;

or wherein

R5 is equal to phenyl-, phenyl-$(C_1-C_2)$-alkyl-, wherein the phenyl residues are optionally substituted with 1-3 residues selected independently from F, Cl, Br, $CF_3$, $(C_1-C_2)$-alkyl-, $(C_1-C_2)$-alkyl-O—, CN, methyl-$SO_2$—, and wherein one or more hydrogen atoms of the alkyl moieties may be replaced by fluorine, with the proviso if in compounds of formula I A is a 3-cyanophenyl residue and X a 2,4-difluorophenyl residue R5 is not 3-methylsulfonyl-phenyl, 4-methylsulfonyl-phenyl;

or wherein

R5 is equal to R7R6N—, wherein

R6=H, $(C_1-C_4)$-alkyl-, cyclopropyl-, wherein one hydrogen atom of the alkyl group may be replaced by a hydroxy, methoxy or ethoxy residue and R7=H, methyl-, ethylor wherein R5 is equal to an aliphatic heterocycle, wherein the aliphatic heterocycle is selected from the group of oxetanyl, tetrahydrofuranyl, tetrahydropyranyl, morpholinyl, piperidinyl, pyrrolidinyl, and wherein the aliphatic heterocycle may be optionally substituted with 1 or 2 substituents selected from the group of F, OH, $(C_1-C_2)$-alkyl-O— and $(C_1-C_4)$-alkyl-, and wherein one or more hydrogen atoms of the alkyl groups may be replaced by fluorine, with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl.

and/or of a stereoisomeric form of the compound of the formula I and/or mixtures of these forms, and/or their pharmaceutically acceptable salts.

Further preferred compounds are, wherein

A is equal to phenyl, wherein the phenyl residue is optionally substituted with 1-3 residues selected independently from F, Cl, Br, CN, $(C_1-C_4)$-alkyl-, $(C_1-C_4)$-alkyl-O— and $(C_1-C_4)$-alkyl-S—, wherein one or more hydrogen atoms of the alkyl moieties may be replaced by fluorine, and X is equal to phenyl, wherein the phenyl group is optionally substituted with 1, 2 or 3 residues selected independently from F, Cl, Br, CN, $(C_1-C_4)$-alkyl-, $(C_1-C_4)$-alkyl-O—, $(C_1-C_4)$-alkyl-S—, $(C_1-C_4)$-alkyl-O—C(O)— and $(C_1-C_4)$-alkyl-$SO_2$—, wherein one or more hydrogen atoms of the alkyl moieties may be replaced by fluorine, and R1=R5-C(=O)— or $(C_1-C_6)$-alkyl-$SO_2$—;

R2=H, $(C_1-C_6)$-alkyl-, $(C_3-C_6)$-cycloalkyl-;

R3=H, $(C_1-C_4)$-alkyl-;

R4=H, $(C_1-C_4)$-alkyl-;

or wherein R3 and R4 together form a $(C_2-C_3)$-alkylene bridge; and wherein

R5 is equal to a heteroaryl or heteroaryl-$(C_1-C_6)$-alkyl-, wherein the heteroaryl residues are five- or six-membered ring systems, comprising 1-3 heteroatoms selected from the group N, O and S, and wherein the heteroaryl residues are optionally substituted with 1-3 residues selected independently from F, Cl, Br, $CF_3$, $(C_1-C_6)$-alkyl-, $(C_1-C_6)$-alkyl-O—, CN, $(C_1-C_2)$-alkyl-$SO_2$—, wherein one or more hydrogen atoms of the alkyl moieties may be replaced by fluorine, with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl, or wherein R5 is methyl, with the proviso if in compounds of formula I R2, R3 and R4 are hydrogen and X is a 2,4-difluorophenyl residue A is not pyridine-3-yl, 2-fluoro-phenyl, 3-fluoro-phenyl, 4-fluorophenyl, 3-cyano-phenyl, 3-methoxy-phenyl, 3-trifluormethoxy-phenyl, 2-fluoro-5-methoxy-phenyl, and

17 with the proviso if in compounds of formula I R2, R3 and R4 are hydrogen and X is a 3-cyanophenyl residue A is not a 4-fluorophenyl residue, and with the proviso if in compounds of formula I R3 is methyl, R2 and R4 are hydrogen and X is a 2,4-difluoro-phenyl residue A is not a 4-fluoro-phenyl, and with the proviso if in compounds of formula I R2, R3 and R4 are hydrogen and X is phenyl A is not phenyl, 3-trifluoromethyl-phenyl, 4-fluoro-phenyl, 4-chloro-phenyl, 4-methyl-phenyl, 4-ethyloxy-phenyl, 4-methyl-thiophenyl, 2-thiophenyl, and with the proviso if in compounds of formula I R2, R3 and R4 are hydrogen and A is 4-fluoro-phenyl X is not phenyl, 2-chloro-phenyl, 3,4-dichloro-phenyl, 4-chloro-phenyl, 4-fluoro-phenyl, 4-methyl-phenyl, 4-methoxy-phenyl, 4-ethyloxy-phenyl, or 4-acetoxyphenyl, and with the proviso if in compounds of formula I R2 is methyl, R3 and R4 are hydrogen and A is 4-fluoro-phenyl, the residue X is not phenyl, and or wherein R5 is equal to H, $(C_2-C_6)$-alkyl, $CF_3$, $CF_2H$, $CFH_2$,
wherein one or more hydrogen atoms of the alkyl residue may be replaced by fluorine;

or wherein

R5 is equal to $(C_3-C_6)$-cycloalkyl or $(C_3-C_6)$-cycloalkyl-$(C_1-C_4)$-alkyl-,
with the proviso if in compounds of formula I A is a 3-cyanophenyl residue and X a 2,4-difluorophenyl residue R5 is not cyclopropyl, or wherein R5 is equal to $(C_1-C_4)$-alkyl-O— or $(C_1-C_4)$-alkyl-S—,
wherein one or more hydrogen atoms of the alkyl moieties may be replaced by fluorine;

or wherein

R5 is equal to $(C_1-C_4)$-alkyl-O—$(C_1-C_2)$-alkyl-, HO—$(C_1-C_4)$-alkyl-, or wherein R5 is equal to phenyl-, phenyl-$(C_1-C_4)$-alkyl-,
wherein the phenyl residues are optionally substituted with 1-3 residues selected independently from F, Cl, Br, $CF_3$, $(C_1-C_6)$-alkyl-, $(C_1-C_6)$-alkyl-O—, CN, $(C_1-C_2)$-alkyl-$SO_2$—, and
wherein one or more hydrogen atoms of the alkyl moieties may be replaced by fluorine,
with the proviso if in compounds of formula I A is a 3-cyanophenyl residue and X a 2,4-difluorophenyl residue R5 is not 3-methylsulfonyl-phenyl, 4-methylsulfonyl-phenyl;

or wherein

R5 is equal to R7R6N—, wherein
R6=H, $(C_1-C_4)$-alkyl-, cyclopropyl-, wherein one hydrogen atom of the alkyl group may be replaced by an OH, methoxy or ethoxy residue and
R7=H, $(C_1-C_2)$-alkyl-, or wherein R5 is equal to an aliphatic heterocycle,
wherein the aliphatic heterocycle is selected from the group of oxetanyl, tetrahydrofuranyl, tetrahydropyranyl, morpholinyl, piperidinyl, pyrrolidinyl, and
wherein the aliphatic heterocycle may be optionally substituted with 1 or 2 substituents selected from the group of F, OH, $(C_1-C_4)$-alkyl-O— and $(C_1-C_4)$-alkyl-, and
wherein one or more hydrogen atoms of the alkyl groups may be replaced by fluorine,
with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl.

R6=H, $(C_1-C_6)$-alkyl-, $(C_3-C_6)$-cycloalkyl-,
wherein one hydrogen atom of the alkyl group may be replaced by an OH— or $(C_1-C_6)$-alkyl-O— residue, and
wherein one or more hydrogen atoms of the alkyl group may be replaced by fluorine;

R7=H, $(C_1-C_6)$-alkyl-;
wherein one or more hydrogen atoms of the alkyl group may be replaced by fluorine.

Particularly preferred compounds are compounds of formula I, wherein

A=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—, R1=R5-C(=O)— or methyl-$SO_2$—;
R2=H, $(C_1-C_2)$-alkyl-, cyclopropyl-;
R3=H, methyl-;
R4=H, methyl-;
or wherein R3 and R4 together form an ethylene bridge;
and wherein R5 is equal to a heteroaryl or heteroaryl-$(C_1-C_6)$-alkyl-,
wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and payrazin-3-yl, and
wherein these residues are optionally substituted with 1 or 2 residues selected independently from F, Cl, Br, $CF_3$, methyl, ethyl, methoxy, ethoxy, CN, methyl-$SO_2$—,
with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl, or wherein R5 is methyl,
with the proviso if in compounds of formula I R2, R3 and R4 are hydrogen and X is a 2,4-difluorophenyl residue A is not pyridine-3-yl, 2-fluoro-phenyl, 3-fluoro-phenyl, 4-fluorophenyl, 3-cyano-phenyl, 3-methoxy-phenyl, 3-trifluormethoxy-phenyl, 2-fluoro-5-methoxy-phenyl, and with the proviso if in compounds of formula I R2, R3 and R4 are hydrogen and X is a 3-cyanophenyl residue A is not a 4-fluorophenyl residue, and with the proviso if in compounds of formula I R3 is methyl, R2 and R4 are hydrogen and X is a 2,4-difluoro-phenyl residue A is not a 4-fluoro-phenyl, and with the proviso if in compounds of formula I R2, R3 and R4 are hydrogen and X is phenyl A is not phenyl, 3-trifluoromethyl-phenyl, 4-fluoro-phenyl, 4-chloro-phenyl, 4-methyl-phenyl, 4-ethoxy-phenyl, 2-thiophenyl, 4-methylthiophenyl, and with the proviso if in compounds of formula I R2, R3 and R4 are hydrogen and A is 4-fluoro-phenyl X is not 2-chloro-phenyl, 3,4-dichloro-phenyl, 4-chloro-phenyl, 4-fluoro-phenyl, 4-methyl-phenyl, 4-methoxy-phenyl, 4-ethoxy-phenyl or 4-acetoxyphenyl, and
with the proviso if in compounds of formula I R2 is methyl, R3 and R4 are hydrogen and A is 4-fluoro-phenyl, the residue X is not phenyl, and
or wherein
R5 is equal to H, $(C_2-C_4)$-alkyl, $CF_3$;
or wherein
R5 is equal to cyclopropyl, cyclobutyl, cyclopentyl, cyclohexyl or $(C_3-C_6)$-cycloalkyl-$(C_1-C_2)$-alkyl-,
with the proviso if in compounds of formula I A is a 3-cyanophenyl residue and X a 2,4-difluorophenyl residue R5 is not cyclopropyl,
or wherein
R5 is equal to $(C_1-C_2)$-alkyl-O— or $(C_1-C_2)$-alkyl-S—,
wherein one or more hydrogen atoms of the alkyl moieties may be replaced by fluorine;
or wherein
R5 is equal to $(C_1-C_4)$-alkyl-O-methyl-, HO—$(C_1-C_2)$-alkyl-,
wherein one or more hydrogen atoms of the alkyl moieties may be replaced by fluorine;
or wherein
R5 is equal to phenyl-, phenyl-$(C_1-C_2)$-alkyl-,
wherein the phenyl residues are optionally substituted with 1-3 residues selected independently from F, Cl, Br, $CF_3$, $(C_1-C_2)$-alkyl-, $(C_1-C_2)$-alkyl-O—, CN, methyl-$SO_2$—, and
wherein one or more hydrogen atoms of the alkyl moieties may be replaced by fluorine,
with the proviso if in compounds of formula I A is a 3-cyanophenyl residue and X a 2,4-difluorophenyl residue R5 is not 3-methylsulfonyl-phenyl, 4-methylsulfonyl-phenyl;
or wherein
R5 is equal to R7R6N—, wherein
R6=H, $(C_1-C_4)$-alkyl-, cyclopropyl-, wherein one hydrogen atom of the alkyl group may be replaced by a hydroxy, methoxy or ethoxy residue and
R7=H, methyl-, ethyl-
or wherein
R5 is equal to an aliphatic heterocycle,
wherein the aliphatic heterocycle is selected from the group of oxetanyl, tetrahydrofuranyl, tetrahydropyranyl, morpholinyl, piperidinyl, pyrrolidinyl, and
wherein the aliphatic heterocycle may be optionally substituted with 1 or 2 substituents selected from the group of F, OH, $(C_1-C_2)$-alkyl-O— and $(C_1-C_4)$-alkyl-, and
wherein one or more hydrogen atoms of the alkyl groups may be replaced by fluorine,
with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl,
and/or of a stereoisomeric form of the compound of the formula I and/or mixtures of these forms, and/or their pharmaceutically acceptable salts.

Further preferred compounds suitable as TASK-1 inhibitors are compounds of formula I, wherein
A=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;
X=phenyl,
wherein the phenyl residue is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—,
R1=R5-C(=O)—;
R2=H, $(C_1-C_2)$-alkyl-, cyclopropyl-;
R3=H, methyl-;
R4=H, methyl-;
or wherein R3 and R4 together form an ethylene bridge;
and wherein
R5 is equal to $(C_2-C_4)$-alkyl;
and/or of a stereoisomeric form of the compound of the formula I and/or mixtures of these forms, and/or their pharmaceutically acceptable salts.

Alkyl radicals have between 1 and 6, preferably between 1 and 4 carbon atoms and may be straight-chain or branched. Alkyl radicals may also be straight-chain or branched if they are substituted or are present in other radicals, for example in an alkyloxy radical (alkoxy radical) or in a fluorinated alkyl radical. Examples of alkyl radicals are methyl, ethyl, n-propyl, isopropyl, n-butyl, isobutyl, sec-butyl and tert-butyl. One or more, for example 1, 2, 3, 4, 5, 6, 7, 8, or 9 hydrogen atoms in alkyl radicals may be replaced by fluorine atoms. Preferred fluorinated alkyl radicals are $CF_3$, $CF_2H$ and $CFH_2$. Substituted alkyl radicals may be substituted in any positions. Preferred alkyloxy radicals are methoxy and ethoxy. These explanations with respect to alkyl radicals apply correspondingly to alkyl radicals which in the definition of a group in the compounds of the formula I are bonded to two adjacent groups, or linked to two groups, and may be regarded as divalent alkyl radicals (alkanediyl radicals, alkylene radicals), like in the case of the alkyl part of a substituted alkyl group, for example the group $(C_1-C_6)$-alkyloxy-$(C_1-C_6)$-alkyl- or the group heteroaryl-$(C_1-C_6)$-alkyl-, in which groups and likewise in other groups the terminal hyphen denotes the free bond via which the group is bonded, and thus indicates via which subgroup a group composed of subgroups is bonded. Thus, such radicals can also be straight-chain or branched, the bonds to the adjacent groups can be located in any positions and can start from the same carbon atom or from different carbon atoms, and they can be unsubstituted or substituted by fluorine substituents independently of any other substituents. Examples of such divalent alkyl radicals are methylene, 1,1-ethylene, 1,2-ethylene, 1,1-propylene, 1,2-propylene, 2,2-propylene, 1,3-propylene, 1,1-butylene, 1,4-butylene, etc.

Examples of cycloalkyl radicals having 3 to 6 C atoms are cyclopropyl, cyclobutyl, 1-methylcyclopropyl-, 2-methylcyclopropyl-, cyclobutyl, 2-methylcyclobutyl-, 3-methylcyclobutyl-, cyclopentyl, 2-methylcyclopentyl-, 3-methylcyclopentyl-, cyclohexyl etc.

Preferred heteroaryl residues are five or six-membered rings, comprising 1 to 3 heteroatoms selected from the group N, O and S, wherein a heteroaryl ring preferably comprise only one O or S atom. Preferred heteroaryl groups are 2-thiophenyl, 3-thiophenyl, 2-pyrimidinyl, 4-pyrimidinyl, 5-pyrimidinyl, 2-pyrazinyl, 3-pyridazinyl, 4-pyridazinyl, 3-pyrazolyl, 4-pyrazolyl, 2-imidazolyl, 4-imidazolyl, 2-thiazolyl, 4-thiazolyl, 5-thiazolyl, 3-isothiazolyl, 4-isothiazolyl, 5-isothiazolyl, wherein particularly preferred are 2-pyridyl, 3-pyridyl and 4-pyridyl.

Preferred heteroaryl residues for the group A are unsubstituted or substituted pyridine-2-yl, pyridine-3-yl, pyridine-4-yl, thiophen-2-yl and thiophen-3-yl, particularly preferred are substituted heteroaryl residues.

Preferred heteroaryl residues for the group X are unsubstituted or substituted pyridine-2-yl, pyridine-3-yl, pyridine-4-yl, thiophen-2-yl, thiophen-3-yl, thiazol-2-yl, thiazol-4-yl and thiazol-5-yl, particularly preferred are substituted heteroaryl residues.

Preferred heteroaryl residues for R5 are unsubstituted or substituted pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and payrazin-3-yl.

The heteroaryl residues may unsubstituted or substituted with one or two substituents. Preferred substituents of the heteroaryl residues are F, Cl, Br, methoxy, ethoxy, methyl, ethyl, NC—, $CF_3O$—, $CF_3$.

A preferred aryl residue is phenyl, wherein one or two hydrogen may be replaced by substituents, preferably selected from the group F, Cl, methoxy, ethoxy, methyl, ethyl, NC—, $CF_3O$—, $CF_3$, $CH_3$—$SO_2$—.

Preferred aliphatic heterocycle are selected from the group of morpholinyl, piperidinyl, pyrrolidinyl, oxetanyl and tetrahydrofuranyl and tetrahydropyranyl, wherein these aliphatic heterocycle may be optionally substituted with 1 or 2 substituents preferably selected independently from the group of F, OH, methoxy, ethoxy, methyl and ethyl.

If a radical is disubstituted or trisubstituted, the substituents may be identical or different.

If the compounds of the formula I comprise one or more basic groups or one or more basic heterocycles, the invention also includes the corresponding physiologically acceptable salts including trifluoroacetates, in particular the pharmaceutically acceptable salts. Thus, the compounds of the formula I which have one or more basic, i.e. protonatable, groups or comprise one or more basic heterocyclic rings, can also be used in the form of their physiologically tolerated acid addition salts with inorganic or organic acids, for example as hydrochlorides, phosphates, sulfates, methanesulfonates, acetates, lactates, maleates, fumarates, malates, gluconates etc. Salts can be obtained from compounds of the formula I by conventional processes, for example by combining with an acid in a solvent or dispersant or else by anion exchange from other salts. The compounds of the formula I may also be deprotonated on an acidic group and be used for example as alkali metal salts, preferably sodium or potassium salts, or as ammonium salts, for example as salts with ammonia or organic amines or amino acids.

The compounds of the formula I may exist in stereoisomeric forms. The centers of asymmetry which are present may independently of one another have the S configuration or the R configuration. The invention includes all possible stereoisomers, for example enantiomers or diastereomers, and mixtures of two or more stereoisomeric forms, for example enantiomers and/or diastereomers, in any ratios. The invention thus includes for example enantiomers in enantiopure form, both as levorotatory and as dextrorotatory antipodes, and in the form of mixtures of the two enantiomers in various ratios or in the form of racemates. Individual stereoisomers can be prepared as desired by fractionating a mixture by conventional methods or for example by stereoselective synthesis.

For the preparation of the compounds of formula I the following methods can be used.

In the described various chemical processes, the residues A, X, R1, R2, R3, R4, R5, R6 and R7 have the same meaning as in compounds of the formula I, provided that no specific definition of the respective residue is mentioned.

The preparation of diverse 4,5,6,7-Tetrahydro-1H-pyrazolo[4,3-c]pyridine intermediates can be done according to Scheme 1 (method A) following a previously described synthesis (EP 0 086 422 A2). The synthesis is applicable to a large variety of different groups A. Thus, starting from commercially available 1-acetyl-4-piperidone 1-(4-Morpholin-4-yl-3,6-dihydro-2H-pyridin-1-yl)-ethanone (enamine 1) is obtained. Thus, morpholine is added to a solution of 1-acetyl-4-piperidone in the presence of p-toluenesulfonic acid monohydrate (catalytic PTSA). After acylation with commercially available acyl chlorides, followed by acidic aqueous hydrolysis the diketones 2 are obtained and can be subjected to ring-closure with hydrazine hydrate to give the corresponding diverse 4,5,6,7-Tetrahydro-1H-pyrazolo[4,3-c]pyridine intermediates 3.

Scheme 1

Method A

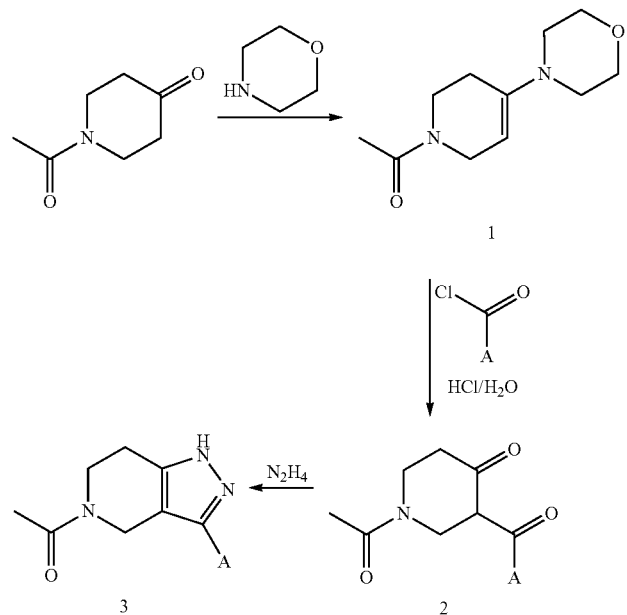

Method B

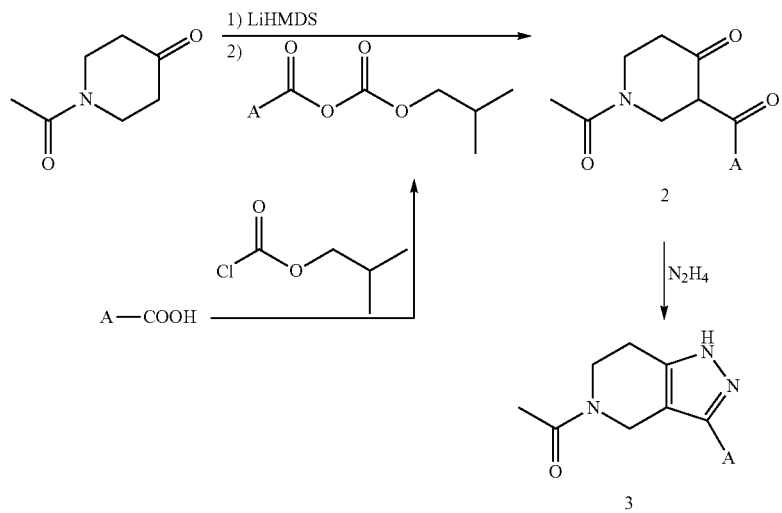

The acyl chlorides can alternatively be prepared by standard procedures from the corresponding acids e.g. by reaction with thionyl chloride in the presence of catalytic amounts of DMF (see for example Dalisay, D. S.; Quach, T.; Nicholas, G. N.; Molinski, T. F., Angewandte Chemie, International Edition, 2009, vol. 48, 4367-4371). If A is a heteroaryl than sometimes an alternative synthesis is preferable and can be used as shown in Scheme 1 (method B). Thus starting from commercially available acids the mixed anhydrides are formed by reaction with isobutylchloroformate. 1-Acetyl-4-piperidone 1-(4-Morpholin-4-yl-3,6-dihydro-2H-pyridin-1-yl)-ethanone can be deprotonated with strong bases like lithium hexamethyldisilazide and reacted with the mixed anhydride described above. The diketones 2 are obtained and can be subjected to ring-closure with hydrazine hydrate to give the corresponding diverse 4,5,6,7-Tetrahydro-1H-pyrazolo[4,3-c]pyridine intermediates 3.

R3, R4 substituted intermediates 5 can be accorded similarly as shown in Scheme 2. Thus after acetylation of commercially available or known piperidones N-Acetyl-piperidones 4 are obtained. They can be deprotonated with strong bases like lithium diisopropylamide (LDA) and reacted with mixed anhydrides formed by reaction of aryl or heteroarylcarbonic acids and isobutylchloroformate as described above. The diketones obtained can be subjected to ring-closure with hydrazine hydrate to give the corresponding R3, R4 substituted 4,5,6,7-Tetrahydro-1H-pyrazolo[4,3-c]pyridine intermediates 5.

4,5,6,7-Tetrahydro-1H-pyrazolo[4,3-c]pyridine intermediates can be successfully alkylated with a range of different aryl- and heteroaryl halogenides by heating in the presence of an excess amount of a base like $K_2CO_3$ in an inert solvent like $CH_3CN$ as shown in Scheme 3. The corresponding substituted 4,5,6,7-Tetrahydro-1H-pyrazolo[4,3-c]pyridine intermediates 6 were found to be TASK-1 blockers.

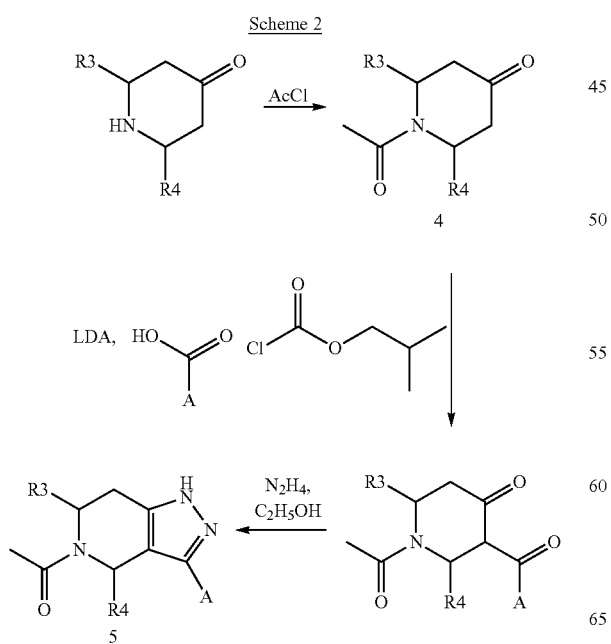

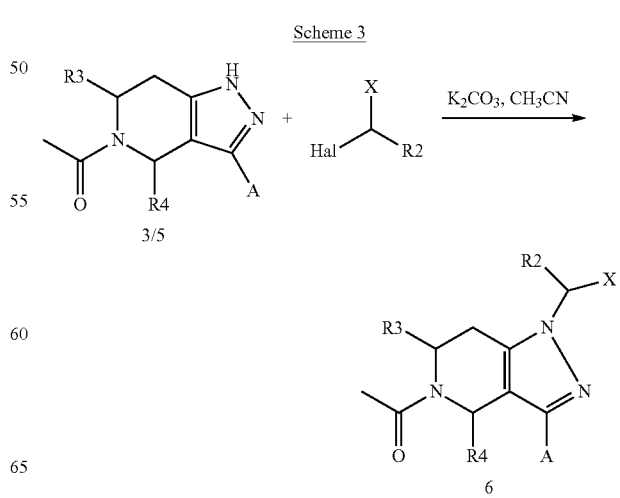

Scheme 4

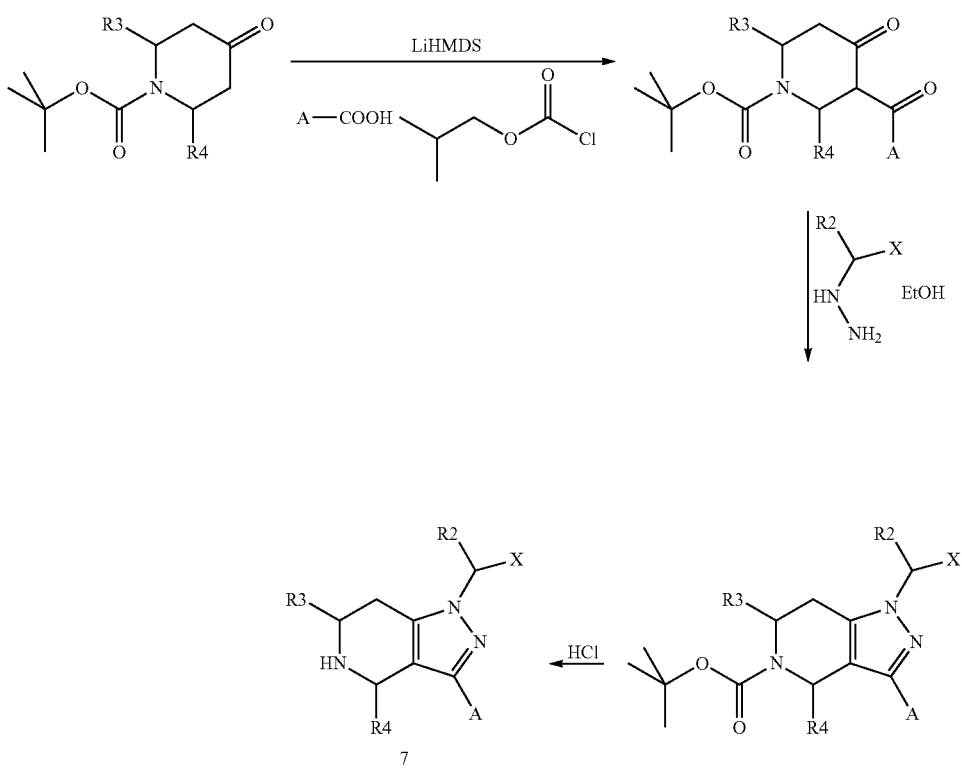

In a different approach (Scheme 4), starting from Boc-protected piperidones, the diketones obtained after deprotonation by a strong base like lithium diisopropylamide and reaction with diverse acyl chlorides can be reacted with substituted benzylhydrazines and subsequently deprotected to give compounds 7 which are intermediates in the synthesis of TASK-1 blockers.

The group R1 of compounds of formula I can be varied synthetically as shown in Scheme 5. The N-acetyl group can be cleaved by heating an acidic aqueous solution of compounds 6, for example in a mixture of ethanol and 2N aqueous HCl. The corresponding amines 7 can be modified in a variety of ways, for example by acylation as shown in Scheme 6. This can be done by several methods: for example by reaction with carboxylic acids in the presence of 1-hydroxybenzotriazole and EDC (1-ethyl-3-(3-dimethylaminopropyl)carbodiimide hydrochloride) (Nozaki, S. J. Peptide Res. 1999, 54, 162) (method A) or TOTU (O-[(Ethoxycarbonyl)cyanomethylenamino]-N,N,N',N-tetramethyluronium tetrafluoroborate) (Knorr, R. et al. Tetrahedron Lett. 1989, 30, 1927) (method D), by reaction with acyl chlorides or alkyl chloroformates in the presence of $K_2CO_3$ in $CH_3CN$ (method B), in a "Schotten-Baumann" reaction type by reaction with acyl chlorides in a water-ethyl acetate mixture in the presence of $NaHCO_3$ (method C), by reaction with acyl chlorides in the presence of triethylamine in $CH_2Cl_2$ (method E), or by reaction with acetic anhydride in pyridine (method F). The group R5 may carry protecting groups which can be cleaved off by methods known in the prior art. For example a hydroxyl group in R5 can be protected as a tert-butylether which can be cleaved off by an acid like HCl to give deprotected compounds 14 (Scheme 11). Of course the reaction is broadly applicable and not limited to the exact structure shown in Scheme 11.

Scheme 5

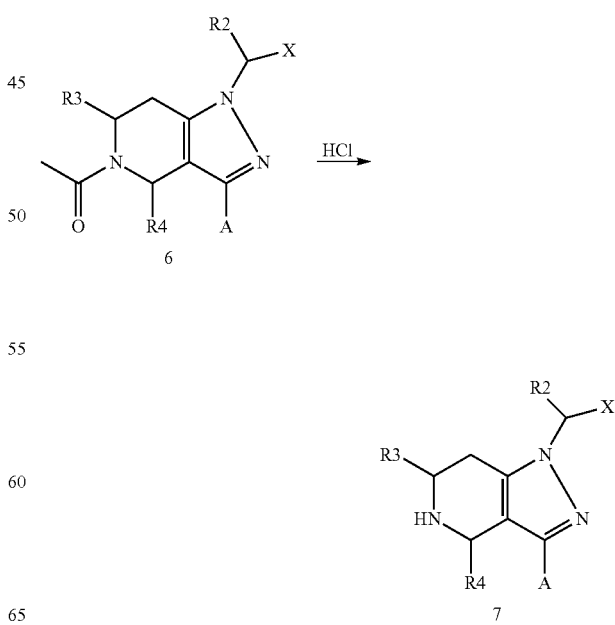

Scheme 6

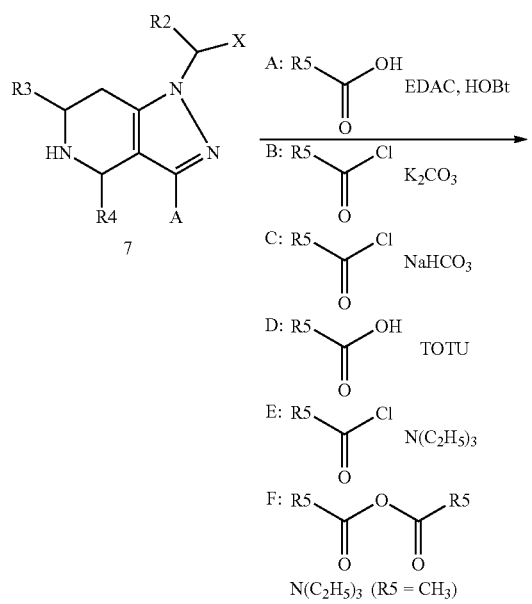

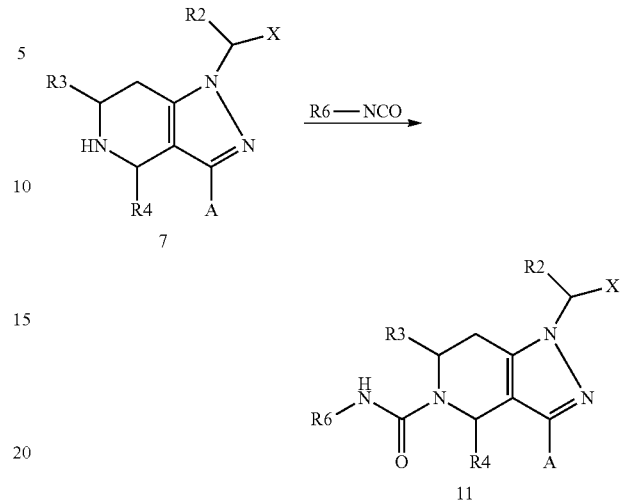

Scheme 7

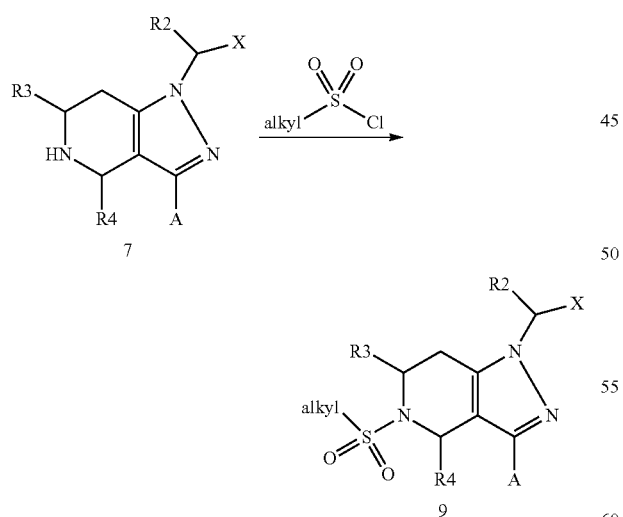

Alternatively TASK-1 blockers 8 can be obtained by sulfonylation with alkylsulfonyl halogenides (($C_1$-$C_6$)-alkyl-$SO_2$—) in inert solvents like $CH_2Cl_2$ in the presence of a base like triethylamine as shown in Scheme 7.

In another reaction (Scheme 8), reaction of intermediates 7 with diverse isocyanates in an inert solvent for example $CH_2Cl_2$ leads to formation of ureas 11 which have been found to be TASK-1 blockers.

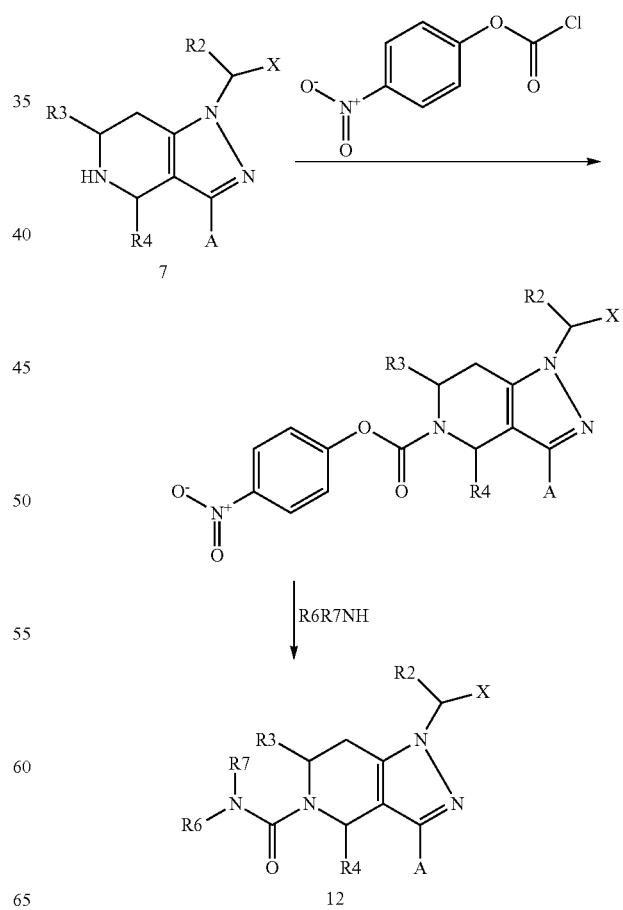

In another reaction (Scheme 9), reaction of intermediates 7 with 4-nitrophenylchloroformate leads to intermediates with can be reacted with diverse amines to give ureas 12 which have been found to be TASK-1 blockers and are novel compounds not described before.

Scheme 10

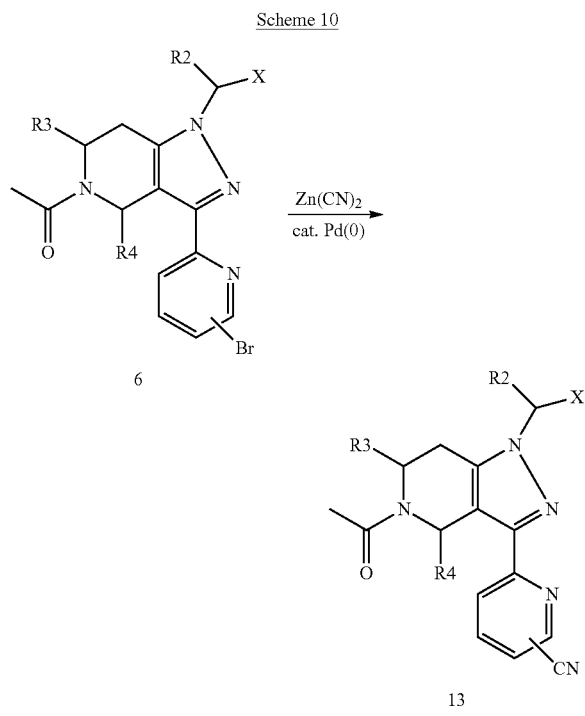

The aryl or heteroaryl ring A can be modified when substituted by a bromide to give the corresponding nitriles as shown in Scheme 10 by reaction with Zn(CN)$_2$ in the presence of a catalytic amount of tetrakis(triphenylphosphine)palladium (0) (in analogy to Alterman, M.; Anders, H. Journal of Organic Chemistry, 2000, vol. 65, 23 p. 7984-7989). The reaction is not limited to pyridines as drawn in Scheme 10 but is applicable to a range of aryl and heteroaryl systems. The novel compounds 13 which have not been previously described have been found to be TASK-1 blockers.

Scheme 11

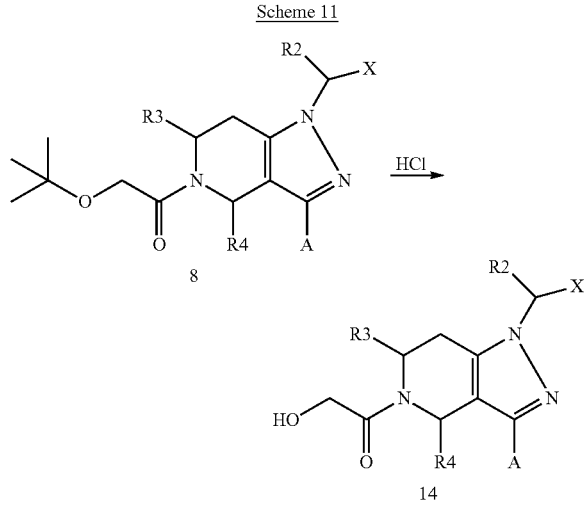

A tert-butylether 8 can be cleaved off by an acid like HCl to give deprotected compounds 14 (Scheme 11). The reaction is broadly applicable and not limited to the exact structure shown in Scheme 11.

The working up and, if desired, the purification of the products and/or intermediates takes place by conventional methods such as extraction, chromatography or crystallization and conventional dryings.

Owing to the TASK-1-inhibitory properties, the compounds of the formula I and/or their pharmaceutically compatible salts are suitable for the prevention and treatment of disorders which are caused by activation or by an activated TASK-1, and also of disorders in which have TASK-1-related damages appear secondary to another, primary cause.

The compounds of the formula I, and/or physiologically compatible salts thereof can also be used for the treatment and prevention of disorders where TASK-1 requires only partial inhibition, for example by using a lower dosage, wherein for the treatment and prevention of disorders described below the compounds of formula I includes compounds wherein R5 is methyl and R2, R3 and R4 are equal to H and A is equal to 4-fluoro-phenyl, and the residue X is phenyl, 4-fluoro-phenyl, 4-chloro-phenyl, 4-methyl-phenyl, 4-methoxy-phenyl, 4-acetoxyphenyl, 2-chloro-phenyl, 3,4-dichlorophenyl, and compounds wherein R5 is methyl and R2, R3 and R4 are equal to H and X is a phenyl residue, and the residue A is phenyl, 4-fluoro-phenyl, 4-chloro-phenyl, 4-methyl-phenyl, 4-ethyloxy-phenyl, 3-trifluoromethyl-phenyl, 2-thiophenyl or 4-methylthiophenyl, and compounds wherein R5 is methyl and R2 is methyl and R3 and R4 are equal to H and A is equal to 4-fluoro-phenyl and the residue X is phenyl.

These compounds can be employed to produce medicaments with a TASK-1 channel-blocking effect for the therapy and prophylaxis of TASK-1 channel-mediated diseases. The compounds of the formula I and/or their pharmaceutically acceptable salts can further be used for the therapy or prophylaxis of cardiac arrhythmias, e.g. of arrhythmias that respond to the changes in the shape of the action potential, mainly a prolongation of the action potential, which is induced by TASK-1 blockade.

The compounds of the formula I and/or their pharmaceutically acceptable salts can be employed for terminating existent atrial fibrillation or flutter to restore the sinus rhythm (cardioversion). In addition, the compounds reduce the susceptibility for a new development of atrial fibrillation events, thus the compounds are suitable for prophylactic treatment by maintenance of sinus rhythm (rhythm control). The substances are devoid of a ventricular proarrhythmic risk (prolongation of the QT-interval and Torsades de pointe arrhythmias).

The compounds of the formula I and/or their pharmaceutically acceptable salts can be employed for producing a medicament for the treatment and/or prevention of arrhythmias, particularly atrial trachyarrhythmias, atrial fibrillation and atrial flutter The compounds of the formula I and/or their pharmaceutically acceptable salts are further suitable for producing a medicament for the therapy or prophylaxis of sleep-related respiratory disorders, central and obstructive sleep apneas, upper airway resistance syndrome, Cheyne-Stokes respiration, snoring, disrupted central respiratory drive, sudden child death, postoperative hypoxia and apnea, muscle-related respiratory disorders, respiratory disorders after long-term mechanical ventilation (weaning), respiratory disorders during adaptation in high mountains, acute and for respiratory disorders, chronic lung disorders with hypoxia and hypercapnia, chronic obstructive pulmonary disease (COPD) and obesity hypoventilation syndrome.

The compounds of the formula I and/or their pharmaceutically acceptable salts are further suitable as a respiratory stimulant for the prevention and treatment of respiratory depression associated with anesthesia or procedural sedations for small interventions or for diagnostic purposes, for the treatment and prevention of respiratory depression by opioids in chronic pain treatment e.g. in cancer or palliative care or procedural sedations and/or for weaning from longterm mechanical ventilation.

The compounds of the formula I and/or their pharmaceutically acceptable salts are further suitable for the treatment and/or prevention of multiple sclerosis and inflammatory and degenerative disorders of the central nervous system.

The compounds of the invention of the formula I and their pharmaceutically acceptable salts can thus be used on animals, preferably on mammals, and in particular on humans, as pharmaceuticals on their own, in mixtures with one another or in the form of pharmaceutical preparations (pharmaceutical compositions).

Thus, a further embodiment of the present invention is a pharmaceutical preparation comprising an effective amount of a compound of the formula I and/or of its pharmaceutically acceptable salts, together with pharmaceutically acceptable carriers and additives, alone or in combination with other pharmacological active ingredients or pharmaceuticals. The pharmaceutical preparations usually comprise from 0.1 to 90 percent by weight of the compounds of the formula I and/or their pharmaceutically acceptable salts. The pharmaceutical preparations can be produced in a manner known per se. For this purpose, the compounds of the formula I and/or their pharmaceutically acceptable salts are converted together with one or more solid or liquid pharmaceutical vehicles and/or excipients and, if desired, in combination with other pharmaceutical active ingredients into a suitable dosage form, which can then be used as pharmaceutical in human medicine or veterinary medicine.

Pharmaceuticals which comprise a compound of the formula I and/or its pharmaceutically acceptable salts can moreover be administered for example orally, intravenously, intramuscular, subcutaneously, nasally, topically, pharyngeally or by inhalation, and the preferred administration depends on the individual case, for example on the particular manifestation of the disorder. The compounds of the formula I can moreover be used alone or together with pharmaceutical excipients, in particular both in veterinary and in human medicine. The pharmaceuticals comprise active ingredients of the formula I and/or their pharmaceutically acceptable salts generally in an amount of from 0.01 mg to 1 g per dose unit.

The skilled worker is familiar on the basis of his expert knowledge with which excipients are suitable for the desired pharmaceutical formulation. Besides solvents, gel formers, suppository bases, tablet excipients and other active substance carriers it is possible to use for example antioxidants, dispersants, emulsifiers, antifoams, masking flavors, preservatives, solubilizers, agents for achieving a depot effect, buffer substances or colorants.

For a form for oral use, the active compounds are mixed with the additives suitable for this purpose, such as carriers, stabilizers or inert diluents, and converted by conventional methods into suitable presentations such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can take place both as dry and as wet granules. Suitable as oily carriers or as solvents are, for example, vegetable or animal oils such as sunflower oil or fish liver oil. Suitable solvents for aqueous or alcoholic solutions are, for example, water, ethanol or sugar solutions or mixtures thereof. Examples of further excipients, also for other administration forms, are polyethylene glycols and polypropylene glycols.

For subcutaneous, intramuscular or intravenous administration, the active compounds are converted if desired with the substances usual for this purpose, such as solubilizers, emulsifiers or further excipients, into a solution, suspension or emulsion. The compounds of the formula I and/or their pharmaceutically acceptable salts may also be lyophilized and the resulting lyophilizates be used, for example, for producing products for injection or infusion. Examples of suitable solvents are: water, physiological saline or alcohols, for example ethanol, propanol, glycerol, as well as sugar solutions such as glucose or mannitol solutions, or else mixtures of the various solvents mentioned.

Suitable as pharmaceutical formulation for administration in the form of aerosols or sprays are, for example, solutions, suspensions or emulsions of the active ingredient of the formula I or their pharmaceutically acceptable salts in a pharmaceutically acceptable solvent, such as in particular ethanol or water, or a mixture of such solvents. The formulation may if required also comprise other pharmaceutical excipients such as surfactants, emulsifiers and stabilizers, and a propellant gas. Such a preparation comprises the active ingredient normally in a concentration of about 0.1 to 10, in particular of about 0.3 to 3 percent by weight.

The dosage of the active ingredient to be administered or of the pharmaceutically acceptable salts thereof depends on the individual case and should be adapted to the circumstances of the individual case as usual for an optimal effect. Thus, it naturally depends on the frequency of administration and on the potency and duration of action of the particular compounds employed for therapy or prophylaxis, but also on the type and severity of the disease to be treated, and on the gender, age, weight and individual response of the human or animal to be treated, and on whether therapy is acute or prophylactic.

The daily dose of a compound of the formula I and/or its pharmaceutically acceptable salts for a patient weighing about 75 kg is normally at least 0.001 mg/kg to 100 mg/kg of body weight, preferably 0.01 mg/kg to 20 mg/kg. Even higher dosages may also be necessary for acute episodes of the disease, for example in an intensive care unit. Up to 800 mg per day may be necessary. The dose may be in the form of a single dose or be divided into a plurality, for example two, three or four, single doses. Parenteral administration by injection or infusion, for example a continuous intravenous infusion, may also be advantageous, especially in the treatment of acute cases of cardiac arrhythmias, for example in an intensive care unit.

EXAMPLES

The following examples illustrate the various embodiments of the present invention and are part of the present invention.

1-(4-Morpholin-4-yl-3,6-dihydro-2H-pyridin-1-yl)-ethanone (1)

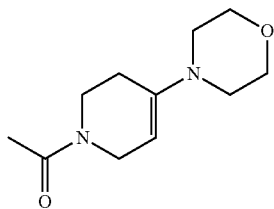

According to Scheme 1, step 1: a mixture of morpholine (67.85 g, 0.779 mol), 1-acetyl-4-piperidone (99.95 g, 0.708 mol) and para-toluenesulfonic acid (0.366 g, 2.1 mmol) in toluene (300 ml) was heated in a Dean-Stark trap apparatus for 16 h at reflux. Solvents were evaporated in vacuo to give 149 g of 1-(4-Morpholin-4-yl-3,6-dihydro-2H-pyridin-1-yl)-ethanone (1) which was used in the next step without any further purification.

3-(5-Acetyl-4,5,6,7-tetrahydro-1H-pyrazolo[4,3-c]pyridin-3-yl)-benzonitrile (3a)

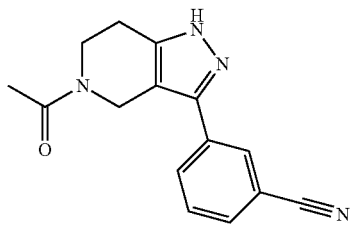 [SMILES: CC(=O)N1CCc2[nH]nc(-c3cccc(C#N)c3)c2C1]

According to Scheme 1, method A: steps 2-3: to a solution of 1-(4-Morpholin-4-yl-3,6-dihydro-2H-pyridin-1-yl)-ethanone (1) (6.35 g, 30.2 mmol) in dry dichloromethane (30 ml) at 0° C. was added triethylamine (3.056 g, 30.2 mmol) and after stirring the solution at 0° C. for 10 min, 3-cyanobenzoyl chloride (5 g, 30.2 mmol) was added. The mixture was stirred for 45 min at 0° C. then the mixture was allowed to warm to room temperature and stirred overnight. 5% aqueous HCl was added and the mixture was stirred for 2 h. The mixture was extracted with dichloromethane and the organic layer was washed with water, filtered over a short pad of silica gel and evaporated to dryness to give 8 g of 3-(1-Acetyl-4-oxo-piperidine-3-carbonyl)-benzonitrile (2a) which was used immediately in the next step without purification.

To a mixture of 3-(1-Acetyl-4-oxo-piperidine-3-carbonyl)-benzonitrile (2a) (8 g, 29.6 mmol) in ethanol (26 ml) at 10° C. hydrazine hydrate (4.44 g, 88.8 mmol) was added slowly within 5 min. The mixture was stirred 3 h and allowed to warm to room temperature overnight. The mixture was concentrated to ¼ of its volume until a precipitate formed. The suspension was stirred for 2 h, cooled down and filtrated. The solid was washed with a small amount of ethanol. A second portion of product precipitated overnight from the filtrate and was pooled with the first portion of solid to give 4.02 g of 3-(5-Acetyl-4,5,6,7-tetrahydro-1H-pyrazolo[4,3-c]pyridin-3-yl)-benzonitrile (3a) as a solid.

$R_t$=1.20 min (LC-method 7). Detected mass: 267.15 [M+H$^+$]

1-[3-(4-Trifluoromethyl-pyridin-2-yl)-1,4,6,7-tetrahydro-pyrazolo[4,3-c]pyridin-5-yl]-ethanone (3m)

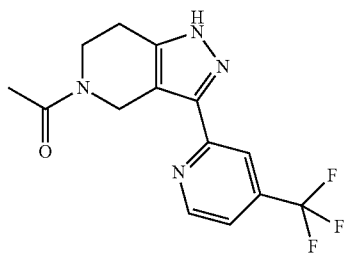 [SMILES: CC(=O)N1CCc2[nH]nc(-c3cc(C(F)(F)F)ccn3)c2C1]

According to Scheme 1, method B: to a solution of 4-(trifluoromethyl)-2-pyridinecarboxylic acid (0.42 g, 1.54 mmol) in dry tetrahydrofuran was added N-methylmorpholine (163 mg, 1.62 mmol) and isobutylchloroformate (221 mg, 1.62 mmol) and the mixture was stirred for 30 min at room temperature and the solid was filtered off. The filtrate was used in the subsequent reaction.

To a solution of 1-acetyl-4-piperidone (0.207 g, 1.466 mmol) in tetrahydrofuran at 0° C. was added dropwise 1M lithium bis(trimethyldisilazide) in tetrahydrofuran (1.54 mmol, 1.54 ml) and the mixture was stirred for 15 min at 0° C., then the mixture was cooled down to −78° C. The mixed anhydride solution generated above was added to this mixture at −78° C., the mixture was allowed to warm to room temperature and stirred for 90 min. To this mixture at 10° C. was added ethanol (5 ml) and hydrazine hydrate (0.603 g, 7.72 mmol) and the mixture was stirred 16 h at room temperature. The mixture was concentrated and after addition of CH$_2$Cl$_2$ and aqueous NaHCO$_3$ the mixture was extracted 3 times with CH$_2$Cl$_2$, the combined organic layers were washed with brine, dried over NaCl, filtrated and the filtrate was evaporated to dryness to give 323 mg of 1-[3-(4-Trifluoromethyl-pyridin-2-yl)-1,4,6,7-tetrahydro-pyrazolo[4,3-c]pyridin-5-yl]-ethanone (3m). The product was used crude in the next reaction steps without further purification.

$R_t$=1.61 min (LC-method 1). Detected mass: 311.18 [M+H$^+$]

The examples in the following table were obtained according to Scheme 1, Method A or Method B as specified, from the specified starting compound (SC) (by following a similar procedure as used for the synthesis of (3a); in part the compounds were purified by reverse phase HPLC (CH$_3$CN/water gradient with 0.1% trifluoroacetic acid).

| Comp. No. (Meth.) | Starting Comp. | Product | Chemical Name | R_t/[min] (LC-Meth.) [M + H^+] |
|---|---|---|---|---|
| 3b (A) | 4-fluoro-benzoyl chloride | | 1-[3-(4-Fluoro-phenyl)-1,4,6,7-tetrahydro-pyrazolo[4,3-c]pyridin-5-yl]-ethanone | 2.32 (8) 260.12 |
| 3c (A) | 6-(tri-fluoro-methyl)-pyridine-2-carbonyl chloride | | 1-[3-(6-Trifluoro-methyl-pyridin-2-yl)-1,4,6,7-tetrahydro-pyrazolo[4,3-c]pyridin-5-yl]-ethanone | 1.10 (4) 311.2 |
| 3d (A) | 3-Trifluoro methyl-benzoyl chloride | | 1-[3-(3-Trifluoro-methyl-phenyl)-1,4,6,7-tetra-hydro-pyrazolo[4,3-c]pyridin-5-yl]-ethanone | 1.12 (4) 310.11 |
| 3e (A) | 3-Trifluoro methoxy-benzoyl chloride | | 1-[3-(3-Trifluoro-methoxy-phenyl)-1,4,6,7-tetrahydro-pyrazolo[4,3-c]pyridin-5-yl]-ethanone | 3.60 (2) 326.16 |
| 3f (A) | 3-chloro-benzoyl chloride | | 1-[3-(3-Chloro-phenyl)-1,4,6,7-tetrahydro-pyrazolo[4,3-c]pyridin-5-yl]-ethanone | 0.94 (4) 275.08 |
| 3g (A) | 2-Fluoro-5-methoxy-benzoyl chloride | | 1-[3-(2-Fluoro-5-methoxy-phenyl)-1,4,6,7-tetrahydro-pyrazolo[4,3-c]pyridin-5-yl]-ethanone | 2.97 (2) 290.15 |

-continued

| Comp. No. (Meth.) | Starting Comp. | Product | Chemical Name | R$_t$/[min] (LC-Meth.) [M + H$^+$] |
|---|---|---|---|---|
| 3h (A) | 3-methoxy-benzoyl chloride | | 1-[3-(3-Methoxy-phenyl)-1,4,6,7-tetrahydro-pyrazolo[4,3-c]pyridin-5-yl]-ethanone | 0.99 (4) 272.5 |
| 3i (A) | 4-Fluoro-3-methoxy-benzoyl chloride | | 1-[3-(4-Fluoro-3-methoxy-phenyl)-1,4,6,7-tetrahydro-pyrazolo[4,3-c]pyridin-5-yl]-ethanone | 1.02 (4) 290.2 |
| 3j (A) | 4-Fluoro-3-cyano-benzoyl chloride | | 5-(5-Acetyl-4,5,6,7-tetrahydro-1H-pyrazolo[4,3-c]pyridin-3-yl)-2-fluoro-benzonitrile | 1.01 (4) 285.1 |
| 3k (A) | 3-Fluoro-benzoyl chloride | | 1-[3-(3-Fluoro-phenyl)-1,4,6,7-tetrahydro-pyrazolo[4,3-c]pyridin-5-yl]-ethanone | 1.47 (9) 260.16 |
| 3l (A) | 4-Trifluoromethyl-benzoyl chloride | | 1-[3-(4-Trifluoromethyl-phenyl)-1,4,6,7-tetrahydro-pyrazolo[4,3-c]pyridin-5-yl]-ethanone | 1.00 (4) 309.9 |

-continued

| Comp. No. (Meth.) | Starting Comp. | Product | Chemical Name | R$_t$/[min] (LC-Meth.) [M + H$^+$] |
|---|---|---|---|---|
| 3n (B) | 4-Bromo-pyridine-2-carbonyl chloride | | 1-[3-(4-Bromo-pyridin-2-yl)-1,4,6,7-tetrahydro-pyrazolo[4,3-c]pyridin-5-yl]-ethanone | 0.91 (1) 321.09 |
| 3o (B) | 2-Bromo-iso-nicotinoyl chloride | | 1-[3-(2-Bromo-pyridin-4-yl)-1,4,6,7-tetrahydro-pyrazolo[4,3-c]pyridin-5-yl]-ethanone | 0.81 (1) 321.06 |
| 3p (B) | 5-Bromo-nicotinoyl chloride | | 1-[3-(5-Bromo-pyridin-3-yl)-1,4,6,7-tetrahydro-pyrazolo[4,3-c]pyridin-5-yl]-ethanone | 0.96 (4) 321.12 |
| 3q (A) | 3-Methyl-benzoyl chloride | | 1-(3-m-Tolyl-1,4,6,7-tetrahydro-pyrazolo[4,3-c]pyridin-5-yl)-ethanone | 0.92 (1) 256.18 |
| 3r (B) | 6-Methyl-pyridine-2-carbonyl chloride | | 1-[3-(6-Methyl-pyridin-2-yl)-1,4,6,7-tetrahydro-pyrazolo[4,3-c]pyridin-5-yl]-ethanone | 0.74 (1) 257.11 |
| 3s (A) | 6-Bromo-pyridine-2-carbonyl chloride | | 1-[3-(6-Bromo-pyridin-2-yl)-1,4,6,7-tetrahydro-pyrazolo[4,3-c]pyridin-5-yl]-ethanone | 1.06 (4) 321.1 |

| Comp. No. (Meth.) | Starting Comp. | Product | Chemical Name | R,/[min] (LC-Meth.) [M + H⁺] |
|---|---|---|---|---|
| 3t (B) | 4-Methyl-pyridine-2-carbonyl chloride | | 1-[3-(4-Methyl-pyridin-2-yl)-1,4,6,7-tetrahydro-pyrazolo[4,3-c]pyridin-5-yl]-ethanone | nd (nd) nd |
| 3u (A) | 6-Methoxy-pyridine-2-carbonyl chloride | | 1-[3-(6-Methoxy-pyridin-2-yl)-1,4,6,7-tetra-hydro-pyrazolo[4,3-c]pyridin-5-yl]-ethanone | 0.9 (1) 273.15 |
| 3v (A) | 6-Chloro-5-methoxy-pyridine-2-carbonyl chloride | | 1-[3-(6-Chloro-5-methoxy-pyridin-2-yl)-1,4,6,7-tetra-hydro-pyrazolo[4,3-c]pyridin-5-yl]-ethanone | 1.02 (4) 307.1 |
| 3w (B) | 3-Methyl-pyridine-2-carbonyl chloride | | 1-[3-(3-Methyl-pyridin-2-yl)-1,4,6,7-tetra-hydro-pyrazolo[4,3-c]pyridin-5-yl]-ethanone | nd (nd) nd |
| 3x (A) | 4-Methoxy-pyridine-2-carbonyl chloride | | 1-[3-(4-Methoxy-pyridin-2-yl)-1,4,6,7-tetra-hydro-pyrazolo[4,3-c]pyridin-5-yl]-ethanone | 0.55 (1) 273.16 |
| 3y (A) | Thio-phene-2-carbonyl chloride | | 1-(3-Thiophen-2-yl-1,4,6,7-tetrahydro-pyrazolo[4,3-c]pyridin-5-yl)-ethanone | 0.94 (4) 248.08 |

-continued

| Comp. No. (Meth.) | Starting Comp. | Product | Chemical Name | $R_t$/[min] (LC-Meth.) [M + H$^+$] |
|---|---|---|---|---|
| 3z (A) | 5-Chloro-thio-phene-2-carbonyl chloride | | 1-[3-(5-Chloro-thiophen-2-yl)-1,4,6,7-tetra-hydro-pyrazolo[4,3-c]pyridin-5-yl]-ethanone | 1.07 (4) 282.02 |
| 3aa (A) | Thio-phene-3-carbonyl chloride | | 1-(3-Thiophen-3-yl-1,4,6,7-tetrahydro-pyrazolo[4,3-c]pyridin-5-yl)-ethanone | 0.93 (4) 248.05 |

8-Acetyl-8-aza-bicyclo[3.2.1]octan-3-one (4a)

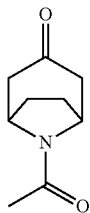

According to Scheme 2, Step 1:

A suspension of nortropinone hydrochloride (1 g, 6.187 mmol) in acetic anhydride was stirred at 70° C. for 3 h. Water was added, the mixture was boiled for 30 min and cooled down to room temperature. CH$_2$Cl$_2$ and 1N aqueous NaOH was added until pH 9 was reached. The mixture was extracted 2 times with CH$_2$Cl$_2$, the combined organic layers were dried over Na$_2$SO$_4$, filtrated and the solution was evaporated to dryness to give 0.7 g of 8-Acetyl-8-aza-bicyclo[3.2.1]octan-3-one (4a).

$R_t$=1.76 min (LC-method 2). Detected mass: 168.24 [M+H$^+$]

1-(3-Phenyl-4,5,11-triaza-tricyclo[6.2.1.0*2,6*]undeca-2(6),3-dien-11-yl)-ethanone (5a)

According to Scheme 2, Steps 2+3:

To a mixture of 8-Acetyl-8-aza-bicyclo[3.2.1]octan-3-one (4a) (350 mg, 2.1 mmol) in dry tetrahydrofuran at 0° C. was added 1N lithium hexamethyldisilazide (2.2 ml, 2.2 mmol) and after 5 min the mixture was cooled to −78° C.

To a solution of 3-cyanobenzoic acid (323 mg, 2.2 mmol) and N-methyl-morpholine (232 mg, 2.3 mmol) in tetrahydrofuran was added isobutylchloroformate (300 mg, 2.2 mmol). The mixture was stirred for 5 min at 25° C., filtrated and washed with dry tetrahydrofuran. This solution was added dropwise to the −78° C. mixture above and the mixture was then allowed to warm to 25° C. for 1 h. Solvents were evaporated, CH$_2$Cl$_2$ and water were added, the organic layer was dried over Na$_2$SO$_4$, filtrated and the solution was evaporated to dryness, redissolved in ethanol (10 ml).

Hydrazine hydrate (245 mg, 3.14 mmol) was added and the solution was stirred for min. Solvents were evaporated and the crude product was purified by silica gel chromatography (dichloromethane/methanol 100/0 to 70/30) to give 45 mg of 1-(3-Phenyl-4,5,11-triaza-tricyclo[6.2.1.0*2,6*]undeca-2(6),3-dien-11-yl)-ethanone (5a).

$R_t$=1.01 min (LC-method 4). Detected mass: 293.18 [M+H$^+$]

1-[3-(4-Fluoro-phenyl)-4,5,11-triaza-tricyclo[6.2.1.0*2,6*]undeca-2(6),3-dien-11-yl]-ethanone (5b)

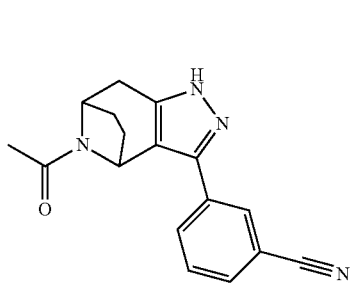 [SMILES: CC(=O)N1C2CCC1c1c(-c3cccc(C#N)c3)n[nH]c1C2]

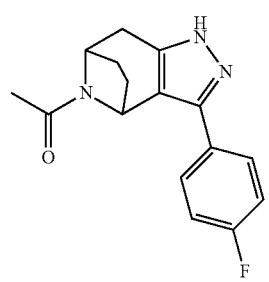 [SMILES: CC(=O)N1C2CCC1c1c(-c3ccc(F)cc3)n[nH]c1C2]

1-[3-(4-Fluoro-phenyl)-4,5,11-triaza-tricyclo[6.2.1.0*2,6*]undeca-2(6),3-dien-1-yl]-ethanone (5b) was obtained by following a similar reaction as used for synthesis of (5a).

$R_t$=1.06 min (LC-method 4). Detected mass: 286.18 [M+H$^+$]

3-[5-Acetyl-1-(2,4-difluoro-benzyl)-4,5,6,7-tetrahydro-1H-pyrazolo[4,3-c]pyridin-3-yl]-benzonitrile
(6a)

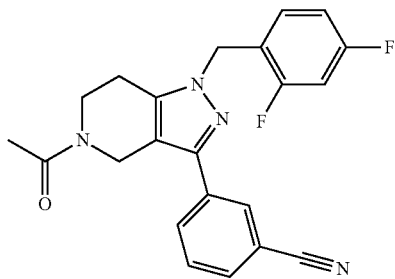 [SMILES: CC(=O)N1CCc2c(c(-c3cccc(C#N)c3)nn2Cc2ccc(F)cc2F)C1]

According to Scheme 3:

A mixture of 3-(5-Acetyl-4,5,6,7-tetrahydro-1H-pyrazolo[4,3-c]pyridin-3-yl)-benzonitrile (3a) (0.48 g, 1.8 mmol), 2,4-difluorobenzyl bromide (0.41 g, 1.99 mmol) and K$_2$CO$_3$ (498 mg, 3.6 mmol) in 14 ml CH$_3$CN was stirred at 80° C. for 16 h. A second portion of 2,4-difluorobenzyl bromide (0.41 g, 1.99 mmol) was added and the mixture was stirred for additional 7 h. Water was added, the mixture was extracted 3 times with ethyl acetate, the combined organic layers were dried over MgSO$_4$, filtrated and the solution was evaporated to dryness. The crude product was crystallized from 10 ml 2-propanol and dried in vacuo to give 0.364 g of 3-[5-Acetyl-1-(2,4-difluoro-benzyl)-4,5,6,7-tetrahydro-1H-pyrazolo[4,3-c]pyridin-3-yl]-benzonitrile (6a).

$R_t$=1.62 min (LC method 7). Detected mass: 393.15 [M+H$^+$].

The examples in the following table were obtained according to Scheme 4 by following a similar reaction as used for synthesis of (6a). The corresponding halogenides used (Hal-CH$_2$—X; particularly the corresponding bromides or chlorides) are obvious to the man skilled in the art and were commercially available. Reaction conditions varied slightly by reaction time (1-3 days), temperature (50-80° C.).

Products were routinely purified by reverse phase HPLC (CH$_3$CN/water gradient with 0.1% trifluoroacetic acid).

| Comp. No. | SC | Product | Chemical Name | $R_t$/[min] (LC-Method) [M + H$^+$] |
|---|---|---|---|---|
| 6b | 3d | | 1-[1-(6-Chloro-pyridin-3-ylmethyl)-3-(3-trifluoromethyl-phenyl)-1,4,6,7-tetrahydro-pyrazolo[4,3-c]pyridin-5-yl]-ethanone | 1.26 (4) 435.09 |
| 6c | 3d | | 1-[1-(4-Chloro-pyridin-3-ylmethyl)-3-(3-trifluoromethyl-phenyl)-1,4,6,7-tetrahydro-pyrazolo[4,3-c]pyridin-5-yl]-ethanone | 1.22 (4) 435.09 |
| 6d | 3d | | 1-[1-(3-Methyl-pyridin-2-ylmethyl)-3-(3-trifluoromethyl-phenyl)-1,4,6,7-tetrahydro-pyrazolo[4,3-c]pyridin-5-yl]-ethanone | 3.97 (2) 415.28 |

-continued

| Comp. No. | SC | Product | Chemical Name | R$_t$/[min] (LC-Method) [M + H$^+$] |
|---|---|---|---|---|
| 6e | 3b | 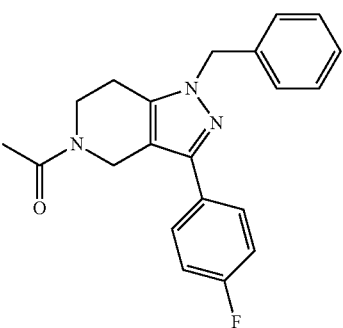 [SMILES: CC(=O)N1CCc2c(c(-c3ccc(F)cc3)nn2Cc2ccccc2)C1] | 1-[1-Benzyl-3-(4-fluoro-phenyl)-1,4,6,7-tetrahydro-pyrazolo[4,3-c]pyridin-5-yl]-ethanone | 2.29 (15) 350.16 |
| 6f | 3b | 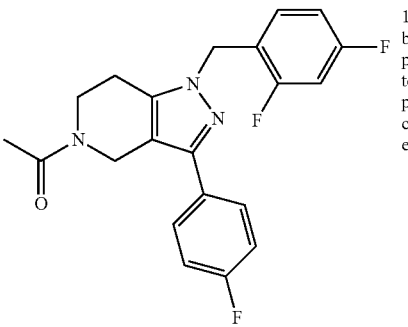 | 1-[1-(2,4-Difluoro-benzyl)-3-(4-fluoro-phenyl)-1,4,6,7-tetrahydro-pyrazolo[4,3-c]pyridin-5-yl]-ethanone | 2.35 (12) 386.02 |
| 6g | 3c | 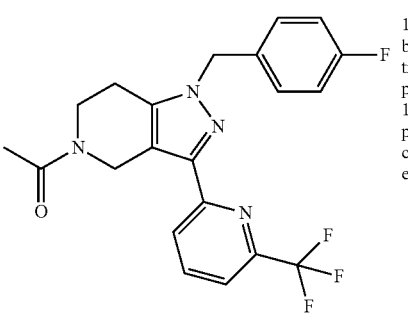 | 1-[1-(4-Fluoro-benzyl)-3-(6-trifluoromethyl-pyridin-2-yl)-1,4,6,7-tetrahydro-pyrazolo[4,3-c]pyridin-5-yl]-ethanone | 1.31 (4) 419.17 |
| 6h | 3m | 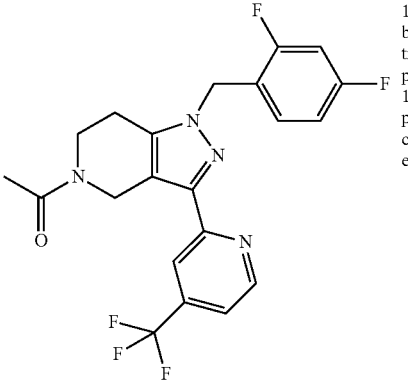 | 1-[1-(2,4-Difluoro-benzyl)-3-(4-trifluoromethyl-pyridin-2-yl)-1,4,6,7-tetrahydro-pyrazolo[4,3-c]pyridin-5-yl]-ethanone | 2.02 (9) 437.23 |

-continued

| Comp. No. | SC | Product | Chemical Name | R$_t$/[min] (LC-Method) [M + H$^+$] |
|---|---|---|---|---|
| 6i | 3c | | 1-[1-(2,4-Difluoro-benzyl)-3-(6-trifluoromethyl-pyridin-2-yl)-1,4,6,7-tetrahydro-pyrazolo[4,3-c]pyridin-5-yl]-ethanone | 1.3 (4) 437.15 |
| 6j | 3n | | 1-[3-(4-Bromo-pyridin-2-yl)-1-(2,4-difluoro-benzyl)-1,4,6,7-tetrahydro-pyrazolo[4,3-c]pyridin-5-yl]-ethanone | 1.2 (1) 447.1 |
| 6k | 3o | | 1-[3-(2-Bromo-pyridin-4-yl)-1-(2,4-difluoro-benzyl)-1,4,6,7-tetrahydro-pyrazolo[4,3-c]pyridin-5-yl]-ethanone | 1.12 (1) 447.14 |
| 6m | 3p | | 1-[3-(5-Bromo-pyridin-3-yl)-1-(2,4-difluoro-benzyl)-1,4,6,7-tetrahydro-pyrazolo[4,3-c]pyridin-5-yl]-ethanone | 1.24 (4) 447.2 |

-continued

| Comp. No. | SC | Product | Chemical Name | R$_t$/[min] (LC-Method) [M + H$^+$] |
|---|---|---|---|---|
| 6n | 5a | | 3-[11-Acetyl-5-(2,4-difluoro-benzyl)-4,5,11-triaza-tricyclo[6.2.1.0²,⁶]undeca-2(6),3-dien-3-yl]-benzonitrile | 1.25 (4) 419.21 |
| 6o | 5b | | 1-[5-(2,4-Difluoro-benzyl)-3-(4-fluoro-phenyl)-4,5,11-triaza-tricyclo[6.2.1.02,6]undeca-2(6),3-dien-11-yl]-ethanone | 1.26 (4) 412.17 |
| 6p | 3q | | 1-[1-(6-Chloro-pyridin-3-ylmethyl)-3-m-tolyl-1,4,6,7-tetrahydro-pyrazolo[4,3-c]pyridin-5-yl]-ethanone | 1.2 (4) 381.12 |
| 6q | 3d | | 1-[1-(4-Methoxy-pyridin-2-ylmethyl)-3-(3-trifluoromethyl-phenyl)-1,4,6,7-tetrahydro-pyrazolo[4,3-c]pyridin-5-yl]-ethanone | 3.25 (2) 431.3 |

-continued

| Comp. No. | SC | Product | Chemical Name | R_t[min] (LC-Method) [M + H⁺] |
|---|---|---|---|---|
| 6r | 3q | | 1-[1-(4-Chloro-pyridin-3-ylmethyl)-3-m-tolyl-1,4,6,7-tetrahydro-pyrazolo[4,3-c]pyridin-5-yl]-ethanone | 1.16 (4) 381.11 |
| 6s | 3d | | 1-[1-(3-Methoxy-pyridin-2-ylmethyl)-3-(3-trifluoromethyl-phenyl)-1,4,6,7-tetrahydro-pyrazolo[4,3-c]pyridin-5-yl]-ethanone | 4.04 (2) 431.3 |
| 6t | 3f | | 1-[3-(3-Chloro-phenyl)-1-(3-methyl-pyridin-2-ylmethyl)-1,4,6,7-tetrahydro-pyrazolo[4,3-c]pyridin-5-yl]-ethanone | 1.1 (1) 381.12 |
| 6u | 3c | | 1-[1-[1-(4-Fluoro-phenyl)-ethyl]-3-(6-trifluoromethyl-pyridin-2-yl)-1,4,6,7-tetrahydro-pyrazolo[4,3-c]pyridin-5-yl]-ethanone | 1.35 (4) 433.14 |
| 6v | 3r | | 1-[1-(2,4-Difluoro-benzyl)-3-(6-methyl-pyridin-2-yl)-1,4,6,7-tetrahydro-pyrazolo[4,3-c]pyridin-5-yl]-ethanone | 3.15 (2) 383.23 |

-continued

| Comp. No. | SC | Product | Chemical Name | $R_t$/[min] (LC-Method) [M + H$^+$] |
|---|---|---|---|---|
| 6w | 3s | | 1-[3-(6-Bromo-pyridin-2-yl)-1-(2,4-difluoro-benzyl)-1,4,6,7-tetrahydro-pyrazolo[4,3-c]pyridin-5-yl]-ethanone | 1.3 (4) 447.17 |
| 6x | 3t | | 1-[1-(2,4-Difluoro-benzyl)-3-(4-methyl-pyridin-2-yl)-1,4,6,7-tetrahydro-pyrazolo[4,3-c]pyridin-5-yl]-ethanone | 0.97 (1) 383.2 |
| 6y | 3u | | 1-[1-(2,4-Difluoro-benzyl)-3-(6-methoxy-pyridin-2-yl)-1,4,6,7-tetrahydro-pyrazolo[4,3-c]pyridin-5-yl]-ethanone | 1.15 (1) 399.19 |
| 6z | 3v | | 1-[3-(6-Chloro-5-methoxy-pyridin-2-yl)-1-(2,4-difluoro-benzyl)-1,4,6,7-tetrahydro-pyrazolo[4,3-c]pyridin-5-yl]-ethanone | 1.25 (4) 433.11 |

-continued

| Comp. No. | SC | Product | Chemical Name | $R_t$/[min] (LC-Method) [M + H$^+$] |
|---|---|---|---|---|
| 6ab | 3w | | 1-[1-(2,4-Difluoro-benzyl)-3-(3-methyl-pyridin-2-yl)-1,4,6,7-tetrahydro-pyrazolo[4,3-c]pyridin-5-yl]-ethanone | 1.14 (4) 383.1 |
| 6ac | 3x | | 1-[1-(2,4-Difluoro-benzyl)-3-(4-methoxy-pyridin-2-yl)-1,4,6,7-tetrahydro-pyrazolo[4,3-c]pyridin-5-yl]-ethanone | 2.75 (2) 399.26 |
| 6ad | 3d | | 1-[1-(2-Methyl-thiazol-4-ylmethyl)-3-(3-trifluoromethyl-phenyl)-1,4,6,7-tetrahydro-pyrazolo[4,3-c]pyridin-5-yl]-ethanone | 1.23 (4) 421.12 |
| 6ae | 3d | | 1-[1-Thiazol-2-ylmethyl-3-(3-trifluoromethyl-phenyl)-1,4,6,7-tetrahydro-pyrazolo[4,3-c]pyridin-5-yl]-ethanone | 1.2 (4) 407.07 |

-continued

| Comp. No. | SC | Product | Chemical Name | R$_t$/[min] (LC-Method) [M + H$^+$] |
|---|---|---|---|---|
| 6af | 3y | | 1-[1-(2,4-Difluoro-benzyl)-3-thiophen-2-yl-1,4,6,7-tetrahydro-pyrazolo[4,3-c]pyridin-5-yl]-ethanone | 1.22 (4) 374.07 |
| 6ag | 3q | | 1-[1-(5-Chloro-thiophen-2-ylmethyl)-3-m-tolyl-1,4,6,7-tetrahydro-pyrazolo[4,3-c]pyridin-5-yl]-ethanone | 1.3 (4) 386.08 |
| 6ah | 3d | | 1-[1-(5-Chloro-thiophen-2-ylmethyl)-3-(3-trifluoromethyl-phenyl)-1,4,6,7-tetrahydro-pyrazolo[4,3-c]pyridin-5-yl]-ethanone | 1.35 (4) 440.07 |
| 6ai | 3a | | 3-[5-Acetyl-1-(5-chloro-thiophen-2-ylmethyl)-4,5,6,7-tetrahydro-1H-pyrazolo[4,3-c]pyridin-3-yl]-benzonitrile | 1.17 (1) 397.03 |

-continued

| Comp. No. | SC | Product | Chemical Name | R<sub>t</sub>/[min] (LC-Method) [M + H<sup>+</sup>] |
|---|---|---|---|---|
| 6aj | 3f | | 1-[3-(3-Chloro-phenyl)-1-(5-chloro-thiophen-2-ylmethyl)-1,4,6,7-tetrahydro-pyrazolo[4,3-c]pyridin-5-yl]-ethanone | 1.25 (1) 406.02 |
| 6ak | 3z | | 1-[3-(5-Chloro-thiophen-2-yl)-1-(2,4-difluoro-benzyl)-1,4,6,7-tetrahydro-pyrazolo[4,3-c]pyridin-5-yl]-ethanone | 1.31 (4) 408.01 |
| 6al | 3aa | | 1-[1-(2,4-Difluoro-benzyl)-3-thiophen-3-yl-1,4,6,7-tetrahydro-pyrazolo[4,3-c]pyridin-5-yl]-ethanone | 1.21 (4) 374.06 |
| 6am | 3d | | 4-[5-Acetyl-3-(3-trifluoromethyl-phenyl)-4,5,6,7-tetrahydro-pyrazolo[4,3-c]pyridin-1-ylmethyl]-benzonitrile | 4.52 (2) 425.29 |
| 6an | 3a | | 3-{5-Acetyl-1-[1-(4-fluoro-phenyl)-ethyl]-4,5,6,7-tetrahydro-1H-pyrazolo[4,3-c]pyridin-3-yl}-benzonitrile | 1.29 (4) 389.2 |

| Comp. No. | SC | Product | Chemical Name | R$_t$/[min] (LC-Method) [M + H⁺] |
|---|---|---|---|---|
| 6ao | 3b | 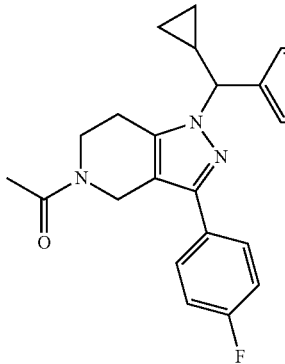 | 1-[1-[Cyclopropyl-(4-fluoro-phenyl)-methyl]-3-(4-fluoro-phenyl)-1,4,6,7-tetrahydro-pyrazolo[4,3-c]pyridin-5-yl]-ethanone | 4.55 (2) 408.34 |
| 6ap | 3e | 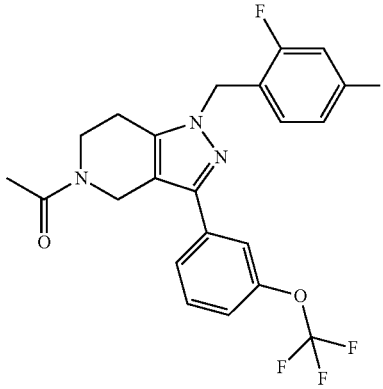 | 1-[1-(2,4-Difluoro-benzyl)-3-(3-trifluoromethoxy-phenyl)-1,4,6,7-tetrahydro-pyrazolo[4,3-c]pyridin-5-yl]-ethanone | 1.23 (4) 452.13 |
| 6aq | 3b | 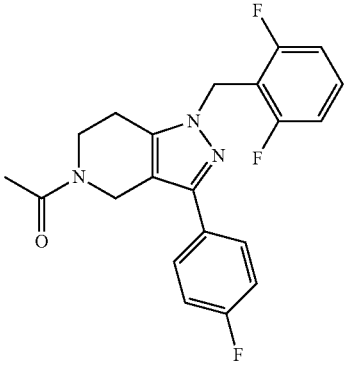 [SMILES: CC(=O)N1CCc2c(c(-c3ccc(F)cc3)nn2Cc2c(F)cccc2F)C1] | 1-[1-(2,6-Difluoro-benzyl)-3-(4-fluoro-phenyl)-1,4,6,7-tetrahydro-pyrazolo[4,3-c]pyridin-5-yl]-ethanone | 2.31 (12) 386.03 |
| 6ar | 3b | 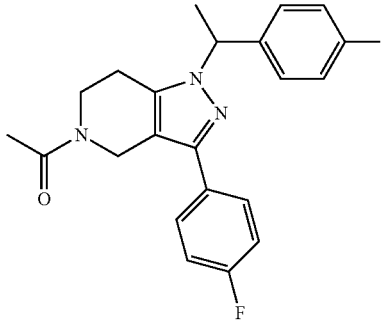 | 1-{3-(4-Fluoro-phenyl)-1-[1-(4-fluoro-phenyl)-ethyl]-1,4,6,7-tetrahydro-pyrazolo[4,3-c]pyridin-5-yl}-ethanone | 3.65 (8) 382.25 |

-continued

| Comp. No. | SC | Product | Chemical Name | $R_t$/[min] (LC-Method) [M + H$^+$] |
|---|---|---|---|---|
| 6as | 3b | | 1-[3-(4-Fluoro-phenyl)-1-(4-trifluoromethyl-benzyl)-1,4,6,7-tetrahydro-pyrazolo[4,3-c]pyridin-5-yl]-ethanone | 2.5 (12) 418.11 |
| 6at | 3h | | 1-[1-(2,4-Difluoro-benzyl)-3-(3-methoxy-phenyl)-1,4,6,7-tetrahydro-pyrazolo[4,3-c]pyridin-5-yl]-ethanone | 1.61 (7) 398.13 |
| 6av | 3b | | 1-[3-(4-Fluoro-phenyl)-1-(3-trifluoromethyl-benzyl)-1,4,6,7-tetrahydro-pyrazolo[4,3-c]pyridin-5-yl]-ethanone | 2.49 (12) 418.02 |
| 6aw | 3e | | 1-[1-[1-(4-Fluoro-phenyl)-ethyl]-3-(3-trifluoromethoxy-phenyl)-1,4,6,7-tetrahydro-pyrazolo[4,3-c]pyridin-5-yl]-ethanone | 1.25 (4) 447.74 |

-continued

| Comp. No. | SC | Product | Chemical Name | R$_t$/[min] (LC-Method) [M + H$^+$] |
|---|---|---|---|---|
| 6ax | 3i | | 1-[1-(2,4-Difluoro-benzyl)-3-(4-fluoro-3-methoxy-phenyl)-1,4,6,7-tetrahydro-pyrazolo[4,3-c]pyridin-5-yl]-ethanone | 1.26 (4) 416.22 |
| 6ay | 3a | | 3-[5-Acetyl-1-(2,5-difluoro-benzyl)-4,5,6,7-tetrahydro-1H-pyrazolo[4,3-c]pyridin-3-yl]-benzonitrile | 1.13 (1) 393.13 |
| 6az | 3q | | 1-[1-(2,4-Difluoro-benzyl)-3-m-tolyl-1,4,6,7-tetrahydro-pyrazolo[4,3-c]pyridin-5-yl]-ethanone | 1.16 (1) 382.3 |
| 6ba | 3f | | 1-[3-(3-Chloro-phenyl)-1-(4-fluoro-2-methyl-benzyl)-1,4,6,7-tetrahydro-pyrazolo[4,3-c]pyridin-5-yl]-ethanone | 1.24 (1) 398.12 |
| 6bb | 3q | | 1-[1-(2-Fluoro-benzyl)-3-m-tolyl-1,4,6,7-tetrahydro-pyrazolo[4,3-c]pyridin-5-yl]-ethanone | 1.26 (4) 364.18 |

-continued

| Comp. No. | SC | Product | Chemical Name | R$_t$/[min] (LC-Method) [M + H$^+$] |
|---|---|---|---|---|
| 6bc | 3d | | 1-[1-(2-Methoxy-benzyl)-3-(3-trifluoromethyl-phenyl)-1,4,6,7-tetrahydro-pyrazolo[4,3-c]pyridin-5-yl]-ethanone | 4.73 (2) 430.32 |
| 6bd | 3f | | 1-[3-(3-Chloro-phenyl)-1-(3-methoxy-benzyl)-1,4,6,7-tetrahydro-pyrazolo[4,3-c]pyridin-5-yl]-ethanone | 1.19 (1) 396.08 |
| 6be | 3b | (+)-Isomer | (+)-1-{3-(4-Fluoro-phenyl)-1-[1-(4-fluoro-phenyl)-ethyl]-1,4,6,7-tetrahydro-pyrazolo[4,3-c]pyridin-5-yl}-ethanone | 4.79 (11) 382.23 |
| 6bf | 3b | (−)-Isomer | (−)-1-{3-(4-Fluoro-phenyl)-1-[1-(4-fluoro-phenyl)-ethyl]-1,4,6,7-tetrahydro-pyrazolo[4,3-c]pyridin-5-yl}-ethanone | 4.79 (11) 382.23 |

-continued
| Comp. No. | SC | Product | Chemical Name | R<sub>t</sub>/[min] (LC-Method) [M + H<sup>+</sup>] |
|---|---|---|---|---|
| 6bg | 3b | 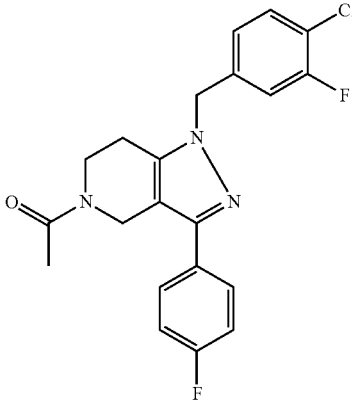 | 1-[1-(4-Chloro-3-fluoro-benzyl)-3-(4-fluoro-phenyl)-1,4,6,7-tetrahydro-pyrazolo[4,3-c]pyridin-5-yl]-ethanone | 2.47 (12) 402.00 |
| 6bh | 3g | 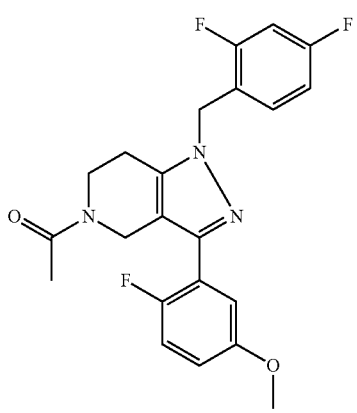 [SMILES: COc1ccc(F)c(-c2nn(Cc3ccc(F)cc3F)c3c2CN(C(C)=O)CC3)c1] | 1-[1-(2,4-Difluoro-benzyl)-3-(2-fluoro-5-methoxy-phenyl)-1,4,6,7-tetrahydro-pyrazolo[4,3-c]pyridin-5-yl]-ethanone | 1.13 (4) 416.12 |
| 6bi | 3j | 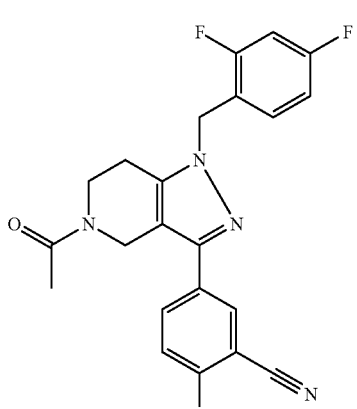 | 5-[5-Acetyl-1-(2,4-difluoro-benzyl)-4,5,6,7-tetrahydro-1H-pyrazolo[4,3-c]pyridin-3-yl]-2-fluoro-benzonitrile | 1.26 (4) 411.19 |

-continued

| Comp. No. | SC | Product | Chemical Name | R_t/[min] (LC-Method) [M + H⁺] |
|---|---|---|---|---|
| 6bj | 3k | | 1-[1-(2,4-Difluoro-benzyl)-3-(3-fluoro-phenyl)-1,4,6,7-tetrahydro-pyrazolo[4,3-c]pyridin-5-yl]-ethanone | 3.45 (13) 386.18 |
| 6bk | 3l | | 1-[1-(2,4-Difluoro-benzyl)-3-(4-trifluoromethyl-phenyl)-1,4,6,7-tetrahydro-pyrazolo[4,3-c]pyridin-5-yl]-ethanone | 1.2 (1) 435.88 |
| 6bl | 3b | | 1-[1-[1-(4-Chloro-phenyl)-propyl]-3-(4-fluoro-phenyl)-1,4,6,7-tetrahydro-pyrazolo[4,3-c]pyridin-5-yl]-ethanone, enantiomer 1 | 3.81 (8) 412.14 |

| Comp. No. | SC | Product | Chemical Name | $R_t$/[min] (LC-Method) [M + H$^+$] |
|---|---|---|---|---|
| 6bm | 3b | Enantiomer 2 | 1-[1-[1-(4-Chloro-phenyl)-propyl]-3-(4-fluoro-phenyl)-1,4,6,7-tetrahydro-pyrazolo[4,3-c]pyridin-5-yl]-ethanone, enantiomer 2 | 3.81 (8) 412.14 |
| 6bn | 3d | | 1-[1-(2-Fluoro-4-methyl-benzyl)-3-(3-trifluoromethyl-phenyl)-1,4,6,7-tetrahydro-pyrazolo[4,3-c]pyridin-5-yl]-ethanone | 1.35 (4) 432.13 |

1-(2,4-Difluoro-benzyl)-3-(4-fluoro-phenyl)-6-methyl-4,5,6,7-tetrahydro-1H-pyrazolo[4,3-c]pyridine, trifluoroacetate salt (7a)

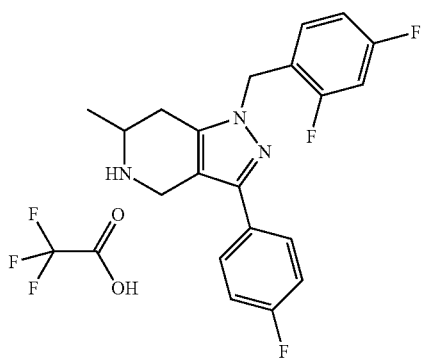

According to Scheme 4:

To a solution of 1 N lithium hexamethyldisilazide in dry tetrahydrofuran (4.69 ml, 4.69 mmol) at −78° C. was added a solution of N-tert-butoxycarbonyl-4-piperidone (1.0 g, 4.69 mmol) in dry diethyl ether (9 ml) dropwise and the mixture was stirred at −78° C. for 30 min. A solution of 4-fluorobenzoyl chloride (743 mg, 4.69 mmol) in dry diethyl ether was added. The mixture was allowed to warm to 25° C. overnight. Water was added, the solution was extracted 3 times with CH$_2$Cl$_2$, the combined organic layers were washed once with brine, dried over Na$_2$SO$_4$, filtrated and the solution was evaporated to dryness, redissolved in ethanol (25 ml) and tetrahydrofuran (11 ml), (2,4-Difluoro-benzyl)-hydrazine (731 mg, 4.62 mmol) was added and the mixture was stirred for 10 min at 25° C. The mixture was poured on 1N aqueous NaOH, extracted 3 times with ethyl acetate, the combined organic layers were washed with brine, dried over Na$_2$SO$_4$, filtrated and the solution was evaporated to dryness. The residue was dissolved in 4N HCl/dioxane (3 ml, 12 mmol) and stirred for 2 days. Solvents were evaporated and the crude product was purified by reverse phase HPLC (CH$_3$CN/water gradient with 0.1% trifluoroacetic acid) to give 257 mg of 1-(2,4-Difluoro-benzyl)-3-(4-fluoro-phenyl)-6-methyl-4,5,6,7-tetrahydro-1H-pyrazolo[4,3-c]pyridine, trifluoroacetate salt (7a).

$R_t$=1.05 min (LC-method 4). Detected mass: 358.24 [M+H$^+$]

1-Benzyl-3-(4-fluoro-phenyl)-4,5,6,7-tetrahydro-1H-pyrazolo[4,3-c]pyridine; hydrochloride (7b)

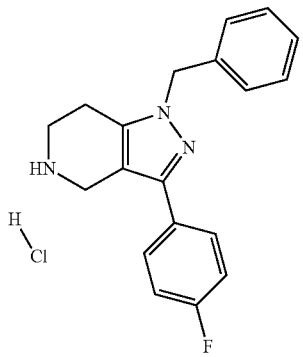 [SMILES: Cl ; Fc1ccc(-c2nn(Cc3ccccc3)c3c2CNCC3)cc1]

According to Scheme 5:

A mixture of 1-[1-Benzyl-3-(4-fluoro-phenyl)-1,4,6,7-tetrahydro-pyrazolo[4,3-c]pyridin-5-yl]-ethanone (6e) (6.9 g, 20 mmol), ethanol (73 ml) and 10N aqueous HCl (137 ml) was stirred at 80° C. for 2 h and then overnight at room temperature. The mixture was concentrated in vacuo and the product was filtrated off and washed with a small amount of cold water to give 4.87 g of 1-Benzyl-3-(4-fluoro-phenyl)-4,5,6,7-tetrahydro-1H-pyrazolo[4,3-c]pyridine; hydrochloride (7b).

$R_t$=1.80 min (LC-method 12). Detected mass: 308.17 [M+H$^+$]

The examples in the following table were obtained according to Scheme 5 by following a similar reaction as used for synthesis of (7b). Reaction conditions varied slightly by reaction time (2 h-3 days), concentration of the aqueous HCl (2-10M) and work-up procedure (sometimes after evaporation of solvents the residue was purified by reverse phase HPLC (CH$_3$CN/water gradient with 0.1% trifluoroacetic acid). The free amine was easily obtained by adding aqueous NaHCO3 and extracting with 3 times CH$_2$Cl$_2$, combining organic layers, drying over Na$_2$SO$_4$, filtrating off and evaporating solvents of the filtrate to dryness.

| Comp. No. | SC | Product | Chemical Name | $R_t$/[min] (LC-Method) [M + H]$^+$ |
|---|---|---|---|---|
| 7c | 6a | | 3-[1-(2,4-Difluoro-benzyl)-4,5,6,7-tetrahydro-1H-pyrazolo[4,3-c]pyridin-3-yl]-benzonitrile | 0.96 (4) 351.33 |
| 7d | 6f | | 1-(2,4-Difluoro-benzyl)-3-(4-fluoro-phenyl)-4,5,6,7-tetrahydro-1H-pyrazolo[4,3-c]pyridine | 1.07 (4) 344.19 |
| 7e | 6be | | 3-(4-Fluoro-phenyl)-1-[1-(4-fluoro-phenyl)-ethyl]-4,5,6,7-tetrahydro-1H-pyrazolo[4,3-c]pyridine (enantiomer 1) | 2.01 (3) 340.1 |

| Comp. No. | SC | Product | Chemical Name | $R_t$/[min] (LC-Method) $[M + H]^+$ |
|---|---|---|---|---|
| 7f | 6bf | 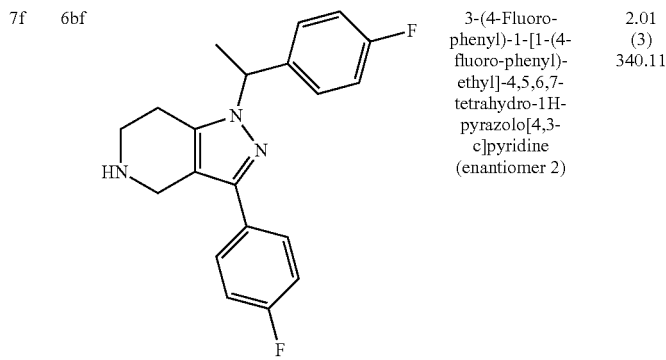 | 3-(4-Fluoro-phenyl)-1-[1-(4-fluoro-phenyl)-ethyl]-4,5,6,7-tetrahydro-1H-pyrazolo[4,3-c]pyridine (enantiomer 2) | 2.01 (3) 340.11 |

3-[1-(2,4-Difluoro-benzyl)-5-(3-methyl-oxetane-3-carbonyl)-4,5,6,7-tetrahydro-1H-pyrazolo[4,3-c]pyridin-3-yl]-benzonitrile (8a)

3-[1-(2,4-Difluoro-benzyl)-5-isobutyryl-4,5,6,7-tetrahydro-1H-pyrazolo[4,3-c]pyridin-3-yl]-benzonitrile (8b)

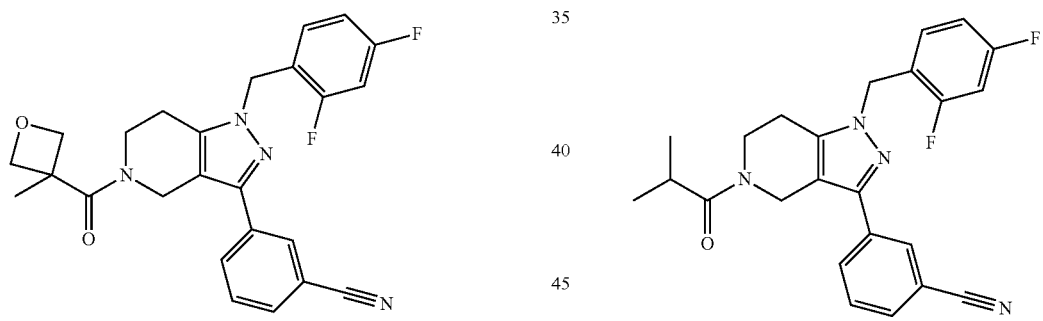

According to Scheme 6, Method A:

To a 10° C. cold solution of 3-[1-(2,4-Difluoro-benzyl)-4,5,6,7-tetrahydro-1H-pyrazolo[4,3-c]pyridin-3-yl]-benzonitrile, trifluoroacetate (7c) (0.055 g, 0.118 mmol) in N,N-dimethylformamide (2 ml) was added triethylamine (18 µl, 0.13 mmol), 1-hydroxybenzotriazole (17 mg, 0.124 mmol), 3-methyl-3-oxetane carboxylic acid (13.8 mg) and finally 1-ethyl-3-(3-dimethylaminopropyl)carbodiimide hydrochloride (24 mg, 0.124 mmol). The mixture was allowed to warm to 25° C. and stirred for 16 h and purified by reverse phase HPLC (CH3CN/water gradient with 0.1% trifluoroacetic acid) to give 38 mg of 3-[1-(2,4-Difluoro-benzyl)-5-(3-methyl-oxetane-3-carbonyl)-4,5,6,7-tetrahydro-1H-pyrazolo[4,3-c]pyridin-3-yl]-benzonitrile (8a).

$R_t$=1.23 min (LC-method 4). Detected mass: 449.27 [M+H$^+$]

According to Scheme 6, Method B:

A mixture of 3-[1-(2,4-Difluoro-benzyl)-4,5,6,7-tetrahydro-1H-pyrazolo[4,3-c]pyridin-3-yl]-benzonitrile (7c) (0.057 g, 0.163 mmol), K$_2$CO$_3$ (45 mg, 0.327 mmol) and isobutyryl chloride (21 mg, 0.196 mmol) in dry CH$_3$CN (1.5 ml) was stirred at 60° C. for 1 h. Water was added, the solution was extracted 3 times with CH$_2$Cl$_2$, the combined organic layers were washed once with brine, dried over Na$_2$SO$_4$, filtrated and the residue was purified by reverse phase HPLC (CH$_3$CN/water gradient with 0.1% trifluoroacetic acid) to give 48 mg of 3-[1-(2,4-Difluoro-benzyl)-5-isobutyryl-4,5,6,7-tetrahydro-1H-pyrazolo[4,3-c]pyridin-3-yl]-benzonitrile (8b).

$R_t$=1.18 min (LC-method 1). Detected mass: 421.29 [M+H$^+$]

3-[5-Cyclopropanecarbonyl-1-(2,4-difluoro-benzyl)-4,5,6,7-tetrahydro-1H-pyrazolo[4,3-c]pyridin-3-yl]-benzonitrile (8c)

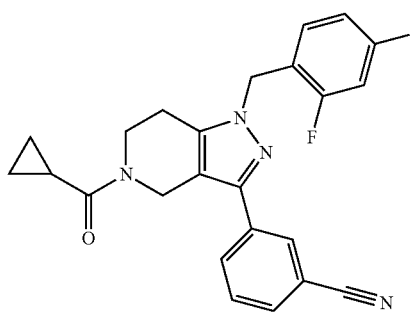

According to Scheme 6, Method C:

To a 0° C. cold mixture of 3-[1-(2,4-Difluoro-benzyl)-4,5,6,7-tetrahydro-1H-pyrazolo[4,3-c]pyridin-3-yl]-benzonitrile, hydrochloride salt (7c) (0.050 g, 0.129 mmol), NaHCO$_3$ (44 mg, 0.517 mmol), water (2 ml) and ethyl acetate (2 ml) was added cyclopropanecarbonyl chloride (13.5 mg, 0.129 mmol) and the mixture was stirred at 25° C. for 16 h. Water was added, the solution was extracted 2 times with ethyl acetate, the combined organic layers were washed once with brine, dried over MgSO4, filtrated and purified by reverse phase HPLC (CH$_3$CN/water gradient with 0.1% trifluoroacetic acid) to give 21 mg of 3-[5-Cyclopropanecarbonyl-1-(2,4-difluoro-benzyl)-4,5,6,7-tetrahydro-1H-pyrazolo[4,3-c]pyridin-3-yl]-benzonitrile (8c).

R$_t$=4.14 min (LC-method 13). Detected mass: 419.18 [M+H$^+$]

3-[5-(2-tert-Butoxy-acetyl)-1-(2,4-difluoro-benzyl)-4,5,6,7-tetrahydro-1H-pyrazolo[4,3-c]pyridin-3-yl]-benzonitrile (8d)

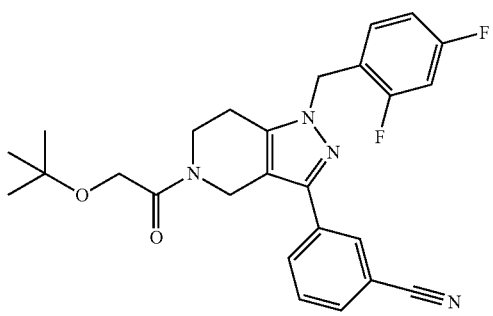 [SMILES: CC(C)(C)OCC(=O)N1CCc2c(c(-c3cccc(C#N)c3)nn2Cc2ccc(F)cc2F)C1]

According to Scheme 6, Method D:

To a 0° C. cold mixture of 3-[1-(2,4-Difluoro-benzyl)-4,5,6,7-tetrahydro-1H-pyrazolo[4,3-c]pyridin-3-yl]-benzonitrile (7c) (0.4 g, 1.142 mmol) and 2-tert-butoxyacetic acid (196 mg, 1.485 mmol) was added N,N-diisopropylethylamine (0.59 g, 4.57 mmol) and TOTU (O-(Cyano(ethoxycarbonyl)methylenamino)-1,1,3,3-tetramethyluronium tetrafluoroborate, 562 mg, 1.71 mmol) and the mixture was stirred at 25° C. for 1 h. The crude product was purified by reverse phase HPLC (CH$_3$CN/water gradient with 0.1% trifluoroacetic acid) to give 120 mg of 3-[5-(2-tert-Butoxy-acetyl)-1-(2,4-difluoro-benzyl)-4,5,6,7-tetrahydro-1H-pyrazolo[4,3-c]pyridin-3-yl]-benzonitrile (8d).

R$_t$=1.34 min (LC-method 4). Detected mass: 465.3 [M+H$^+$]

3-[1-(2,4-Difluoro-benzyl)-5-(3-methyl-3H-imidazole-4-carbonyl)-4,5,6,7-tetrahydro-1H-pyrazolo[4,3-c]pyridin-3-yl]-benzonitrile (8w)

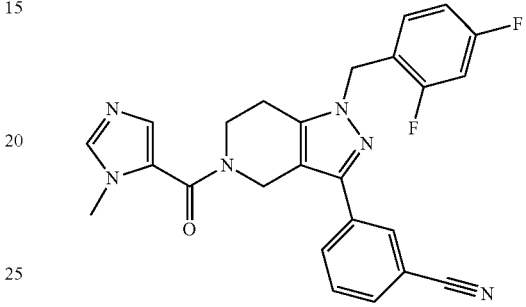

According to Scheme 6, Method E:

A mixture of 3-[1-(2,4-Difluoro-benzyl)-4,5,6,7-tetrahydro-1H-pyrazolo[4,3-c]pyridin-3-yl]-benzonitrile (7c) (0.04 g, 0.114 mmol), 3-Methyl-3H-imidazole-4-carbonyl chloride (0.083 g, 0.457 mmol) and triethylamine (138 mg, 1.37 mmol) in CH$_2$Cl$_2$ was stirred at 25° C. for 16 h. The crude product was purified by reverse phase HPLC (CH3CN/water gradient with 0.1% trifluoroacetic acid) to give 43 mg of 3-[1-(2,4-Difluoro-benzyl)-5-(3-methyl-3H-imidazole-4-carbonyl)-4,5,6,7-tetrahydro-1H-pyrazolo[4,3-c]pyridin-3-yl]-benzonitrile (8w).

R$_t$=3.53 min (LC-method 2). Detected mass: 459.24 [M+H$^+$]

1-[1-(2,4-Difluoro-benzyl)-3-(4-fluoro-phenyl)-6-methyl-1,4,6,7-tetrahydro-pyrazolo[4,3-c]pyridin-5-yl]-ethanone (8z)

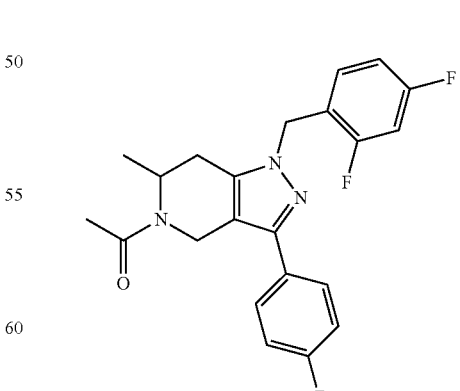

According to Scheme 6, Method F:

A mixture of 1-(2,4-Difluoro-benzyl)-3-(4-fluoro-phenyl)-6-methyl-4,5,6,7-tetrahydro-1H-pyrazolo[4,3-c]pyridine (7a) (0.53 g, 1.35 mmol), acetic anhydride (5.5 ml) and pyridine (5.5 ml) was stirred at 25° C. for 16 h. The mixture was poured on 50 ml water, extracted with 150 ml ethyl acetate, the combined organic layers were washed with 3 times 0.5 N NaOH (50 ml) and once with brine, dried over MgSO$_4$, filtrated and evaporated to dryness. The crude product was silica gel chromatography (eluting with heptane/ethyl acetate) to give 156 mg of 1-[1-(2,4-Difluoro-benzyl)-3-(4-fluoro-phenyl)-6-methyl-1,4,6,7-tetrahydro-pyrazolo[4,3-c]pyridin-5-yl]-ethanone (8z).

R$_t$=1.3 min (LC-method 4). Detected mass: 400.22 [M+H]$^+$

The examples in the following table were obtained according to Scheme 6 by following one of the methods described for the synthesis of 8a-8c (Method (A) according to 8a, Method (B) and Method (C) according to 8c). The acylating reagents are obvious to the man skilled in the art and therefore not mentioned.

| Comp. No. | SC (M) | Product | Chemical Name | R$_t$/[min] (LC-Method) [M + H]$^+$ |
|---|---|---|---|---|
| 8e | 7c (A) | | 3-[1-(2,4-Difluoro-benzyl)-5-(3-methanesulfonyl-benzoyl)-4,5,6,7-tetrahydro-1H-pyrazolo[4,3-c]pyridin-3-yl]-benzonitrile | 3.93 (13) 533.16 |
| 8f | 7b (C) | | [1-Benzyl-3-(4-fluoro-phenyl)-1,4,6,7-tetrahydro-pyrazolo[4,3-c]pyridin-5-yl]-(4-fluoro-phenyl)-methanone | 3.49 (8) 430.1 |
| 8g | 7b (C) | | [1-Benzyl-3-(4-fluoro-phenyl)-1,4,6,7-tetrahydro-pyrazolo[4,3-c]pyridin-5-yl]-(4-methoxy-phenyl)-methanone | 3.44 (8) 442.13 |

-continued

| Comp. No. | SC (M) | Product | Chemical Name | R$_t$/[min] (LC-Method) [M + H]$^+$ |
|---|---|---|---|---|
| 8h | 7b (C) | | [1-Benzyl-3-(4-fluoro-phenyl)-1,4,6,7-tetrahydro-pyrazolo[4,3-c]pyridin-5-yl]-phenyl-methanone | 3.45 (8) 412.1 |
| 8i | 7c (B) | | 3-[5-Cyclobutane-carbonyl-1-(2,4-difluoro-benzyl)-4,5,6,7-tetrahydro-1H-pyrazolo[4,3-c]pyridin-3-yl]-benzonitrile | 1.2 (1) 433.28 |
| 8j | 7c (B) | | 3-[5-Cyclopentane-carbonyl-1-(2,4-difluoro-benzyl)-4,5,6,7-tetrahydro-1H-pyrazolo[4,3-c]pyridin-3-yl]-benzonitrile | 1.23 (1) 447.23 |
| 8k | 7c (A) | | 3-[1-(2,4-Difluoro-benzyl)-5-(4-methanesulfonyl-benzoyl)-4,5,6,7-tetrahydro-1H-pyrazolo[4,3-c]pyridin-3-yl]-benzonitrile | 3.97 (13) 533.15 |

-continued

| Comp. No. | SC (M) | Product | Chemical Name | R$_t$/[min] (LC-Method) [M + H]$^+$ |
|---|---|---|---|---|
| 8l | 7c (C) | | 3-[1-(2,4-Difluoro-benzyl)-5-(tetra-hydro-pyran-4-carbonyl)-4,5,6,7-tetrahydro-1H-pyrazolo[4,3-c]pyridin-3-yl]-benzonitrile | 1.23 (4) 463.29 |
| 8m | 7c (C) | | 3-[1-(2,4-Difluoro-benzyl)-5-(tetrahydro-furan-3-carbonyl)-4,5,6,7-tetrahydro-1H-pyrazolo[4,3-c]pyridin-3-yl]-benzonitrile | 1.23 (4) 449.25 |
| 8n | 7c (B) | | 3-[1-(2,4-Difluoro-benzyl)-5-(2-methoxy-acetyl)-4,5,6,7-tetrahydro-1H-pyrazolo[4,3-c]pyridin-3-yl]-benzonitrile | 1.24 (4) 423.18 |
| 8o | 7c (B) | | 3-[1-(2,4-Difluoro-benzyl)-5-(2,2-dimethyl-propionyl)-4,5,6,7-tetrahydro-1H-pyrazolo[4,3-c]pyridin-3-yl]-benzonitrile | 1.36 (4) 435.31 |

| Comp. No. | SC (M) | Product | Chemical Name | R$_t$/[min] (LC-Method) [M + H]$^+$ |
|---|---|---|---|---|
| 8p | 7c (B) | | 3-[1-(2,4-Difluoro-benzyl)-5-propionyl-4,5,6,7-tetrahydro-1H-pyrazolo[4,3-c]pyridin-3-yl]-benzonitrile | 1.28 (4) 407.27 |
| 8q | 7c (A) | | 3-[1-(2,4-Difluoro-benzyl)-5-((S)-2-hydroxy-propionyl)-4,5,6,7-tetrahydro-1H-pyrazolo[4,3-c]pyridin-3-yl]-benzonitrile | 1.18 (4) 423.25 |
| 8r | 7b (C) | | 1-[1-Benzyl-3-(4-fluoro-phenyl)-1,4,6,7-tetrahydro-pyrazolo[4,3-c]pyridin-5-yl]-2-phenyl-ethanone | 3.47 (8) 426.12 |
| 8s | 7c (C) | | 3-[5-Butyryl-1-(2,4-difluoro-benzyl)-4,5,6,7-tetrahydro-1H-pyrazolo[4,3-c]pyridin-3-yl]-benzonitrile | 1.18 (1) 421.28 |

-continued

| Comp. No. | SC (M) | Product | Chemical Name | R$_t$/[min] (LC-Method) [M + H]$^+$ |
|---|---|---|---|---|
| 8t | 7c (C) | | 3-[1-(2,4-Difluoro-benzyl)-5-(pyridine-2-carbonyl)-4,5,6,7-tetrahydro-1H-pyrazolo[4,3-c]pyridin-3-yl]-benzonitrile | 4.07 (13) 456.17 |
| 8u | 7c (A) | | 3-[1-(2,4-Difluoro-benzyl)-5-(3-fluoro-pyridine-4-carbonyl)-4,5,6,7-tetrahydro-1H-pyrazolo[4,3-c]pyridin-3-yl]-benzonitrile | 4.49 (2) 474.19 |
| 8v | 7c (A) | | 3-[1-(2,4-Difluoro-benzyl)-5-(pyrimidine-4-carbonyl)-4,5,6,7-tetrahydro-1H-pyrazolo[4,3-c]pyridin-3-yl]-benzonitrile | 1.19 (4) 457.31 |
| 8x | 7c (E) | | 3-[1-(2,4-Difluoro-benzyl)-5-(1-methyl-1H-pyrazole-3-carbonyl)-4,5,6,7-tetrahydro-1H-pyrazolo[4,3-c]pyridin-3-yl]-benzonitrile | 4.49 (2) 459.24 |

-continued

| Comp. No. | SC (M) | Product | Chemical Name | R$_t$/[min] (LC-Method) [M + H]$^+$ |
|---|---|---|---|---|
| 8y | 7c (B) | | 3-(3-Cyano-phenyl)-1-(2,4-difluoro-benzyl)-1,4,6,7-tetrahydro-pyrazolo[4,3-c]pyridine-5-carboxylic acid ethyl ester | 1.35 (4) 423.2 |

3-(4-Fluoro-phenyl)-1-[(R)-1-(4-fluoro-phenyl)-ethyl]-5-methanesulfonyl-4,5,6,7-tetrahydro-1H-pyrazolo[4,3-c]pyridine, enantiomer 1 (9a)

Enantiomer 1

3-(4-Fluoro-phenyl)-1-[(R)-1-(4-fluoro-phenyl)-ethyl]-5-methanesulfonyl-4,5,6,7-tetrahydro-1H-pyrazolo[4,3-c]pyridine, enantiomer 2 (9b)

Enantiomer 2

According to Scheme 7:

To a mixture of 3-(4-Fluoro-phenyl)-1-[1-(4-fluoro-phenyl)-ethyl]-4,5,6,7-tetrahydro-1H-pyrazolo[4,3-c]pyridine (enantiomer 1) (7e) (0.120 g, 0.353 mmol) and triethylamine (0.135 ml, 1.06 mmol) in CH$_2$Cl$_2$ at 0° C. was added methanesulfonyl chloride (49 mg, 0.424 mmol) and the mixture was stirred at 25° C. for 16 h. The crude product was purified by reverse phase HPLC (CH$_3$CN/water gradient with 0.1% trifluoroacetic acid) to give 96 mg of 3-(4-Fluoro-phenyl)-1-[(R)-1-(4-fluoro-phenyl)-ethyl]-5-methanesulfonyl-4,5,6,7-tetrahydro-1H-pyrazolo[4,3-c]pyridine (9a).

R$_t$=3.58 min (LC-method 8). Detected mass: 418.09 [M+H$^+$]

3-(4-Fluoro-phenyl)-1-[(R)-1-(4-fluoro-phenyl)-ethyl]-5-methanesulfonyl-4,5,6,7-tetrahydro-1H-pyrazolo[4,3-c]pyridine, enantiomer 2 (9b) was obtained starting from 3-(4-Fluoro-phenyl)-1-[1-(4-fluoro-phenyl)-ethyl]-4,5,6,7-tetrahydro-1H-pyrazolo[4,3-c]pyridine (enantiomer 2) (7f) by following a similar reaction as used for synthesis of (9a).

R$_t$=3.58 min (LC-method 8). Detected mass: 418.09 [M+H$^+$]

3-(3-Cyano-phenyl)-1-(2,4-difluoro-benzyl)-1,4,6,7-tetrahydro-pyrazolo[4,3-c]pyridine-5-carboxylic acid isopropylamide (11a)

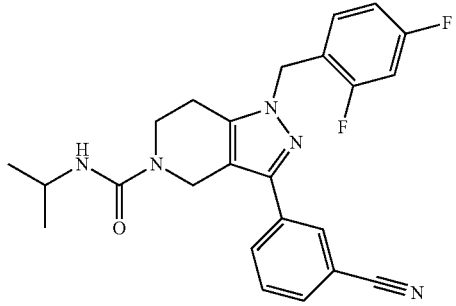 [SMILES: CC(C)NC(=O)N1CCc2c(c(-c3cccc(C#N)c3)nn2Cc2ccc(F)cc2F)C1]

According to Scheme 8:

To a mixture of 3-[1-(2,4-Difluoro-benzyl)-4,5,6,7-tetrahydro-1H-pyrazolo[4,3-c]pyridin-3-yl]-benzonitrile (7c) (0.060 g, 0.171 mmol) and triethylamine (138 mg, 1.37 mmol) at 0° C. was added isopropylisocyanate (17.5 mg, 0.21 mmol) and the mixture was stirred at room temperature for 16 h. The crude product was purified by reverse phase HPLC ($CH_3CN$/water gradient with 0.1% trifluoroacetic) to give 19 mg of 3-(3-Cyano-phenyl)-1-(2,4-difluoro-benzyl)-1,4,6,7-tetrahydro-pyrazolo[4,3-c]pyridine-5-carboxylic acid isopropylamide (11a).

$R_t$=1.16 min (LC-method 1). Detected mass: 436.25 $[M+H^+]$

The examples in the following table were obtained according to Scheme 9 by following a similar reaction as used for synthesis of (11a).

| Comp. No. | SC | Product | Chemical Name | $R_t$/[min] (LC-Method) $[M + H]^+$ |
|---|---|---|---|---|
| 11b | 7e | (structure, enantiomer 1) | 3-(4-Fluoro-phenyl)-1-[1-(4-fluoro-phenyl)-ethyl]-1,4,6,7-tetrahydro-pyrazolo[4,3-c]pyridine-5-carboxylic acid ethylamide, enantiomer 1 | 3.45 (8) 411.17 |
| 11c | 7f | (structure, enantiomer 2) | 3-(4-Fluoro-phenyl)-1-[1-(4-fluoro-phenyl)-ethyl]-1,4,6,7-tetrahydro-pyrazolo[4,3-c]pyridine-5-carboxylic acid ethylamide, enantiomer 2 | 3.45 (8) 411.16 |

| Comp. No. | SC | Product | Chemical Name | R$_t$/[min] (LC-Method) [M + H]$^+$ |
|---|---|---|---|---|
| 11f | 7e | 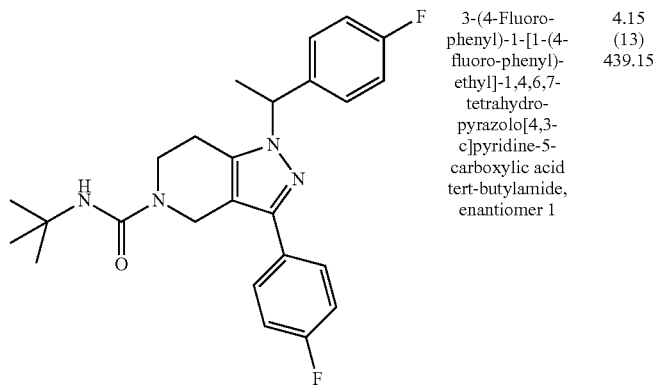<br>enantiomer 1 | 3-(4-Fluoro-phenyl)-1-[1-(4-fluoro-phenyl)-ethyl]-1,4,6,7-tetrahydro-pyrazolo[4,3-c]pyridine-5-carboxylic acid tert-butylamide, enantiomer 1 | 4.15 (13) 439.15 |
| 11h | 7c | 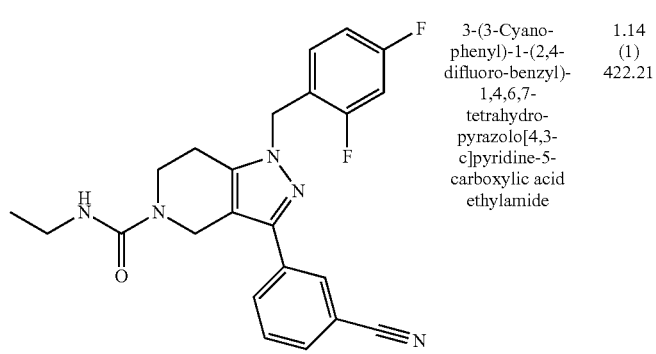 | 3-(3-Cyano-phenyl)-1-(2,4-difluoro-benzyl)-1,4,6,7-tetrahydro-pyrazolo[4,3-c]pyridine-5-carboxylic acid ethylamide | 1.14 (1) 422.21 |

3-(3-Cyano-phenyl)-1-(2,4-difluoro-benzyl)-1,4,6,7-tetrahydro-pyrazolo[4,3-c]pyridine-5-carboxylic acid methylamide (12a)

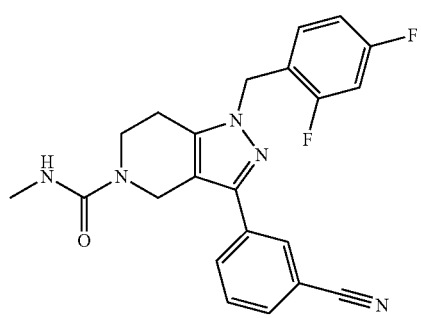

According to Scheme 9:

To a mixture of 3-[1-(2,4-Difluoro-benzyl)-4,5,6,7-tetrahydro-1H-pyrazolo[4,3-c]pyridin-3-yl]-benzonitrile (7c) (0.060 g, 0.171 mmol) and triethylamine (60 mg, 0.60 mmol) in $CH_2C_2$ at 0° C. was added para-nitrophenylchloroformate (38 mg, 0.188 mmol) and the mixture was stirred at 0° C. for 45 min. 2 M methylamine in tetrahydrofuran (2 ml, 4 mmol) was added and the mixture was stirred for 3 days at room temperature. The crude product was purified by reverse phase HPLC ($CH_3CN$/water gradient with 0.1% trifluoroacetic) to give 3.4 mg of 3-(3-Cyano-phenyl)-1-(2,4-difluoro-benzyl)-1,4,6,7-tetrahydro-pyrazolo[4,3-c]pyridine-5-carboxylic acid methylamide (12a).

$R_t$=1.11 min (LC-method 1). Detected mass: 408.15 [M+H$^+$]

The examples in the following table were obtained according to Scheme 10 by following a similar reaction as used for synthesis of (12a), but at a reaction temperature of 80° C.

| Comp. No. | SC | Product | Chemical Name | R_t[min] (Method) [M + H]+ |
|---|---|---|---|---|
| 12b | 7e | enantiomer 1 | {3-(4-Fluoro-phenyl)-1-[1-(4-fluoro-phenyl)-ethyl]-1,4,6,7-tetrahydro-pyrazolo[4,3-c]pyridin-5-yl}-morpholin-4-yl-methanone, enantiomer 1 | 3.74 (13) 453.11 |
| 12c | 7e | enantiomer 1 | {3-(4-Fluoro-phenyl)-1-[1-(4-fluoro-phenyl)-ethyl]-1,4,6,7-tetrahydro-pyrazolo[4,3-c]pyridin-5-yl}-((S)-3-hydroxy-pyrrolidin-1-yl)-methanone, enantiomer 1 | 3.37 (13) 453.11 |
| 12d | 7c | | 3-(3-Cyano-phenyl)-1-(2,4-difluoro-benzyl)-1,4,6,7-tetrahydro-pyrazolo[4,3-c]pyridine-5-carboxylic acid dimethylamide | 1.16 (1) 422.2 |
| 12e | 7c | | 3-(3-Cyano-phenyl)-1-(2,4-difluoro-benzyl)-1,4,6,7-tetrahydro-pyrazolo[4,3-c]pyridine-5-carboxylic acid (2-hydroxy-ethyl)-methyl-amide | 1.34 (14) 452.1 |

101

2-[5-Acetyl-1-(2,4-difluoro-benzyl)-4,5,6,7-tetrahydro-1H-pyrazolo[4,3-c]pyridin-3-yl]-isonicotinonitrile (13a)

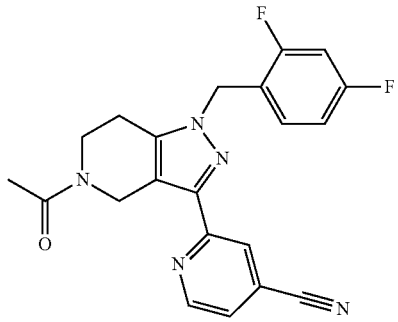 [SMILES: CC(=O)N1CCc2c(c(-c3cc(C#N)ccn3)nn2Cc2ccc(F)cc2F)C1]

According to Scheme 10:

To a solution of $Zn(CN)_2$ (39 mg, 0.335 mmol) and tetrakis(triphenylphosphine)palladium(0) (19 mg, 0.016 mmol) in dry N,N-dimethylformamide (0.6 ml) at 150° C. was slowly added a solution of 1-[3-(4-Bromo-pyridin-2-yl)-1-(2,4-difluoro-benzyl)-1,4,6,7-tetrahydro-pyrazolo[4,3-c]pyridin-5-yl]-ethanone (6j) (0.15 g, 0.335 mmol) in dry N,N-dimethylformamide (1 ml). The mixture was stirred at 150° C. for 3 h and then at 25° C. for 16 h. The mixture was diluted with methyl-tert-butylether, filtrated over Celite, washed with water, dried over $Na_2SO_4$, filtrated and evaporated to dryness. The residue was suspended in methanol, and the solid was filtrated off to give 67 mg of 2-[5-Acetyl-1-(2,4-difluoro-benzyl)-4,5,6,7-tetrahydro-1H-pyrazolo[4,3-c]pyridin-3-yl]-isonicotinonitrile (13a).

$R_t$=1.11 min (LC-method 1). Detected mass: 394.22 [M+H$^+$]

The examples in the following table were obtained according to Scheme 11 by following a similar reaction as described for the synthesis of 13a. Sometimes the products were purified by reverse phase HPLC ($CH_3CN$/water gradient with 0.1% trifluoroacetic acid).

102

3-[1-(2,4-Difluoro-benzyl)-5-(2-hydroxy-acetyl)-4,5,6,7-tetrahydro-1H-pyrazolo[4,3-c]pyridin-3-yl]-benzonitrile (14a)

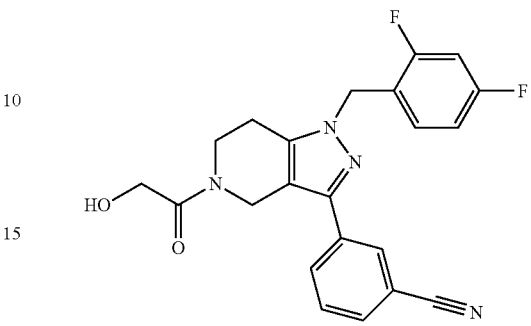

A solution of 3-[5-(2-tert-Butoxy-acetyl)-1-(2,4-difluoro-benzyl)-4,5,6,7-tetrahydro-1H-pyrazolo[4,3-c]pyridin-3-yl]-benzonitrile (8d) (90 mg, 0.193 mmol) and trifluoroacetic acid (221 mg, 1.94 mmol) in $CH_2Cl_2$ was stirred at 25° C. for 1 day. Solvents were evaporated and the residue purified by reverse phase HPLC ($CH_3CN$/water gradient with 0.1% trifluoroacetic acid) to give 48 mg of 3-[1-(2,4-Difluoro-benzyl)-5-(2-hydroxy-acetyl)-4,5,6,7-tetrahydro-1H-pyrazolo[4,3-c]pyridin-3-yl]-benzonitrile (14a).

$R_t$=1.19 min (method 4). Detected mass: 409.21 [M+H$^+$]

The following LC methods were used to analyze the exemplary embodiments:

Following abbreviations are used:

FA: formic acid

TFA: trifluoroacetic acid

ACN: acetonitrile

LC Method 1:

Stationary phase: Waters UPLC BEH C18 2,1*50 mm; 1.7µ

Gradient: $H_2O$+0.05% FA: ACN+0.035% FA 95:5 (0 min) to 5:95(1.1 min) to 5:95(1.7 min) to 95:5 (1.9 min) to 95:5 (2 min)

Flow: 0.9 mL/min, 55° C.

| Comp No. | SC | Product | Chemical Name | $R_t$/[min] (LC-Method) [M + H]$^+$ |
|---|---|---|---|---|
| 13b | 6w | | 6-[5-Acetyl-1-(2,4-difluoro-benzyl)-4,5,6,7-tetrahydro-1H-pyrazolo[4,3-c]pyridin-3-yl]-pyridine-2-carbonitrile | 1.11 (1) 394.22 |

LC Method 2:
Stationary phase: Waters XBridge C18 4.6*50 mm; 2.5μ
Gradient: H$_2$O+0.1% FA: AcN+0.1% FA 97:3 (0 min) to 40:60 (3.5 min) to 2:98(4 min) to 2:98(5 min) to 97:3 (5.2 min) to 97:3 (6.5 min);
Flow: 1.3 mL/min
LC Method 3:
Stationary phase: WatersXBridgeC18,4,6*50; 2.5μ
Gradient: H$_2$O+0.05% TFA: ACN+0.05% TFA 95:5(0 min) to 95:5(0.2 min) to 5:95(2.4 min) to 5:95(3.2 min) to 95:5 (3.3 min) to 95:5(4.0 min) Flow: 1.7 mL/min, 40° C.
LC Method 4:
Stationary phase: Waters UPLC BEH C18 2,1*50 mm; 1.7μ
Gradient: H$_2$O+0.1% FA: ACN+0.08% FA 95:5 (0 min) to 5:95(1.1 min) to 5:95(1.7 min) to 95:5 (1.8 min) to 95:5 (2 min)
Flow: 0.9 mL/min, 55° C.
LC Method 5:
Stationary phase: WatersXBridgeC18,4,6*50, 2.5μ
Gradient: H$_2$O+0.05% TFA: ACN+0.05% TFA 95:5(0 min) to 95:5(0.2 min) to 5:95(2.4 min) to 5:95(3.5 min) to 95:5 (3.6 min) to 95:5(4.5 min)
Flow: 1.7 mL/min, 50° C.
LC Method 6:
Stationary phase: WatersXBridgeC18,4,6*50, 2.5μ
Gradient: H$_2$O+0.05% TFA: ACN+0.05% TFA 95:5(0 min) to 5:95(2.6 min) to 5:95(3.0 min) to 95:5(3.1 min), to 95:5(4.0 min)
Flow: 1.7 mL/min, 40° C.
LC Method 7:
Stationary phase: Merck Chromolith FastGrad. RP-18e, 50×2 mm
Gradient: H$_2$O+0.05% TFA: ACN+0.05% TFA 98:2(0 min) to 98:2(0.2 min) to 2:98(2.4 min) to 2:98(3.2 min) to 98:2 (3.3 min) to 98:2(4 min)
Flow: 2 mL/min, 50° C.
LC Method 8:
Stationary phase: WatersXBridgeC18,4,6*50,2.5μ
Gradient: H$_2$O+0.05% TFA: ACN+0.05% TFA 95:5(0 min) to 95:5(0.3 min) to 5:95(3.5 min) to 5:95(4 min)
Flow: 1.3 ml/min, 40° C.
LC Method 9:
Stationary phase: Waters UPLC BEH C18 2,1*50 mm; 1.7μ
Gradient: H2O+0.05% FA: ACN+0.035% FA 98:2 (0 min) to 5:95(2 min) to 5:95(2.6 min) to 95:5 (2.7 min) to 95:5 (3 min)
Flow: 0.9 ml/min 55°
LC Method 10:
Stationary phase: 0.2 μl 110×20 LunaC18, 3μ
Gradient: 0 min 93% H$_2$O (0.05% TFA)-1.0 min-95% ACN; 95% ACN to 1.45 min; 7% ACN 1.50 min
Flow: 1 ml/min 55° C.
LC Method 11:
Stationary phase: Waters XBridge C18 4.6*50 mm; 2.5μ
Gradient: H$_2$O+0.1% FA: ACN+0.08% FA 97:3 (0 min) to 40:60 (3.5 min) to 2:98(4 min) to 2:98(5 min) to 97:3 (5.2 min) to 97:3 (6.5 min)
Flow: 1.3 ml, 45° C.
LC Method 12:
Stationary phase: YMC JSphere33*2, 4μ
Gradient: H$_2$O+0.05% FA: ACN+0.05% FA 95:5(0 min) to 95:5(0.5 min) to 5:95(3.5 min) to 5:95(4 min)
Flow: 1.3 ml/min, r.t.
LC Method 13:
Stationary phase: YMC-Pack JSphere H80 33*2.
Gradient: H$_2$O+0.05% TFA: CH$_3$OH+0.05% TFA 98:2(1 min) to 5:95(5.0 min) to 5:95(6.25 min)
Flow: 1.0 ml/min, r.t.
LC Method 14:
Stationary phase: YMC-JSphere-ODS-H80 (20×214μ)
Gradient: 0 min 96% H$_2$O (0.05% TFA) to 95% CH$_3$CN (2.4 min) to 4% CH$_3$CN (2.45 min)
Flow: 1.0 ml/min, 30° C.
LC Method 15:
Stationary phase: YMC JSphere33*2,4μ.
Gradient: (AcN+0.05% TFA): H2O+0.05% TFA; 5:95(0 min) to 5:95(0.5 min) to 95:5(3.5 min) to 95:5(4 min)
Flow: 1.3 ml/min Determination of the Activity on the TASK-1 Channel in *Xenopus* Oocytes Human TASK-1 channels were expressed in *Xenopus* oocytes. For this purpose, oocytes were isolated from *Xenopus laevis* and defoliculated. Subsequently, TASK-1-encoding RNA synthesized in vitro was injected into oocytes. After two days of TASK-1 protein expression, TASK-1 currents were measured by two-microelectrode voltage clamp. Data were acquired and analyzed using a TEC-10cx amplifier (NPI Electronic, Tamm, Germany) connected to an ITC-16 interface (Instrutech Corp., Long Island, USA) and Pulse software (HEKA Elektronik, Lambrecht, Germany). Oocytes were clamped to −90 mV and TASK-1 mediated currents were measured during 500 ms voltage pulses to 40 mV. Oocytes were continuously superfused with ND96 buffer containing: NaCl 96 mM, KCl 2 mM, CaCl$_2$ 1.8 mM, MgCl$_2$ 1 mM, HEPES 5 mM (pH adjusted to 7.4 with NaOH). All experiments were performed at room temperature.

Test substances were consecutively added to the bath solution at rising concentrations. Compound effects were calculated as the percentage inhibition of TASK-1 control current before compound application. IC50 values were obtained by fitting the data to the general dose-response equation.

The following products/compounds were tested in said assay by using the respective form (salt or free base) obtained as in the examples described above and the following activities were measured (IC50 values or inhibition (in %) at 5 μM).

| Example No. | IC50 (μM) | Inhibition (%) at 5 μM |
| --- | --- | --- |
| 6a | 0.095 | |
| 6ab | | 76% |
| 6ac | | 80% |
| 6ad | | 86% |
| 6ae | | 84% |
| 6af | | 72% |
| 6ag | | 75% |
| 6ah | | 53% |
| 6ai | | 79% |
| 6aj | | 76% |
| 6ak | 0.27 | |
| 6al | | 75% |
| 6am | 0.114 | |
| 6an | 0.187 | |
| 6ao | 0.258 | |
| 6ap | 0.285 | |
| 6aq | 0.359 | |
| 6ar | 0.552 | |
| 6as | 0.659 | |
| 6at | 0.72 | |
| 6av | 0.911 | |
| 6aw | 0.947 | |
| 6ax | 0.975 | |
| 6ay | | 86% |
| 6az | | 89% |
| 6b | 0.172 | |
| 6ba | | 81% |
| 6bb | | 82% |
| 6bc | | 70% |

-continued

| Example No. | IC50 (µM) | Inhibition (%) at 5 µM |
|---|---|---|
| 6bd | <10 | |
| 6be | 0.5 | |
| 6bf | 0.5 | |
| 6bg | 0.398 | |
| 6bh | <10 | |
| 6bi | 1.645 | |
| 6bj | 1.16 | |
| 6bk | 1.15 | |
| 6bl | 0.966 | |
| 6bm | 0.251 | |
| 6bn | | 81% |
| 6c | 0.215 | |
| 6d | 0.422 | |
| 6f | 0.598 | |
| 6g | 0.0995 | |
| 6h | 0.19 | |
| 6i | 0.216 | |
| 6j | <10 | |
| 6k | | 78% |
| 6m | 2.441 | |
| 6n | 0.091 | |
| 6o | <10 | |
| 6p | | 88% |
| 6q | | 70% |
| 6r | | 79% |
| 6s | | 83% |
| 6t | | 62% |
| 6u | | 89% |
| 6v | | 73% |
| 6w | <10 | |
| 6x | | 82% |
| 6y | | 86% |
| 6z | | 75% |
| 8a | 0.276 | |
| 8b | 0.019 | |
| 8c | 0.047 | |
| 8d | | 75% |
| 8e | 1.625 | |
| 8f | 1.28 | |
| 8g | 3.264 | |
| 8h | 2.399 | |
| 8i | 0.064 | |
| 8j | 0.722 | |
| 8k | 0.906 | |
| 8l | 0.585 | |
| 8m | 0.89 | |
| 8n | | 80% |
| 8o | 0.131 | |
| 8p | 0.53 | |
| 8q | 0.756 | |
| 8r | 1.138 | |
| 8s | <10 | |
| 8t | 0.246 | |
| 8u | 0.416 | |
| 8v | 0.864 | |
| 8w | 1.149 | |
| 8x | 1.878 | |
| 8y | | 77% |
| 8z | 0.511 | |
| 9a | 0.54 | |
| 9b | 0.611 | |
| 11a | | 76% |
| 11b | 1.52 | |
| 11c | 1.167 | |
| 11f | | 58% |
| 11h | | 91% |
| 12a | 0.38 | |
| 12b | 0.511 | |
| 12c | 0.734 | |
| 12d | | 74% |
| 12e | | 65% |
| 13a | 0.422 | |
| 13b | 0.462 | |
| 14a | <10 | |

Investigation of the Refractory Period and the Left-Atrial Vulnerability in the Pig The compounds were tested for prolongation of the refractory period and antiarrhythmic activity on the atrium of the anesthetized pig as described in the literature (Knobloch et al. 2002. Naunyn-Schmiedberg's Arch. Pharmacol. 366; 482-487). Here the anti-arrhythmic action relates to the inhibition of the occurrence of episodes of arrhythmias which are induced by a prematurely placed extra-stimulus (S2) in the left atrium (=left-atrial vulnerability). The refractory period values are stated in percent of the basal values 15 minutes after injection. Mean values for the refractory periods are shown from three rates (150, 200 and 250/min). The inhibitory values for the inhibition of episodes of arrhythmias refer to 3 measurements (3 timepoints) before administration vs. 3 measurements during the first hour after administration of the compounds.

The action of 3-[5-Acetyl-1-(2,4-difluoro-benzyl)-4,5,6,7-tetrahydro-1H-pyrazolo[4,3-c]pyridin-3-yl]-benzonitrile (6a) on the refractory period of the left atrium and antiarrhythmic activity in the anesthetized pig after a bolus administration of 1 mg/kg is shown in table 1. From the results shown in table 1, it is seen that it was possible to prevent 61% of the induced arrhythmias.

TABLE 1

| | Mean value |
|---|---|
| % increase in the refractory period | 14% |
| % inhibition of the arrhythmias | 61% |
| Number of animals | n = 3 |

The invention claimed is:
1. A compound of the formula I

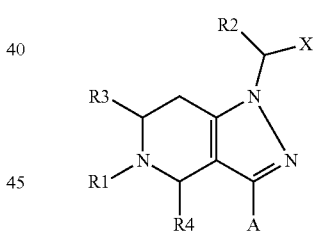

wherein
A is $(C_6-C_{10})$-aryl optionally substituted with 1-3 groups selected independently from F, Cl, Br, CN, $(C_1-C_6)$-alkyl-, $(C_1-C_6)$-alkyl-O— and $(C_1-C_6)$-alkyl-S—, wherein one or more hydrogen atoms of the alkyl moieties are optionally replaced by fluorine;
X is $(C_6-C_{10})$-aryl or a five- or six-membered heteroaryl comprising 1-3 heteroatoms selected from the group N, O and S, wherein the aryl and heteroaryl are optionally substituted with 1-3 groups selected independently from F, Cl, Br, CN, $(C_1-C_6)$-alkyl-, $(C_1-C_6)$-alkyl-O—, $(C_1-C_6)$-alkyl-S—, $(C_1-C_6)$-alkyl-O—C(O)— and $(C_1-C_6)$-alkyl-$SO_2$—, wherein one or more hydrogen atoms of the alkyl moieties are optionally replaced by fluorine;
R1 is R5-C(=O)— or $(C_1-C_6)$-alkyl-$SO_2$—;
R2 is H, $(C_1-C_6)$-alkyl- or $(C_3-C_6)$-cycloalkyl-;
R3 is H or $(C_1-C_4)$-alkyl-;
R4 is H or $(C_1-C_4)$-alkyl-;
or R3 and R4 together form a $(C_2-C_3)$-alkylene bridge;

R5 is H, $(C_1-C_6)$-alkyl-, $(C_3-C_6)$-cycloalkyl-, $(C_1-C_6)$-alkyl-O—, $(C_1-C_6)$-alkyl-S—, $(C_1-C_6)$-alkyl-O—$(C_1-C_6)$-alkyl-, HO—$(C_1-C_6)$-alkyl-, $(C_3-C_6)$-cycloalkyl-$(C_1-C_6)$-alkyl-, $(C_6-C_{10})$-aryl-, $(C_6-C_{10})$-aryl-$(C_1-C_6)$-alkyl-, R7R6N—, heteroaryl, heteroaryl-$(C_1-C_6)$-alkyl- or aliphatic heterocycle,
    wherein one or more hydrogen atoms of the alkyl moieties are optionally replaced by fluorine, and
    wherein the aliphatic heterocycle is selected from the group of morpholinyl, piperidinyl, pyrrolidinyl and four- to seven-membered aliphatic heterocycles comprising an oxygen atom, each optionally substituted with 1 to 3 substituents independently selected from F, OH, $(C_1-C_6)$-alkyl-O— and $(C_1-C_6)$-alkyl-, and
    wherein the heteroaryl residues are five- or six-membered ring systems comprising 1-3 heteroatoms selected from the group N, O and S, and
    wherein the aryl and heteroaryl are optionally substituted with 1-3 groups selected independently from F, Cl, Br, $CF_3$, CN, $(C_1-C_2)$-alkyl-$SO_2$—;
R6 is H, $(C_1-C_6)$-alkyl- or $(C_3-C_6)$-cycloalkyl-, wherein one hydrogen atom of the alkyl group is optionally replaced by hydroxy or $(C_1-C_6)$-alkyl-O—, and wherein one or more hydrogen atoms of the alkyl group are optionally replaced by fluorine; and
R7 is H or $(C_1-C_6)$-alkyl-, wherein one or more hydrogen atoms of the alkyl group are optionally replaced by fluorine;
or a stereoisomer, stereoisomeric mixture or pharmaceutically acceptable salt thereof;
    with the proviso if R5 is methyl and R2, R3 and R4 are H and A is 4-fluoro-phenyl, the residue X is not phenyl, 4-fluoro-phenyl, 4-chloro-phenyl, 4-methyl-phenyl, 4-methoxy-phenyl, 4-acetoxyphenyl, 2-chloro-phenyl, or 3,4-dichlorophenyl; and
    with the proviso if R5 is methyl and R2, R3 and R4 are H and X is a phenyl residue, the residue A is not phenyl, 4-fluoro-phenyl, 4-chloro-phenyl, 4-methyl-phenyl, 4-ethyloxy-phenyl, 3-trifluoromethyl-phenyl or 4-methylthiophenyl; and
    with the proviso if R5 is methyl and R2 is methyl and R3 and R4 are H and A is 4-fluoro-phenyl, the residue X is not phenyl.

2. The compound according to claim 1, wherein
A is phenyl, optionally substituted with 1-3 groups selected independently from F, Cl, Br, CN, $(C_1-C_6)$-alkyl-, $(C_1-C_6)$-alkyl-O— and $(C_1-C_6)$-alkyl-S—, wherein one or more hydrogen atoms of the alkyl moieties are optionally replaced by fluorine;
X is a five- or six-membered heteroaryl comprising 1-3 heteroatoms selected from the group N, O and S, wherein the heteroaryl group is optionally substituted with 1-3 residues selected independently from F, Cl, Br, CN, $(C_1-C_6)$-alkyl-, $(C_1-C_6)$-alkyl-O—, $(C_1-C_6)$-alkyl-S—, $(C_1-C_6)$-alkyl-O—C(O)— and $(C_1-C_6)$-alkyl-$SO_2$—, wherein one or more hydrogen atoms of the alkyl moieties are optionally replaced by fluorine;
R1 is R5-C(=O)— or $(C_1-C_6)$-alkyl-$SO_2$—;
R2 is H, $(C_1-C_4)$-alkyl- or $(C_3-C_6)$-cycloalkyl-;
R3 is H or $(C_1-C_2)$-alkyl-;
R4 is H or $(C_1-C_2)$-alkyl-;
or R3 and R4 together form a $(C_2-C_3)$-alkylene bridge;
R5 is H, $(C_1-C_6)$-alkyl-, $(C_3-C_6)$-cycloalkyl-, $(C_1-C_6)$-alkyl-O—, $(C_1-C_6)$-alkyl-S—, $(C_1-C_6)$-alkyl-O—$(C_1-C_6)$-alkyl-, HO—$(C_1-C_6)$-alkyl-, $(C_3-C_6)$-cycloalkyl-$(C_1-C_6)$-alkyl-, $(C_6-C_{10})$-aryl-, $(C_6-C_{10})$-aryl-$(C_1-C_6)$-alkyl-, R7R6N—, heteroaryl, heteroaryl-$(C_1-C_6)$-alkyl- or aliphatic heterocycle,
    wherein one or more hydrogen atoms of the alkyl moieties are optionally replaced by fluorine, and
    wherein the aliphatic heterocycle is selected from the group of morpholinyl, piperidinyl, pyrrolidinyl and four- to seven-membered aliphatic heterocycles comprising an oxygen atom, and is optionally substituted with 1 to 3 substituents independently selected from the group of F, OH, $(C_1-C_6)$-alkyl-O— and $(C_1-C_6)$-alkyl-, and
    wherein the heteroaryl residues are five- or six-membered ring systems, comprising 1-3 heteroatoms selected from the group N, O and S, and
    wherein aryl and heteroaryl are optionally substituted with 1-3 groups selected independently from F, Cl, Br, $CF_3$, $(C_1-C_6)$-alkyl-, $(C_1-C_6)$-alkyl-O—, CN and $(C_1-C_2)$-alkyl-$SO_2$—;
R6 is H, $(C_1-C_6)$-alkyl- or $(C_3-C_6)$-cycloalkyl-, wherein one hydrogen atom of the alkyl group are optionally replaced by —OH or $(C_1-C_6)$-alkyl-O—, and
    wherein one or more hydrogen atoms of the alkyl group are optionally replaced by fluorine; and
R7 is H or $(C_1-C_6)$-alkyl-M wherein one or more hydrogen atoms of the alkyl group are optionally replaced by fluorine;
or a stereoisomer, stereoisomeric mixture or pharmaceutically acceptable salt thereof.

3. The compound according to claim 1, wherein
A is phenyl, optionally substituted with 1-3 groups selected independently from F, Cl, Br, CN, $(C_1-C_4)$-alkyl-, $(C_1-C_4)$-alkyl-O— and $(C_1-C_4)$-alkyl-S—, wherein one or more hydrogen atoms of the alkyl moieties are optionally replaced by fluorine;
X is a five- or six-membered heteroaryl, selected from the group consisting of pyridine-2-yl, pyridine-3-yl, pyridine-4-yl, thiophen-2-yl, thiophen-3-yl, thiazol-2-yl, thiazol-4-yl and thiazol-5-yl, each optionally substituted with 1-3 residues selected independently from F, Cl, Br, CN, $(C_1-C_6)$-alkyl-, $(C_1-C_6)$-alkyl-O— and $(C_1-C_6)$-alkyl-S—, $(C_1-C_6)$-alkyl-O—C(O)— and $(C_1-C_6)$-alkyl-$SO_2$—, wherein one or more hydrogen atoms of the alkyl moieties are optionally replaced by fluorine;
R1 is R5-C(=O)— or $(C_1-C_2)$-alkyl-$SO_2$—;
R2 is H, $(C_1-C_2)$-alkyl- or cyclopropyl-;
R3 is H or methyl-;
R4 is H or methyl-;
or R3 and R4 together form an ethylene bridge;
R5 is H, $(C_1-C)$-alkyl-, $(C_3-C_6)$-cycloalkyl-, $(C_1-C_2)$-alkyl-O—, $(C_1-C_2)$-alkyl-S—, $(C_1-C_4)$-alkyl-O-methyl-, HO—$(C_1-C_2)$-alkyl-, $(C_3-C_6)$-cycloalkyl-$(C_1-C_2)$-alkyl-, phenyl, phenyl-$(C_1-C_2)$-alkyl-, R7R6N—, heteroaryl, heteroaryl-$(C_1-C_4)$-alkyl- or aliphatic heterocycle,
    wherein one or more hydrogen atoms of the alkyl moieties are optionally replaced by fluorine, and
    wherein the aliphatic heterocycle is selected from the group of morpholinyl, piperidinyl, pyrrolidinyl, oxetanyl, tetrahydrofuranyl, and tetrahydropyranyl, each optionally substituted with 1 or 2 substituents independently selected from the group of F, OH, $(C_1-C_2)$-alkyl-O— and $(C_1-C_4)$-alkyl-, and
    wherein the phenyl residue is optionally substituted with 1-3 groups selected independently from F, Cl, Br, $CF_3$, $(C_1-C_4)$-alkyl-, $(C_1-C_4)$-alkyl-O—, CN and $(C_1-C_2)$-alkyl-$SO_2$—, and wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and pyrazin-3-yl, each optionally substituted with 1 or 2 groups selected independently from F, Cl, Br, $CF_3$, $(C_1-C_4)$-alkyl-, $(C_1-C_4)$-alkyl-O—, CN and $(C_1-C_2)$-alkyl-$SO_2$—;

R6 is H, $(C_1-C_4)$-alkyl- or cyclopropyl, wherein one hydrogen atom of the alkyl group is optionally replaced by hydroxy, methoxy or ethoxy; and R7 is H, methyl or ethyl;

or a stereoisomer, stereoisomeric mixture or pharmaceutically acceptable salt thereof.

4. The compound according to claim 1, wherein

A is phenyl, optionally substituted with 1 or 2 groups selected independently from F, Cl, Br, CN, $(C_1-C_4)$-alkyl-, $CF_3$, $CF_2H$, $CFH_2$, methoxy, ethoxy, $OCF_3$, and $(C_1-C_2)$-alkyl-S—;

X is a five- or six-membered heteroaryl selected from the group consisting of pyridine-2-yl, pyridine-3-yl, pyridine-4-yl, thiophen-2-yl, thiophen-3-yl, thiazol-2-yl, thiazol-4-yl, thiazol-5-yl, each optionally substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$-;

R1 is R5-C(=O)— or $(C_1-C_2)$-alkyl-$SO_2$—;

R2 is H, methyl, ethyl or cyclopropyl;

R3 and R4 are H, and

R5 is methyl, ethyl, n-propyl, isopropyl, n-butyl, isobutyl, tert.-butyl, cyclopropyl or cyclobutyl;

or a stereoisomer, stereoisomeric mixture or pharmaceutically acceptable salt thereof.

5. The compound according to claim 1, wherein

A is phenyl, optionally substituted with 1-3 residues selected independently from F, Cl, Br, CN, $(C_1-C_4)$-alkyl-, $(C_1-C_4)$-alkyl-O— and $(C_1-C_4)$-alkyl-S—, wherein one or more hydrogen atoms of the alkyl moieties are optionally replaced by fluorine;

X is phenyl, optionally substituted with 1, 2 or 3 residues selected independently from F, Cl, Br, CN, $(C_1-C_4)$-alkyl-, $(C_1-C_4)$-alkyl-O—, $(C_1-C_4)$-alkyl-S—, $(C_1-C_4)$-alkyl-O—C(O)— and $(C_1-C_4)$-alkyl-$SO_2$—, wherein one or more hydrogen atoms of the alkyl moieties are optionally replaced by fluorine;

R1 is R5-C(=O)— or $(C_1-C_6)$-alkyl-$SO_2$—;

R2 is H, $(C_1-C_6)$-alkyl- or $(C_3-C_6)$-cycloalkyl-;

R3 is H or $(C_1-C_4)$-alkyl-;

R4 is H or $(C_1-C_4)$-alkyl-;

or R3 and R4 together form a $(C_2-C_3)$-alkylene bridge;

R5 is H, $(C_1-C_6)$-alkyl-, $(C_3-C_6)$-cycloalkyl-, $(C_1-C_6)$-alkyl-O—, $(C_1-C_6)$-alkyl-S—, $(C_1-C_6)$-alkyl-O—$(C_1-C_6)$-alkyl-, HO—$(C_1-C_6)$-alkyl-, $(C_3-C_6)$-cycloalkyl-$(C_1-C_6)$-alkyl-, $(C_6-C_{10})$-aryl-, $(C_6-C_{10})$-aryl-$(C_1-C_6)$-alkyl-, R7R6N—, heteroaryl, heteroaryl-$(C_1-C_6)$-alkyl- or aliphatic heterocycle, wherein one or more hydrogen atoms of the alkyl moieties are optionally replaced by fluorine, and wherein the aliphatic heterocycle is selected from the group of morpholinyl, piperidinyl, pyrrolidinyl and four- to seven-membered aliphatic heterocycles comprising an oxygen atom, and is optionally substituted with 1 to 3 substituents selected from the group of F, OH, $(C_1-C_6)$-alkyl-O— and $(C_1-C_6)$-alkyl-, and wherein the heteroaryl residues are five- or six-membered ring systems, comprising 1-3 heteroatoms selected from the group N, O and S, and wherein the aryl and heteroaryl are optionally substituted with 1-3 groups selected independently from F, Cl, Br, $CF_3$, $(C_1-C_6)$-alkyl-O—, CN and $(C_1-C_2)$-alkyl-$SO_2$—;

R6 is H, $(C_1-C_6)$-alkyl- or $(C_3-C_6)$-cycloalkyl-, wherein one hydrogen atom of the alkyl group is optionally replaced hydroxy or $(C_1-C_6)$-alkyl-O—, and wherein one or more hydrogen atoms of the alkyl group are optionally replaced by fluorine;

R7 is H or $(C_1-C_6)$-alkyl-, wherein one or more hydrogen atoms of the alkyl group are optionally replaced by fluorine;

or a stereoisomer, stereoisomeric mixture or pharmaceutically acceptable salt thereof;

with the proviso if R5 is methyl and R2, R3 and R4 are H and A is 4-fluoro-phenyl, the residue X is not phenyl, 4-fluoro-phenyl, 4-chloro-phenyl, 4-methyl-phenyl, 4-methoxy-phenyl, 4-acetoxyphenyl, 2-chloro-phenyl, or 3,4-dichlorophenyl; and with the proviso if R5 is methyl and R2, R3 and R4 are H and X is a phenyl residue, the residue A is not phenyl, 4-fluoro-phenyl, 4-chloro-phenyl, 4-methyl-phenyl, 4-ethyloxy-phenyl, 3-trifluoromethyl-phenyl or 4-methylthiophenyl; and with the proviso if R5 is methyl and R2 is methyl and R3 and R4 are H and A is 4-fluoro-phenyl, the residue X is not phenyl.

6. The compound according to claim 5, wherein

A is phenyl, substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X is phenyl, substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—;

R1 is R5-C(=O)— or methyl-$SO_2$—;

R2 is H, $(C_1-C_2)$-alkyl- or cyclopropyl-;

R3 is H or methyl-;

R4 is H or methyl-;

or R3 and R4 together form an ethylene bridge;

R5 is heteroaryl or heteroaryl-$(C_1-C_6)$-alkyl-, wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and pyrazin-3-yl, each optionally substituted with 1 or 2 residues selected independently from F, Cl, Br, $CF_3$, methyl, ethyl, methoxy, ethoxy, CN and methyl-$SO_2$—;

or R5 is H;

or R5 is cyclopropyl, cyclobutyl, cyclopentyl, cyclohexyl or $(C_3-C_6)$-cycloalkyl-$(C_1-C_2)$-alkyl-;

or R5 is $(C_1-C_2)$-alkyl-O— or $(C_1-C_2)$-alkyl-S—;

or R5 is $(C_1-C_4)$-alkyl-O-methyl- or HO—$(C_1-C_2)$-alkyl-;

or R5 is phenyl or phenylmethyl-, wherein the phenyl residues are optionally substituted with 1-3 residues selected independently from F, Cl, Br, $CF_3$, $(C_1-C_2)$-alkyl-, $(C_1-C_2)$-alkyl-O—, CN and methyl-$SO_2$—, wherein one or more hydrogen atoms of the alkyl moieties are optionally replaced by fluorine;

or R5 is R7R6N—, wherein R6 is H, $(C_1-C_4)$-alkyl- or cyclopropyl-, wherein one hydrogen atom of the alkyl group is optionally replaced by hydroxy, methoxy or ethoxy, and R7 is H, methyl- or ethyl-;

or R5 is an aliphatic heterocycle, wherein the aliphatic heterocycle is selected from the group of oxetanyl, tetrahydrofuranyl, tetrahydropyranyl, morpholinyl, piperidinyl and pyrrolidinyl, wherein the aliphatic heterocycle is optionally substituted with 1 or 2 substituents selected from the group of F, —OH, $(C_1-C_2)$-alkyl-O— and $(C_1-C_4)$-alkyl-, wherein one or more hydrogen atoms of the alkyl groups are optionally replaced by fluorine;

or a stereoisomer, stereoisomeric mixture or pharmaceutically acceptable salt thereof.

7. The compound according to claim 5, wherein

A is phenyl, substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X is phenyl, is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—;

R1 is R5-C(=O)—;

R2 is H, $(C_1-C_2)$-alkyl- or cyclopropyl-;

R3 is H or methyl-;

R4 is H or methyl-;

or R3 and R4 together form an ethylene bridge; and

R5 is $(C_2-C_4)$-alkyl;

or R5 is methyl;

or a stereoisomer, stereoisomeric mixture or pharmaceutically acceptable salt thereof;

with the proviso if R5 is methyl and R2, R3 and R4 are H and A is 4-fluoro-phenyl, the residue X is not phenyl, 4-fluoro-phenyl, 4-chloro-phenyl, 4-methyl-phenyl, 4-methoxy-phenyl, 4-acetoxyphenyl, 2-chloro-phenyl, or 3,4-dichlorophenyl.

8. The compound according to claim 1, wherein

A is $(C_6-C_{10})$-aryl, optionally substituted with 1-3 groups selected independently from F, Cl, Br, CN, $(C_1-CO-$alkyl-, $(C_1-C_6)$-alkyl-O— and $(C_1-C_6)$-alkyl-S—, wherein one or more hydrogen atoms of the alkyl moieties are optionally replaced by fluorine;

X is $(C_6-C_{10})$-aryl or a five- or six-membered heteroaryl, comprising 1-3 heteroatoms selected from the group N, O and S, wherein the aryl and heteroaryl are optionally substituted with 1-3 groups selected independently from F, Cl, Br, CN, $(C_1-C_6)$-alkyl-, $(C_1-C_6)$-alkyl-O— and $(C_1-C_6)$-alkyl-S—, $(C_1-C_6)$-alkyl-O—C(O)— and $(C_1-C_6)$-alkyl-$SO_2$—, wherein one or more hydrogen atoms of the alkyl moieties are optionally replaced by fluorine;

R1 is R5-C(=O)— or $(C_1-C_6)$-alkyl-$SO_2$—;

R2 is H, $(C_1-C_6)$-alkyl- or $(C_3-C_6)$-cycloalkyl-;

R3 is H or $(C_1-C_4)$-alkyl-;

R4 is H or $(C_1-C_4)$-alkyl-;

or R3 and R4 together form a $(C_2-C_3)$-alkylene bridge;

R5 is heteroaryl or heteroaryl-$(C_1-C_6)$-alkyl-, wherein the heteroaryl residues are five- or six-membered ring systems, comprising 1-3 heteroatoms selected from the group N, O and S, and are optionally substituted with 1-3 residues selected independently from F, Cl, Br, $CF_3$, $(C_1-C_6)$-alkyl-, $(C_1-C_6)$-alkyl-O—, CN and $(C_1-C_2)$-alkyl-$SO_2$—, wherein one or more hydrogen atoms of the alkyl moieties are optionally replaced by fluorine, with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl;

or R5 is methyl, with the proviso if in compounds of formula I R2, R3 and R4 are hydrogen and X is a 2,4-difluorophenyl residue A is not 2 fluoro-phenyl, 3-fluoro-phenyl, 4-fluorophenyl, 3-cyano-phenyl, 3-methoxy-phenyl, 3-trifluormethoxy-phenyl, or 2-fluoro-5-methoxy-phenyl, and with the proviso if in compounds of formula I R2, R3 and R4 are hydrogen and X is a 3-cyanophenyl residue A is not a 4-fluorophenyl residue, and with the proviso if in compounds of formula I R3 is methyl, R2 and R4 are hydrogen and X is a 2,4-difluoro-phenyl residue A is not a 4-fluoro-phenyl, and with the proviso if in compounds of formula I R2, R3 and R4 are hydrogen and X is phenyl A is not phenyl, 3-trifluoromethyl-phenyl, 4-fluoro-phenyl, 4-chloro-phenyl, 4-methyl-phenyl, 4-ethyloxy-phenyl, 4-acetoxyphenyl or 4-methylthiophenyl, and with the proviso if in compounds of formula I R2, R3 and R4 are hydrogen and A is 4-fluoro-phenyl X is not phenyl, 2-chloro-phenyl, 3,4-dichloro-phenyl, 4-chloro-phenyl, 4-fluoro-phenyl, 4-methyl-phenyl, 4-methoxy-phenyl, or 4-ethyloxy-phenyl, and with the proviso if R2 is methyl, and R3 and R4 are H and A is 4-fluoro-phenyl, the residue X is not phenyl;

or R5 is H, $(C_2-C_6)$-alkyl, $CF_3$, $CF_2H$ or $CFH_2$, wherein one or more hydrogen atoms of the alkyl residue are optionally replaced by fluorine;

or R5 is $(C_3-C_6)$-cycloalkyl or $(C_3-C_6)$-cycloalkyl-$(C_1-C_4)$-alkyl-, with the proviso if in compounds of formula I A is a 3-cyanophenyl residue and X a 2,4-difluorophenyl residue R5 is not cyclopropyl;

or R5 is $(C_1-C_4)$-alkyl-O— or $(C_1-C_4)$-alkyl-S—, wherein one or more hydrogen atoms of the alkyl moieties are optionally replaced by fluorine;

or R5 is $(C_1-C_4)$-alkyl-O—$(C_1-C_2)$-alkyl- or HO—$(C_1-C_4)$-alkyl-;

or R5 is phenyl or phenyl-$(C_1-C_4)$-alkyl-, wherein the phenyl residue is optionally substituted with 1-3 residues selected independently from F, Cl, Br, $CF_3$, $(C_1-C_6)$-alkyl-, $(C_1-C_6)$-alkyl-O—, CN and $(C_1-C_2)$-alkyl-$SO_2$—, and wherein one or more hydrogen atoms of the alkyl moieties are optionally replaced by fluorine, with the proviso if in compounds of formula I A is a 3-cyanophenyl residue and X a 2,4-difluorophenyl residue R5 is not 3-methylsulfonyl-phenyl or 4-methylsulfonyl-phenyl;

or R5 is R7R6N—, wherein R6 is H, $(C_1-C_4)$-alkyl- or cyclopropyl-, wherein one hydrogen atom of the alkyl group is optionally replaced by hydroxy, methoxy or ethoxy, and R7 is H or $(C_1-C_2)$-alkyl-;

or R5 is selected from the group of oxetanyl, tetrahydrofuranyl, tetrahydropyranyl, morpholinyl, piperidinyl, pyrrolidinyl, each optionally substituted with 1 or 2 substituents selected from the group of F, OH, $(C_1-C_4)$-alkyl-O— and $(C_1-C_4)$-alkyl-, and wherein one or more hydrogen atoms of the alkyl groups are optionally replaced by fluorine, with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl;

or a stereoisomer, stereoisomeric mixture or pharmaceutically acceptable salt thereof.

9. The compound according to claim 8, wherein

A is phenyl, optionally substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;

X is phenyl, pyridine-2-yl, pyridine-3-yl, pyridine-4-yl, thiophen-2-yl, thiophen-3-yl, thiazol-2-yl, thiazol-4-yl or thiazol-5-yl, each optionally substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—;

R1 is R5-C(=O)— or $(C_1-C_2)$-alkyl-$SO_2$—;
R2 is H, $(C_1-C_2)$-alkyl- or cyclopropyl-;
R3 is H or $(C_1-C_2)$-alkyl-;
R4 is H or $(C_1-C_2)$-alkyl-;
or R3 and R4 together form an ethylene bridge;
R5 is heteroaryl or heteroaryl-$(C_1-C_6)$-alkyl-, wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and pyrazin-3-yl, and each optionally substituted with 1 or 2 residues selected independently from F, Cl, Br, $CF_3$, methyl, ethyl, methoxy, ethoxy, CN and methyl-$SO_2$—,
with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl;
or R5 is methyl,
with the proviso if in compounds of formula I R2, R3 and R4 are hydrogen and X is a 2,4-difluorophenyl residue A is not 2 fluoro-phenyl, 3-fluoro-phenyl, 4-fluorophenyl, 3-cyano-phenyl, 3-methoxy-phenyl, 3-trifluormethoxy-phenyl, 2-fluoro-5-methoxy-phenyl, and
with the proviso if in compounds of formula I R2, R3 and R4 are hydrogen and X is a 3-cyanophenyl residue A is not a 4-fluorophenyl residue, and
with the proviso if in compounds of formula I R3 is methyl, R2 and R4 are hydrogen and X is a 2,4-difluoro-phenyl residue A is not a 4-fluoro-phenyl, and
with the proviso if in compounds of formula I R2, R3 and R4 are hydrogen and X is phenyl A is not phenyl, 3-trifluoromethyl-phenyl, 4-fluoro-phenyl, 4-chlorophenyl, 4-methyl-phenyl, 4-ethoxy-phenyl or 4-methylthiophenyl, and
with the proviso if in compounds of formula I R2, R3 and R4 are hydrogen and A is 4-fluoro-phenyl X is not 2-chloro-phenyl, 3,4-dichloro-phenyl, 4-chloro-phenyl, 4-fluoro-phenyl, 4-methyl-phenyl, 4-methoxyphenyl, 4-ethoxy-phenyl or 4-acetoxyphenyl;
or R5 is H or $(C_2-C_4)$-alkyl, $CF_3$;
or R5 to cyclopropyl, cyclobutyl, cyclopentyl, cyclohexyl or $(C_3-C_6)$-cycloalkyl-$(C_1-C_2)$-alkyl-, with the proviso if in compounds of formula I A is a 3-cyanophenyl residue and X a 2,4-difluorophenyl residue R5 is not cyclopropyl;
or R5 is $(C_1-C_2)$-alkyl-O— or $(C_1-C_2)$-alkyl-S—, wherein one or more hydrogen atoms of the alkyl moieties are optionally replaced by fluorine;
or R5 is $(C_1-C_4)$-alkyl-O-methyl- or HO—$(C_1-C_2)$-alkyl-, wherein one or more hydrogen atoms of the alkyl moieties are optionally replaced by fluorine;
or R5 is phenyl or phenyl-$(C_1-C_2)$-alkyl-, wherein the phenyl residues are optionally substituted with 1-3 residues selected independently from F, Cl, Br, $CF_3$, $(C_1-C_2)$-alkyl-, $(C_1-C_2)$-alkyl-O—, CN and methyl-$SO_2$—, and wherein one or more hydrogen atoms of the alkyl moieties are optionally replaced by fluorine,
with the proviso if in compounds of formula I A is a 3-cyanophenyl residue and X a 2,4-difluorophenyl residue R5 is not 3-methylsulfonyl-phenyl or 4-methylsulfonyl-phenyl;
or R5 is R7R6N—, wherein R6 is H, $(C_1-C_4)$-alkyl-, cyclopropyl-, wherein one hydrogen atom of the alkyl group is optionally replaced by hydroxy, methoxy or ethoxy, and R7 is H, methyl- or ethyl-;
or R5 is selected from the group of oxetanyl, tetrahydrofuranyl, tetrahydropyranyl, morpholinyl, piperidinyl, pyrrolidinyl, each optionally substituted with 1 or 2 substituents selected from the group of F, OH, $(C_1-C_2)$-alkyl-O— and $(C_1-C_4)$-alkyl-, wherein one or more hydrogen atoms of the alkyl groups are optionally replaced by fluorine;
with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl;

or a stereoisomer, stereoisomeric mixture or pharmaceutically acceptable salt thereof.

10. The compound according to claim 8, wherein

A is phenyl, optionally substituted with 1, 2 or 3 residues selected independently from F, Cl, Br, CN, $(C_1-C_4)$-alkyl-, $(C_1-C_4)$-alkyl-O— and $(C_1-C_4)$-alkyl-S—, wherein one or more hydrogen atoms of the alkyl moieties are optionally replaced by fluorine;

X is phenyl, optionally substituted with 1, 2 or 3 residues selected independently from F, Cl, Br, CN, $(C_1-C_4)$-alkyl-, $(C_1-C_4)$-alkyl-O—, $(C_1-C_4)$-alkyl-S—, $(C_1-C_4)$-alkyl-O—C(O)— and $(C_1-C_4)$-alkyl-$SO_2$—, wherein one or more hydrogen atoms of the alkyl moieties are optionally replaced by fluorine;

R1 is R5-C(=O)— or $(C_1-C_6)$-alkyl-$SO_2$—;
R2 is H, $(C_1-C_6)$-alkyl- or $(C_3-C_6)$-cycloalkyl-;
R3 is H or $(C_1-C_4)$-alkyl-;
R4 is H or $(C_1-C_4)$-alkyl-;
or R3 and R4 together form a $(C_2-C_3)$-alkylene bridge;
R5 is a heteroaryl or heteroaryl-$(C_1-C_6)$-alkyl-, wherein the heteroaryl residues are five- or six-membered ring systems, comprising 1-3 heteroatoms selected from the group N, O and S, and wherein the heteroaryl residues are optionally substituted with 1-3 residues selected independently from F, Cl, Br, $CF_3$, $(C_1-C_6)$-alkyl-, $(C_1-C_6)$-alkyl-O—, CN and $(C_1-C_2)$-alkyl-$SO_2$—, wherein one or more hydrogen atoms of the alkyl moieties are optionally replaced by fluorine;
with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl;

or R5 is methyl,
   with the proviso if in compounds of formula I R2, R3 and R4 are hydrogen and X is a 2,4-difluorophenyl residue A is not 2 fluoro-phenyl, 3-fluoro-phenyl, 4-fluorophenyl, 3-cyano-phenyl, 3-methoxy-phenyl, 3-trifluormethoxy-phenyl, or 2-fluoro-5-methoxy-phenyl, and
   with the proviso if in compounds of formula I R2, R3 and R4 are hydrogen and X is a 3-cyanophenyl residue A is not a 4-fluorophenyl residue, and
   with the proviso if in compounds of formula I R3 is methyl, R2 and R4 are hydrogen and X is a 2,4-difluoro-phenyl residue A is not a 4-fluoro-phenyl, and
   with the proviso if in compounds of formula I R2, R3 and R4 are hydrogen and X is phenyl A is not phenyl, 3-trifluoromethyl-phenyl, 4-fluoro-phenyl, 4-chlorophenyl, 4-methyl-phenyl, 4-ethyloxy-phenyl or 4-methylthiophenyl, and
   with the proviso if in compounds of formula I R2, R3 and R4 are hydrogen and A is 4-fluoro-phenyl X is not phenyl, 2-chloro-phenyl, 3,4-dichloro-phenyl, 4-chloro-phenyl, 4-fluoro-phenyl, 4-methyl-phenyl, 4-methoxy-phenyl, 4-ethyloxy-phenyl, or 4-acetoxyphenyl, and
   with the proviso if R5 is methyl and R2 is methyl, and R3 and R4 are H and A is 4 fluoro-phenyl, the residue X is not phenyl,
or R5 is H, $(C_2-C_6)$-alkyl, $CF_3$, $CF_2H$, $CFH_2$, wherein one or more hydrogen atoms of the alkyl residue may be replaced by fluorine;
or R5 is $(C_3-C_6)$-cycloalkyl or $(C_3-C_6)$-cycloalkyl-$(C_1-C_4)$-alkyl-,
   with the proviso if in compounds of formula I A is a 3-cyanophenyl residue and X a 2,4-difluorophenyl residue R5 is not cyclopropyl;
or R5 is $(C_1-C_4)$-alkyl-O— or $(C_1-C_4)$-alkyl-S—, wherein one or more hydrogen atoms of the alkyl moieties are optionally replaced by fluorine;
or R5 is $(C_1-C_4)$-alkyl-O—$(C_1-C_2)$-alkyl- or HO—$(C_1-C_4)$-alkyl-;
or R5 is phenyl or phenyl-$(C_1-C_4)$-alkyl-, wherein the phenyl residues are optionally substituted with 1-3 residues selected independently from F, Cl, Br, $CF_3$, $(C_1-C_6)$-alkyl-, $(C_1-C_6)$-alkyl-O—, CN, $(C_1-C_2)$-alkyl-$SO_2$—, wherein one or more hydrogen atoms of the alkyl moieties are optionally replaced by fluorine,
   with the proviso if in compounds of formula I A is a 3-cyanophenyl residue and X a 2,4-difluorophenyl residue R5 is not 3-methylsulfonyl-phenyl or 4-methylsulfonyl-phenyl;
or R5 is R7R6N—, wherein R6 is H, $(C_1-C_4)$-alkyl- or cyclopropyl-, wherein one hydrogen atom of the alkyl group is optionally replaced by hydroxy, methoxy or ethoxy, and wherein R7 is H or $(C_1-C_2)$-alkyl-;
or R5 is selected from the group of oxetanyl, tetrahydrofuranyl, tetrahydropyranyl, morpholinyl, piperidinyl and pyrrolidinyl, each optionally substituted with 1 or 2 substituents selected from the group of F, OH, $(C_1-C_4)$-alkyl-O— and $(C_1-C_4)$-alkyl-, wherein one or more hydrogen atoms of the alkyl groups are optionally replaced by fluorine,
   with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl;

or a stereoisomer, stereoisomeric mixture or pharmaceutically acceptable salt thereof.

11. The compound according to claim 10, wherein
A is phenyl, is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$ and $(C_1-C_2)$-alkyl-S—;
X is phenyl, is substituted with 1 or 2 residues selected independently from F, Cl, Br, CN, $(C_1-C_4)$-alkyl-, $CF_3$, $CF_2H$, $CFH_2$, methoxy, ethoxy, $OCF_3$, $(C_1-C_2)$-alkyl-S—, $(C_1-C_2)$-alkyl-O—C(O)— and methyl-$SO_2$—;
R1 is R5-C(=O)— or methyl-$SO_2$—;
R2 is H, $(C_1-C_2)$-alkyl- or cyclopropyl-;
R3 is H or methyl-;
R4 is H or methyl-;
or R3 and R4 together form an ethylene bridge;
R5 is a heteroaryl or heteroaryl-$(C_1-C_6)$-alkyl-, wherein the heteroaryl residues are selected from the group consisting of pyridine-2-yl, pyridine-3-yl, pyridine-4-yl, thiophen-2-yl, thiophen-3-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, pyrimidin-2-yl, pyrimidin-4-yl, pyrimidin-5-yl, pyridazin-3-yl, pyridazin-4-yl, pyrazin-2-yl and pyrazin-3-yl, each optionally substituted with 1 or 2 residues selected independently from F, Cl, Br, $CF_3$, methyl, ethyl, methoxy, ethoxy, CN and methyl-$SO_2$—,
   with the proviso if in compounds of formula I A is a 3-cyanophenyl residue and X a 2,4-difluorophenyl residue R5 is not pyrimidin-4-yl, pyridine-2-yl, 1-methyl-pyrazol-3-yl or 1-methyl-imidazol-2-yl;
or R5 is methyl,
   with the proviso if in compounds of formula I R2, R3 and R4 are hydrogen and X is a 2,4-difluorophenyl residue A is not 2 fluoro-phenyl, 3-fluoro-phenyl, 4-fluorophenyl, 3-cyano-phenyl, 3-methoxy-phenyl, 3-trifluormethoxy-phenyl, or 2-fluoro-5-methoxy-phenyl, and
   with the proviso if in compounds of formula I R2, R3 and R4 are hydrogen and X is a 3-cyanophenyl residue A is not a 4-fluorophenyl residue, and
   with the proviso if in compounds of formula I R3 is methyl, R2 and R4 are hydrogen and X is a 2,4-difluoro-phenyl residue A is not a 4-fluoro-phenyl, and
   with the proviso if in compounds of formula I R2, R3 and R4 are hydrogen and A is 4-fluoro-phenyl X is not 2-chloro-phenyl, 3,4-dichloro-phenyl, 4-chloro-phenyl, 4-fluoro-phenyl, 4-methyl-phenyl, 4-methoxy-phenyl, 4-ethoxy-phenyl or 4-acetoxyphenyl;
or R5 is H, $(C_2-C_4)$-alkyl or $CF_3$;
or R5 is cyclopropyl, cyclobutyl, cyclopentyl, cyclohexyl or $(C_3-C_6)$-cycloalkyl-$(C_1-C_2)$-alkyl-,
   with the proviso if in compounds of formula I A is a 3-cyanophenyl residue and X a 2,4-difluorophenyl residue R5 is not cyclopropyl;
or R5 is $(C_1-C_2)$-alkyl-O— or $(C_1-C_2)$-alkyl-S—, wherein one or more hydrogen atoms of the alkyl moieties are optionally replaced by fluorine;
or R5 is $(C_1-C_4)$-alkyl-O-methyl- or HO—$(C_1-C_2)$-alkyl-, wherein one or more hydrogen atoms of the alkyl moieties are optionally replaced by fluorine;
or R5 is phenyl or phenyl-$(C_1-C_2)$-alkyl-, wherein the phenyl residues are optionally substituted with 1-3 residues selected independently from F, Cl, Br, $CF_3$, $(C_1-C_2)$-alkyl-, $(C_1-C_2)$-alkyl-O—, CN and methyl-$SO_2$—, wherein one or more hydrogen atoms of the alkyl moieties are optionally replaced by fluorine,
with the proviso if in compounds of formula I A is a 3-cyanophenyl residue and X a 2,4-difluorophenyl residue R5 is not 3-methylsulfonyl-phenyl, or 4-methylsulfonyl-phenyl;
or R5 is R7R6N—, wherein R6 is H, ($C_1$-$C_4$)-alkyl- or cyclopropyl-, wherein one hydrogen atom of the alkyl group is optionally replaced by hydroxy, methoxy or ethoxy, and wherein R7 is H, methyl or ethyl;
or R5 is an aliphatic heterocycle, wherein the aliphatic heterocycle is selected from the group of oxetanyl, tetrahydrofuranyl, tetrahydropyranyl, morpholinyl, piperidinyl and pyrrolidinyl, and wherein the aliphatic heterocycle may be optionally substituted with 1 or 2 substituents selected from the group of F, OH, ($C_1$-$C_2$)-alkyl-O— and ($C_1$-$C_4$)-alkyl-, wherein one or more hydrogen atoms of the alkyl group are optionally replaced by fluorine,
with the proviso if in compounds of formula I A is a 3-cyanophenyl residue and X a 2,4-difluorophenyl residue R5 is not 3-methyl-oxetan-3-yl, tetrahydrofuran-3-yl, tetrahydropyran-4-yl or 1-methyl-piperidin-4-yl;
or a stereoisomer, stereoisomeric mixture or pharmaceutically acceptable salt thereof.

12. The compound according to claim 8, wherein
A is phenyl, wherein the phenyl residue is substituted with 1 or 2 residues selected independently from F, Cl, Br, CN, ($C_1$-$C_4$)-alkyl-, $CF_3$, $CF_2H$, $CFH_2$, methoxy, ethoxy, $OCF_3$ and ($C_1$-$C_2$)-alkyl-S—;
X is phenyl, wherein the phenyl residue is substituted with 1 or 2 residues selected independently from F, Cl, Br, CN, ($C_1$-$C_4$)-alkyl-, $CF_3$, $CF_2H$, $CFH_2$, methoxy, ethoxy, $OCF_3$, ($C_1$-$C_2$)-alkyl-S—, ($C_1$-$C_2$)-alkyl-O—C(O)— and methyl-$SO_2$—;
R1 is R5-C(=O)—;
R2 is H, ($C_1$-$C_2$)-alkyl- or cyclopropyl-;
R3 is H or methyl-;
R4 is H or methyl-;
or R3 and R4 together form an ethylene bridge;
R5 is ($C_2$-$C_4$)-alkyl;
or a stereoisomer, stereoisomeric mixture or pharmaceutically acceptable salt thereof.

13. The compound according to claim 1 selected from the group consisting of:
3-(3-Cyano-phenyl)-1-(2,4-difluoro-benzyl)-1,4,6,7-tetrahydro-pyrazolo[4,3-c]pyridine-5-carboxylic acid isopropylamide;
3-(4-Fluoro-phenyl)-1-[(S)-1-(4-fluoro-phenyl)-ethyl]-1,4,6,7-tetrahydro-pyrazolo[4,3-c]pyridine-5-carboxylic acid ethylamide;
3-(4-Fluoro-phenyl)-1-[(R)-1-(4-fluoro-phenyl)-ethyl]-1,4,6,7-tetrahydro-pyrazolo[4,3-c]pyridine-5-carboxylic acid ethylamide;
3-(4-Fluoro-phenyl)-1-[(S)-1-(4-fluoro-phenyl)-ethyl]-1,4,6,7-tetrahydro-pyrazolo[4,3-c]pyridine-5-carboxylic acid tert-butylamide;
3-(3-Cyano-phenyl)-1-(2,4-difluoro-benzyl)-1,4,6,7-tetrahydro-pyrazolo[4,3-c]pyridine-5-carboxylic acid ethylamide;
3-(3-Cyano-phenyl)-1-(2,4-difluoro-benzyl)-1,4,6,7-tetrahydro-pyrazolo[4,3-c]pyridine-5-carboxylic acid methylamide;
{3-(4-Fluoro-phenyl)-1-[(S)-1-(4-fluoro-phenyl)-ethyl]-1,4,6,7-tetrahydro-pyrazolo[4,3-c]pyridin-5-yl}-morpholin-4-yl-methanone;
{3-(4-Fluoro-phenyl)-1-[(S)-1-(4-fluoro-phenyl)-ethyl]-1,4,6,7-tetrahydro-pyrazolo[4,3-c]pyridin-5-yl}-((S)-3-hydroxy-pyrrolidin-1-yl)-methanone;
3-(3-Cyano-phenyl)-1-(2,4-difluoro-benzyl)-1,4,6,7-tetrahydro-pyrazolo[4,3-c]pyridine-5-carboxylic acid dimethylamide;
3-(3-Cyano-phenyl)-1-(2,4-difluoro-benzyl)-1,4,6,7-tetrahydro-pyrazolo[4,3-c]pyridine-5-carboxylic acid (2-hydroxy-ethyl)-methyl-amide;
3-[1-(2,4-Difluoro-benzyl)-5-(2-hydroxy-acetyl)-4,5,6,7-tetrahydro-1H-pyrazolo[4,3-c]pyridin-3-yl]-benzonitrile;
3-[5-Acetyl-1-(2,4-difluoro-benzyl)-4,5,6,7-tetrahydro-1H-pyrazolo[4,3-c]pyridin-3-yl]-benzonitrile;
1-[1-(2-Methyl-thiazol-4-ylmethyl)-3-(3-trifluoromethyl-phenyl)-1,4,6,7-tetrahydro-pyrazolo[4,3-c]pyridin-5-yl]-ethanone;
1-[1-Thiazol-2-ylmethyl-3-(3-trifluoromethyl-phenyl)-1,4,6,7-tetrahydro-pyrazolo[4,3-c]pyridin-5-yl]-ethanone;
1-[1-(5-Chloro-thiophen-2-ylmethyl)-3-m-tolyl-1,4,6,7-tetrahydro-pyrazolo[4,3-c]pyridin-5-yl]-ethanone;
1-[1-(5-Chloro-thiophen-2-ylmethyl)-3-(3-trifluoromethyl-phenyl)-1,4,6,7-tetrahydro-pyrazolo[4,3-c]pyridin-5-yl]-ethanone;
3-[5-Acetyl-1-(5-chloro-thiophen-2-ylmethyl)-4,5,6,7-tetrahydro-1H-pyrazolo[4,3-c]pyridin-3-yl]-benzonitrile;
1-[3-(3-Chloro-phenyl)-1-(5-chloro-thiophen-2-ylmethyl)-1,4,6,7-tetrahydro-pyrazolo[4,3-c]pyridin-5-yl]-ethanone;
4-[5-Acetyl-3-(3-trifluoromethyl-phenyl)-4,5,6,7-tetrahydro-pyrazolo[4,3-c]pyridin-1-ylmethyl]-benzonitrile;
3-{5-Acetyl-1-[1-(4-fluoro-phenyl)-ethyl]-4,5,6,7-tetrahydro-1H-pyrazolo[4,3-c]pyridin-3-yl}-benzonitrile;
1-[1-[Cyclopropyl-(4-fluoro-phenyl)-methyl]-3-(4-fluoro-phenyl)-1,4,6,7-tetrahydro-pyrazolo[4,3-c]pyridin-5-yl]-ethanone;
1-[1-(2,4-Difluoro-benzyl)-3-(3-trifluoromethoxy-phenyl)-1,4,6,7-tetrahydro-pyrazolo[4,3-c]pyridin-5-yl]-ethanone;
1-[1-(2,6-Difluoro-benzyl)-3-(4-fluoro-phenyl)-1,4,6,7-tetrahydro-pyrazolo[4,3-c]pyridin-5-yl]-ethanone;
1-{3-(4-Fluoro-phenyl)-1-[1-(4-fluoro-phenyl)-ethyl]-1,4,6,7-tetrahydro-pyrazolo[4,3-c]pyridin-5-yl}-ethanone;
1-[3-(4-Fluoro-phenyl)-1-(4-trifluoromethyl-benzyl)-1,4,6,7-tetrahydro-pyrazolo[4,3-c]pyridin-5-yl]-ethanone;
1-[1-(2,4-Difluoro-benzyl)-3-(3-methoxy-phenyl)-1,4,6,7-tetrahydro-pyrazolo[4,3-c]pyridin-5-yl]-ethanone;
1-[3-(4-Fluoro-phenyl)-1-(3-trifluoromethyl-benzyl)-1,4,6,7-tetrahydro-pyrazolo[4,3-c]pyridin-5-yl]-ethanone;
1-[1-[1-(4-Fluoro-phenyl)-ethyl]-3-(3-trifluoromethoxy-phenyl)-1,4,6,7-tetrahydro-pyrazolo[4,3-c]pyridin-5-yl]-ethanone;
1-[1-(2,4-Difluoro-benzyl)-3-(4-fluoro-3-methoxy-phenyl)-1,4,6,7-tetrahydro-pyrazolo[4,3-c]pyridin-5-yl]-ethanone;
3-[5-Acetyl-1-(2,5-difluoro-benzyl)-4,5,6,7-tetrahydro-1H-pyrazolo[4,3-c]pyridin-3-yl]-benzonitrile;
1-[1-(2,4-Difluoro-benzyl)-3-m-tolyl-1,4,6,7-tetrahydro-pyrazolo[4,3-c]pyridin-5-yl]-ethanone;
1-[1-(6-Chloro-pyridin-3-ylmethyl)-3-(3-trifluoromethyl-phenyl)-1,4,6,7-tetrahydro-pyrazolo[4,3-c]pyridin-5-yl]-ethanone;

1-[3-(3-Chloro-phenyl)-1-(4-fluoro-2-methyl-benzyl)-1,4,6,7-tetrahydro-pyrazolo[4,3-c]pyridin-5-yl]-ethanone;
1-[1-(2-Fluoro-benzyl)-3-m-tolyl-1,4,6,7-tetrahydro-pyrazolo[4,3-c]pyridin-5-yl]-ethanone;
1-[1-(2-Methoxy-benzyl)-3-(3-trifluoromethyl-phenyl)-1,4,6,7-tetrahydro-pyrazolo[4,3-c]pyridin-5-yl]-ethanone;
1-[3-(3-Chloro-phenyl)-1-(3-methoxy-benzyl)-1,4,6,7-tetrahydro-pyrazolo[4,3-c]pyridin-5-yl]-ethanone;
1-[1-(4-Chloro-3-fluoro-benzyl)-3-(4-fluoro-phenyl)-1,4,6,7-tetrahydro-pyrazolo[4,3-c]pyridin-5-yl]-ethanone;
1-[1-(2,4-Difluoro-benzyl)-3-(2-fluoro-5-methoxy-phenyl)-1,4,6,7-tetrahydro-pyrazolo[4,3-c]pyridin-5-yl]-ethanone;
5-[5-Acetyl-1-(2,4-difluoro-benzyl)-4,5,6,7-tetrahydro-1H-pyrazolo[4,3-c]pyridin-3-yl]-2-fluoro-benzonitrile;
1-[1-(2,4-Difluoro-benzyl)-3-(3-fluoro-phenyl)-1,4,6,7-tetrahydro-pyrazolo[4,3-c]pyridin-5-yl]-ethanone;
1-[1-(2,4-Difluoro-benzyl)-3-(4-trifluoromethyl-phenyl)-1,4,6,7-tetrahydro-pyrazolo[4,3-c]pyridin-5-yl]-ethanone;
1-[1-[(R)-1-(4-Chloro-phenyl)-propyl]-3-(4-fluoro-phenyl)-1,4,6,7-tetrahydro-pyrazolo[4,3-c]pyridin-5-yl]-ethanone;
1-[1-[(S)-1-(4-Chloro-phenyl)-propyl]-3-(4-fluoro-phenyl)-1,4,6,7-tetrahydro-pyrazolo[4,3-c]pyridin-5-yl]-ethanone;
1-[1-(2-Fluoro-4-methyl-benzyl)-3-(3-trifluoromethyl-phenyl)-1,4,6,7-tetrahydro-pyrazolo[4,3-c]pyridin-5-yl]-ethanone;
1-[1-(4-Chloro-pyridin-3-ylmethyl)-3-(3-trifluoromethyl-phenyl)-1,4,6,7-tetrahydro-pyrazolo[4,3-c]pyridin-5-yl]-ethanone;
1-[1-(3-Methyl-pyridin-2-ylmethyl)-3-(3-trifluoromethyl-phenyl)-1,4,6,7-tetrahydro-pyrazolo[4,3-c]pyridin-5-yl]-ethanone;
1-[1-(2,4-Difluoro-benzyl)-3-(4-fluoro-phenyl)-1,4,6,7-tetrahydro-pyrazolo[4,3-c]pyridin-5-yl]-ethanone;
3-[11-Acetyl-5-(2,4-difluoro-benzyl)-4,5,11-triaza-tricyclo[6.2.1.02,6]undeca-2(6),3-dien-3-yl]-benzonitrile;
1-[5-(2,4-Difluoro-benzyl)-3-(4-fluoro-phenyl)-4,5,11-triaza-tricyclo[6.2.1.02,6]undeca-2(6),3-dien-11-yl]-ethanone;
1-[1-(6-Chloro-pyridin-3-ylmethyl)-3-m-tolyl-1,4,6,7-tetrahydro-pyrazolo[4,3-c]pyridin-5-yl]-ethanone;
1-[1-(4-Methoxy-pyridin-2-ylmethyl)-3-(3-trifluoromethyl-phenyl)-1,4,6,7-tetrahydro-pyrazolo[4,3-c]pyridin-5-yl]-ethanone;
1-[1-(4-Chloro-pyridin-3-ylmethyl)-3-m-tolyl-1,4,6,7-tetrahydro-pyrazolo[4,3-c]pyridin-5-yl]-ethanone;
1-[1-(3-Methoxy-pyridin-2-ylmethyl)-3-(3-trifluoromethyl-phenyl)-1,4,6,7-tetrahydro-pyrazolo[4,3-c]pyridin-5-yl]-ethanone;
1-[3-(3-Chloro-phenyl)-1-(3-methyl-pyridin-2-ylmethyl)-1,4,6,7-tetrahydro-pyrazolo[4,3-c]pyridin-5-yl]-ethanone;
3-[1-(2,4-Difluoro-benzyl)-5-(3-methyl-oxetane-3-carbonyl)-4,5,6,7-tetrahydro-1H-pyrazolo[4,3-c]pyridin-3-yl]-benzonitrile;
3-[1-(2,4-Difluoro-benzyl)-5-isobutyryl-4,5,6,7-tetrahydro-1H-pyrazolo[4,3-c]pyridin-3-yl]-benzonitrile;
3-[5-Cyclopropanecarbonyl-1-(2,4-difluoro-benzyl)-4,5,6,7-tetrahydro-1H-pyrazolo[4,3-c]pyridin-3-yl]-benzonitrile;
3-[5-(2-tert-Butoxy-acetyl)-1-(2,4-difluoro-benzyl)-4,5,6,7-tetrahydro-1H-pyrazolo[4,3-c]pyridin-3-yl]-benzonitrile;
3-[1-(2,4-Difluoro-benzyl)-5-(3-methanesulfonyl-benzoyl)-4,5,6,7-tetrahydro-1H-pyrazolo[4,3-c]pyridin-3-yl]-benzonitrile;
[1-Benzyl-3-(4-fluoro-phenyl)-1,4,6,7-tetrahydro-pyrazolo[4,3-c]pyridin-5-yl]-(4-fluoro-phenyl)-methanone;
[1-Benzyl-3-(4-fluoro-phenyl)-1,4,6,7-tetrahydro-pyrazolo[4,3-c]pyridin-5-yl]-(4-methoxy-phenyl)-methanone;
[1-Benzyl-3-(4-fluoro-phenyl)-1,4,6,7-tetrahydro-pyrazolo[4,3-c]pyridin-5-yl]-phenyl-methanone;
3-[5-Cyclobutanecarbonyl-1-(2,4-difluoro-benzyl)-4,5,6,7-tetrahydro-1H-pyrazolo[4,3-c]pyridin-3-yl]-benzonitrile;
3-[5-Cyclopentanecarbonyl-1-(2,4-difluoro-benzyl)-4,5,6,7-tetrahydro-1H-pyrazolo[4,3-c]pyridin-3-yl]-benzonitrile;
3-[1-(2,4-Difluoro-benzyl)-5-(4-methanesulfonyl-benzoyl)-4,5,6,7-tetrahydro-1H-pyrazolo[4,3-c]pyridin-3-yl]-benzonitrile;
3-[1-(2,4-Difluoro-benzyl)-5-(tetrahydro-pyran-4-carbonyl)-4,5,6,7-tetrahydro-1H-pyrazolo[4,3-c]pyridin-3-yl]-benzonitrile;
3-[1-(2,4-Difluoro-benzyl)-5-(tetrahydro-furan-3-carbonyl)-4,5,6,7-tetrahydro-1H-pyrazolo[4,3-c]pyridin-3-yl]-benzonitrile;
3-[1-(2,4-Difluoro-benzyl)-5-(2-methoxy-acetyl)-4,5,6,7-tetrahydro-1H-pyrazolo[4,3-c]pyridin-3-yl]-benzonitrile;
3-[1-(2,4-Difluoro-benzyl)-5-(2,2-dimethyl-propionyl)-4,5,6,7-tetrahydro-1H-pyrazolo[4,3-c]pyridin-3-yl]-benzonitrile;
3-[1-(2,4-Difluoro-benzyl)-5-propionyl-4,5,6,7-tetrahydro-1H-pyrazolo[4,3-c]pyridin-3-yl]-benzonitrile;
3-[1-(2,4-Difluoro-benzyl)-5-((S)-2-hydroxy-propionyl)-4,5,6,7-tetrahydro-1H-pyrazolo[4,3-c]pyridin-3-yl]-benzonitrile;
1-[1-Benzyl-3-(4-fluoro-phenyl)-1,4,6,7-tetrahydro-pyrazolo[4,3-c]pyridin-5-yl]-2-phenyl-ethanone;
3-[5-Butyryl-1-(2,4-difluoro-benzyl)-4,5,6,7-tetrahydro-1H-pyrazolo[4,3-c]pyridin-3-yl]-benzonitrile;
3-[1-(2,4-Difluoro-benzyl)-5-(pyridine-2-carbonyl)-4,5,6,7-tetrahydro-1H-pyrazolo[4,3-c]pyridin-3-yl]-benzonitrile;
3-[1-(2,4-Difluoro-benzyl)-5-(3-fluoro-pyridine-4-carbonyl)-4,5,6,7-tetrahydro-1H-pyrazolo[4,3-c]pyridin-3-yl]-benzonitrile;
3-[1-(2,4-Difluoro-benzyl)-5-(pyrimidine-4-carbonyl)-4,5,6,7-tetrahydro-1H-pyrazolo[4,3-c]pyridin-3-yl]-benzonitrile;
3-[1-(2,4-Difluoro-benzyl)-5-(3-methyl-3H-imidazole-4-carbonyl)-4,5,6,7-tetrahydro-1H-pyrazolo[4,3-c]pyridin-3-yl]-benzonitrile;
3-[1-(2,4-Difluoro-benzyl)-5-(1-methyl-1H-pyrazole-3-carbonyl)-4,5,6,7-tetrahydro-1H-pyrazolo[4,3-c]pyridin-3-yl]-benzonitrile;
3-(3-Cyano-phenyl)-1-(2,4-difluoro-benzyl)-1,4,6,7-tetrahydro-pyrazolo[4,3-c]pyridine-5-carboxylic acid ethyl ester;
1-[1-(2,4-Difluoro-benzyl)-3-(4-fluoro-phenyl)-6-methyl-1,4,6,7-tetrahydro-pyrazolo[4,3-c]pyridin-5-yl]-ethanone;
3-(4-Fluoro-phenyl)-1-[(R)-1-(4-fluoro-phenyl)-ethyl]-5-methanesulfonyl-4,5,6,7-tetrahydro-1H-pyrazolo[4,3-c]pyridine;

3-(4-Fluoro-phenyl)-1-[(S)-1-(4-fluoro-phenyl)-ethyl]-5-methanesulfonyl-4,5,6,7-tetrahydro-1H-pyrazolo[4,3-c]pyridine;

or a stereoisomer, stereoisomeric mixture or pharmaceutically acceptable salt thereof.

14. A pharmaceutical composition comprising a compound of claim 1 or a pharmaceutically acceptable salt thereof.

15. A pharmaceutical composition comprising a compound of claim 13 or a pharmaceutically acceptable salt thereof.

\* \* \* \* \*